US012049638B2

(12) United States Patent
Perry, III et al.

(10) Patent No.: US 12,049,638 B2
(45) Date of Patent: Jul. 30, 2024

(54) SYNTHETIC GENETIC ELEMENTS FOR BIOMANUFACTURE

(71) Applicant: Janssen Biotech, Inc., Horsham, PA (US)

(72) Inventors: William Lloyd Perry, III, Warrington, PA (US); Brian Tomkowicz, North Wales, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 730 days.

(21) Appl. No.: 16/934,970

(22) Filed: Jul. 21, 2020

(65) Prior Publication Data

US 2021/0032657 A1 Feb. 4, 2021

Related U.S. Application Data

(60) Provisional application No. 62/877,524, filed on Jul. 23, 2019, provisional application No. 62/877,551, filed on Jul. 23, 2019, provisional application No. 62/877,508, filed on Jul. 23, 2019, provisional application No. 62/877,532, filed on Jul. 23, 2019, provisional application No. 62/877,540, filed on Jul. 23, 2019, provisional application No. 62/877,516, filed on Jul. 23, 2019, provisional application No. 62/877,561, filed on Jul. 23, 2019, provisional application No. 62/877,577, filed on Jul. 23, 2019.

(51) Int. Cl.
*C12N 7/00* (2006.01)
*C12N 15/86* (2006.01)

(52) U.S. Cl.
CPC ............... *C12N 15/86* (2013.01); *C12N 7/00* (2013.01); *C12N 2750/14121* (2013.01); *C12N 2750/14151* (2013.01); *C12N 2800/50* (2013.01); *C12N 2830/36* (2013.01); *C12N 2830/40* (2013.01); *C12N 2830/42* (2013.01); *C12N 2830/50* (2013.01)

(58) Field of Classification Search
None
See application file for complete search history.

(56) References Cited

U.S. PATENT DOCUMENTS

| | | | |
|---|---|---|---|
| 6,340,595 B1 | 1/2002 | Vogels et al. | |
| 7,348,178 B1 | 3/2008 | Schneider | |
| 2003/0190746 A1 | 10/2003 | Xiao | |

FOREIGN PATENT DOCUMENTS

| | | |
|---|---|---|
| CN | 101522903 A | 9/2009 |
| CN | 102994492 A | 3/2013 |
| GB | 2566572 A | 3/2019 |
| WO | WO 2006083253 A1 | 8/2006 |
| WO | WO 2008024998 A2 | 2/2008 |
| WO | WO 2017207979 A1 | 12/2017 |

OTHER PUBLICATIONS

Brown, W.R., Lee, N.C., Xu, Z. and Smith, M.C., 2011. Serine recombinases as tools for genome engineering. Methods, 53(4), pp. 372-379. (Year: 2011).*
Altschul et al., 1997, "Gapped BLAST and PSI-BLAST: a new generation of protein database search programs," Nucleic Acids Res., 25(17):3389-3402.
Aslanidi et al., 2009, "An inducible system for highly efficient production of recombinant adeno-associated virus (rAAV) vectors in insect Sf9 cells," Proc Natl Acad Sci USA, 106(13):5059-5064.
Beall et al., 2007, "Abstract 84: High Titer Adeno-Associated Viral Vector Production by a Vero-Derived Producer Cell Line, 10th Annual Meeting of American Society of Gene Therapy," Seattle, WA, May 30-Jun. 3, 2007 (1 page).
Brunak et al., 1991, "Prediction of human mRNA donor and acceptor sites from the DNA sequence," J Mol Biol., 220(1):49-65.
Cecchini et al., 2011, "Reproducible high yields of recombinant adeno-associated virus produced using invertebrate cells in 0.02- to 200-liter cultures," Hum Gene Ther., 22(8):1021-1030.
Chadeuf et al., 2000, "Efficient recombinant adeno-associated virus production by a stable rep-cap HeLa cell line correlates with adenovirus-induced amplification of the integrated rep-cap genome," J Gene Med., 2(4):260-268.
Chadeuf et al., 2005, "Evidence for encapsidation of prokaryotic sequences during recombinant adeno-associated virus production and their in vivo persistence after vector delivery," Mol Ther., 12(4):744-753.
Clark et al., 1995, "Cell lines for the production of recombinant adeno-associated virus," Hum Gene Ther., 6(10):1329-1341.
Clement et al., 2009, "Large-scale adeno-associated viral vector production using a herpesvirus-based system enables manufacturing for clinical studies," Hum Gene Ther., 20(8):796-806.
Cuesta et al., 2004, "Structural basis for competitive inhibition of eIF4G-Mnk1 interaction by the adenovirus 100-kilodalton protein," J Virol., 78(14):7707-7716.
Daya et al., 2008, "Gene therapy using adeno-associated virus vectors," Clin Microbiol Rev., 21(4):583-593.

(Continued)

*Primary Examiner* — Neil P Hammell
*Assistant Examiner* — Khaleda B Hasan
(74) *Attorney, Agent, or Firm* — JONES DAY

(57) ABSTRACT

Disclosed are non-naturally occurring nucleic acid molecules comprising nucleotide sequences encoding serine recombinases. Also disclosed are vectors comprising non-naturally occurring nucleic acid molecule, and cells comprising the non-naturally occurring nucleic acid molecule or the vector. Recombinant constructs, cells and means for improved production of Adeno-Associated Viruses (AAVs) are described. Also described are methods of using the constructs and cells to produce recombinant AAVs.

20 Claims, 6 Drawing Sheets

Specification includes a Sequence Listing.

(56) References Cited

OTHER PUBLICATIONS

De Benedetti et al., 1983, "Phosphorylation of initiation factor eIF-2 alpha, binding of mRNA to 48 S complexes, and its reutilization in initiation of protein synthesism" J Biol Chem., 258(23):14556-14562.
Fallaux et al., 1998, "New helper cells and matched early region 1-deleted adenovirus vectors prevent generation of replication-competent adenoviruses," Hum Gene Ther., 9(13):1909-1917.
Fisher et al., 1996, "A novel adenovirus-adeno-associated virus hybrid vector that displays efficient rescue and delivery of the AAV genome," Hum Gene Ther., 7(17):2079-2087.
Gao et al., 1998, "High-titer adeno-associated viral vectors from a Rep/Cap cell line and hybrid shuttle virus," Hum Gene Ther., 9(16):2353-2362.
Gao et al., 2002, "Rep/Cap gene amplification and high-yield production of AAV in an A549 cell line expressing Rep/Cap," Mol Ther., 5(5 Pt 1):644-649.
Gao et al., 2008, "279. Inadvertent Gene Transfer of Co-Packaged Rep and Cap Sequences during the Production of AAV Vector and Its Potential Impact on Vector Performance," 16(Supp 1):S105-S106.
Gao et al., 2008, "Human branch point consensus sequence is yUnAy," Nucleic Acids Res., 36(7):2257-2267.
GenBank Accession No. AF028704.1, "Adeno-associated virus 6, complete genome," Jan. 12, 1998 (3 pages).
GenBank Accession No. AY040835.1, "Gallus gallus beta-globin gene, regulatory region," Feb. 26, 2002 (2 pages).
GenBank Accession No. AY190749.1, "*Homo sapiens* isolate 4 anti-repressor element," May 5, 2003 (2 pages).
GenBank Accession No. AY190750.1, "*Homo sapiens* isolate 6 anti-repressor element," May 5, 2003 (2 pages).
GenBank Accession No. AY190751.1, "*Homo sapiens* isolate 7 anti-repressor element," May 5, 2003 (2 pages).
GenBank Accession No. AY190752.1, "*Homo sapiens* isolate 12 anti-repressor element," May 5, 2003 (2 pages).
GenBank Accession No. AY190753.1, "*Homo sapiens* isolate 13 anti-repressor element," May 5, 2003 (2 pages).
GenBank Accession No. AY190754.1, "*Homo sapiens* isolate 35 anti-repressor element," May 5, 2003 (1 page).
GenBank Accession No. AY190755.1, "*Homo sapiens* isolate 36 anti-repressor element," May 5, 2003 (2 pages).
GenBank Accession No. AY190756.1, "*Homo sapiens* isolate 40 anti-repressor element," May 5, 2003 (2 pages).
GenBank Accession No. AY190757.1, "*Homo sapiens* isolate 52 anti-repressor element," May 5, 2003 (1 page).
GenBank Accession No. AY530579.1, "Adeno-associated virus 9 isolate hu.14 capsid protein VP1 (cap) gene, complete cds," Jun. 24, 2004 (2 pages).
GenBank Accession No. NC_000020.11, "*Homo sapiens* chromosome 20, GRCh38.p13 Primary Assembly," Nov. 22, 2020 (3 pages).
GenBank Accession No. NC_000086.7, "Mus musculus strain C57BL/6J chromosome X, GRCm38.p6 C57BL/6J," Jun. 24, 2020 (2 pages).
GenBank Accession No. NC_001401.2, "Adeno-associated virus—2, complete genome," Aug. 13, 2018 (6 pages).
GenBank Accession No. NC_001669.1, "Simian virus 40 complete genome," Jun. 4, 2019 (18 pages).
GenBank Accession No. NC_001729.1, "Adeno-associated virus—3, complete genome," Aug. 13, 2018 (3 pages).
GenBank Accession No. NC_001829.1, "Adeno-associated virus—4, complete genome," Aug. 13, 2018 (3 pages).
GenBank Accession No. NC_002077.1, "Adeno-associated virus—1, complete genome," Aug. 13, 2018 (3 pages).
GenBank Accession No. NC_006152.1, "Adeno-associated virus 5, complete genome," Aug. 13, 2018 (3 pages).
GenBank Accession No. NC_006260.1, "Adeno-associated virus—7, complete genome," Aug. 13, 2018 (3 pages).
GenBank Accession No. NC_006261.1, "Adeno-associated virus—8, complete genome," Aug. 13, 2018 (3 pages).
GenBank Accession No. NZ_JFBY01000018.1, "Bacillus safensis strain Fairview contig56_1, whole genome shotgun sequence," Jun. 2, 2020 (143 pages).
GenBank Accession No. AY190758.1, "*Homo sapiens* isolate 53 anti-repressor element," May 5, 2003 (2 pages).
GenPept Accession No. 3J1Q_A, "Structure of AAV-DJ, a Retargeted Gene Therapy Vector: Cryo-Electron Microscopy at 4.5A resolution," Dec. 1, 2020 (3 pages).
GenPept Accession No. WP_029708089.1, "recombinase family protein [Bacillus safensis]," Apr. 30, 2020 (2 pages).
Grieger et al., 2005, "Packaging capacity of adeno-associated virus serotypes: impact of larger genomes on infectivity and postentry steps," J Virol., 79(15):9933-9944.
Hauck et al., 2009, "Undetectable transcription of cap in a clinical AAV vector: implications for preformed capsid in immune responses," Mol Ther., 17(1):144-152 (Epub 2008).
Havenga et al., 2001, "Improved adenovirus vectors for infection of cardiovascular tissues," J Virol., 75(7):3335-3342.
Hinderer et al., 2018, "Severe Toxicity in Nonhuman Primates and Piglets Following High-Dose Intravenous Administration of an Adeno-Associated Virus Vector Expressing Human SMN," Hum Gene Ther., 29(3):285-298.
Huang et al., 1990, "Adenovirus inhibition of cellular protein synthesis is prevented by the drug 2-aminopurine," Proc Natl Acad Sci USA, 87(18):7115-7119.
International Searching Authority, International Search Report and Written Opinion for International Patent Application No. PCT/US2020/042854 (Pub No. WO 2021016227) dated Dec. 11, 2020 (22 pages).
Kharma et al., 2016, "Automated design of hammerhead ribozymes and validation by targeting the PABPN1 gene transcript," Nucleic Acids Res., 44(4):e39 (12 pages) (Epub 2015).
Kwaks et al., 2003, "Identification of anti-repressor elements that confer high and stable protein production in mammalian cells," Nat Biotechnol., 21(5):553-558 and Erratum 21(7):822.
Liu et al., 1999, "Production of recombinant adeno-associated virus vectors using a packaging cell line and a hybrid recombinant adenovirus," Gene Ther., 6(2):293-299.
Mccarty, 2008, "Self-complementary AAV vectors; advances and applications," Mol Ther., 16(10):1648-1656.
Mietzsch et al., 2014, "OneBac: platform for scalable and high-titer production of adeno-associated virus serotype 1-12 vectors for gene therapy," Hum Gene Ther., 25(3):212-222.
Nony et al., 2003, "Evidence for packaging of rep-cap sequences into adeno-associated virus (AAV) type 2 capsids in the absence of inverted terminal repeats: a model for generation of rep-positive AAV particles," J Virol., 77(1):776-781.
Ogasawara et al., 1999, "Highly regulated expression of adeno-associated virus large Rep proteins in stable 293 cell lines using the Cre/IoxP switching system," J Gen Virol., 80( Pt 9):2477-2480.
Rutherford et al., 2013, "Attachment site recognition and regulation of directionality by the serine integrases," Nucleic Acids Res., 41(17):8341-8356.
Schnodt et al., 2017, "Improving the Quality of Adeno-Associated Viral Vector Preparations: The Challenge of Product-Related Impurities," Hum Gene Ther Methods, 28(3):101-108.
Teixeira et al., 2004, "Autocatalytic RNA cleavage in the human beta-globin pre-mRNA promotes transcription termination," Nature, 432(7016):526-530.
Thomas et al., 2009, "Scalable recombinant adeno-associated virus production using recombinant herpes simplex virus type 1 coinfection of suspension-adapted mammalian cells," Hum Gene Ther., 20(8):861-870.
Wang et al., 2017, "A Robust System for Production of Superabundant VP1 Recombinant AAV Vectors," Mol Ther Methods Clin Dev., 7:146-156.
West et al., 2008, "Molecular dissection of mammalian RNA polymerase II transcriptional termination," Mol Cell, 29(5):600-610.

(56) References Cited

OTHER PUBLICATIONS

Yang et al., 1994, "Characterization of cell lines that inducibly express the adeno-associated virus Rep proteins," J Virol., 68(8):4847-4856.
Yuan et al., 2011, "A versatile adeno-associated virus vector producer cell line method for scalable vector production of different serotypes," Hum Gene Ther., 22(5):613-624.
Yueh et al., 2000, "Translation by ribosome shunting on adenovirus and hsp70 mRNAs facilitated by complementarity to 18S rRNA", Genes Dev., 14(4):414-421.
Zhang et al., 1994, "Adenovirus inhibition of cell translation facilitates release of virus particles and enhances degradation of the cytokeratin network," J Virol., 68(4):2544-2555.
Cao et al., 2000, "High-titer, wild-type free recombinant adeno-associated virus vector production using intron-containing helper plasmids," J Virol., 74(24):11456-11463.
Qiao et al., 2002, "A novel gene expression control system and its use in stable, high-titer 293 cell-based adeno-associated virus packaging cell lines," J Virol., 76(24):13015-13027.
Partial International Search Report and Provisional Opinion for International Patent Application No. PCT/US2020/042854 dated Oct. 14, 2020 (12 pages).
GenPept Accession No. WP_029708089.1, "resolvase [Bacillus pumilus]," Jun. 24, 2014 (2 pages).

* cited by examiner

| Score | Expect | Method | Identities | Positives | Gaps |
|---|---|---|---|---|---|
| 697 bits(1798) | 0.0 | Compositional matrix adjust. | 341/531(64%) | 415/531(78%) | 2/531(0%) |

```
Query  1    MELKNIVNSYNITNILGYLRRSRQDMEREKRTGEDTLTEQKELMNKILTAIEIPYELKME  60
            MELK+IVNSYN+T I+GYLRRSRQD+EREKRTGEDTLTEQKELMNKILT IEIPYE + E
Sbjct  1    MELKHIVNSYNVTKIIGYLRRSRQDVEREKRTGEDTLTEQKELMNKILTGIEIPYETRTE  60

Query  61   IGSGESIDGRPVFKECLKDLEEGKYQAIAVKEITRLSRGSYSDAGQIVNLLQSKRLIIIT  120
            IGSGESI+GRPVFK CL DL  GK+QAIAVKEITRLSRGSYSDAG+IVNLL  KR+IIIT
Sbjct  61   IGSGESIEGRPVFKSCLADLRSGKFQAIAVKEITRLSRGSYSDAGEIVNLLNEKRIIIIT  120

Query  121  PYKVYDPRNPVDMRQIRFELFMAREEFEMTRERMTGAKYTYAAQGKWISGLAPYGYQLNK  180
            PYK+YDPRNPVD RQIRFELFMAREEFEMTRERM GAK+TYAAQGKWISGLAP+GY+LNK
Sbjct  121  PYKIYDPRNPVDARQIRFELFMAREEFEMTRERMNGAKFTYAAQGKWISGLAPFGYKLNK  180

Query  181  KTSKLDPVEDEAKVVQLIFNIFLNGLNGKDYSYTAIASHLTNLQIPTPSGKKRWNQYTIK  240
            +TS+L+P +++  VV+LIF+IFLNGL+GKD SYTAIA+HL+ LQ  TP G KRW++ T++
Sbjct  181  RTSRLEPSDEDKVVVKLIFDIFLNGLDGKDLSYTAIATHLSKLQFTTPRGGKRWSKDTVR  240

Query  241  AILQNEVYIGTVKYKVREKTKDGKRTIRPEKEQIVVQDAHAPIIDKEQFQQSQVKIANKV  300
             ILQNE Y+G V+YK RE TKDGK+  RPE E IVV DAH PII+KE F+  Q KI NKV
Sbjct  241  KILQNEAYMGRVRYKARETTKDGKKVFRPESEHIVVDDAHEPIINKEDFEAVQEKIKNKV  300

Query  301  PLLPNKDEFELSELAGVCTCSKCGEPLSKYESKRIRKNKDGTESVYHVKSLTCKKNKCTY  360
            PLLP    +E +ELAG+C CS CG+ L K+ES+  RKNKDGT S +HVK L CK NKCT
Sbjct  301  PLLPVVTSYEPNELAGICVCSVCGKSLQKFESEYNRKNKDGTSSYFHVKLLICKINKCTS  360

Query  361  VRYNDVENAILDYLSSLNDLNDSTLTKHINSMLSKYEDDNSNMKTKKQMSEHLSQKEKEL  420
            VRY  VE AIL+YL  L  L ++ L   I   +   E +NS  KT +QM    +QK+KEL
Sbjct  361  VRYEYVEEAILEYLEQLIALENNKLKAIIEKSMEAAETNNSE-KTSEQMLVQANQKQKEL  419

Query  421  KNKENFIFDKYESGIYSDELFLKRKAALDEEFKELQNAKNELNGLQDTQSEIDSNTVRNN  480
            +NK  FIF+K+ESGIY+DE+FL+RKAA+++E  +++  K EL+   + + E D N  R N
Sbjct  420  ENKLTFIFEKFESGIYTDEMFLQRKAAIEKEVADIKKLKQELSMTFEVK-EKDVNEFRVN  478

Query  481  INKIIDQYHIESSSEKKNELLRMVLKDVIVNMTQKRKGPIPAQFEITPILR  531
            I+ ++  Y    S   KNE LR +   +++ MT+KR+GPIPA+F I P+LR
Sbjct  479  ISDVVKFYKESKSRGLKNEKLRSIFDFIVLEMTEKRRGPIPAKFNIYPVLR  529
```

Figure 1

| Score | Expect | Identities | Gaps | Strand |
|---|---|---|---|---|
| 874 bits(473) | 0.0 | 483/488(99%) | 0/488(0%) | Plus/Minus |

```
Query  113     ACTGACAAAGCGGTTTCTCCAACGAATGCCATGGGTGCAACAAAATTGATTTCAGAAAAA  172
               ||||||||||||||||||||||||||||||||||||||||||||||||||||||||||||
Sbjct  464839  ACTGACAAAGCGGTTTCTCCAACGAATGCCATGGGTGCAACAAAATTGATTTCAGAAAAA  464780

Query  173     CTATTTTTCCAAGCAAACGAAAGTATTCCGAATCAAAAAACGAGGTTTTGCTCTGTACGC  232
               ||||||||||||||||||||||||||||| ||| ||||||| | ||||||||||||||||
Sbjct  464779  CTATTTTTCCAAGCAAACGAAAGTATTCCAAATAAAAAAACCAAGTTTTGCTCTGTACGC  464720

Query  233     TTTGGCAATGTGCTTGGATCTAGAGGTTCCGTTATTCCGATCATGCTCCAGCAGCTATTA  292
               |||||||||||||||||||||||||||||||| |||||||||||||||||||||||||||
Sbjct  464719  TTTGGCAATGTGCTTGGATCTAGAGGTTCCGTGATTCCGATCATGCTCCAGCAGCTATTA  464660

Query  293     AATGAAAAACCTTTGACCGTGACTGATCCTCATATGACACGtttttttATGTCCATTGAA  352
               ||||||||||||||||||||||||||||||||||||||||||||||||||||||||||||
Sbjct  464659  AATGAAAAACCTTTGACCGTGACTGATCCTCATATGACACGTTTTTTTATGTCCATTGAA  464600

Query  353     GAGGCTGTTTCCCTCACACTTCAAGCAGCAATCATGATGAAAGGCGGCGAAACCTTCATT  412
               ||||||||||||||||||||||||||||||||||||||||||||||||||||||||||||
Sbjct  464599  GAGGCTGTTTCCCTCACACTTCAAGCAGCAATCATGATGAAAGGCGGCGAAACCTTCATT  464540

Query  413     CTCAAGATGGAGTCCTTACAGCTTGCCGATCTCCTAAAAGCGTTTCATGAATATGCCGCT  472
               ||||||||||||||||||||||||||||||||||||||||||||||||||||||||||||
Sbjct  464539  CTCAAGATGGAGTCCTTACAGCTTGCCGATCTCCTAAAAGCGTTTCATGAATATGCCGCT  464480

Query  473     CAAATCAATGCTAAATCTCCGGATATTCTTGTAGTCGGAAAAAGACCTGGCGAAAAGCTT  532
               ||||||||||||||||||||||||||||||||||||||||||||||||||||||||||||
Sbjct  464479  CAAATCAATGCTAAATCTCCGGATATTCTTGTAGTCGGAAAAAGACCTGGCGAAAAGCTT  464420

Query  533     CACGAGGAGCTCACATTTCCGCACGAAGCAGATGCACTGTTTGAACATGAACAATTTTAT  592
               ||||||||||||||||||||||||||||||||||||||||||||||||||||||||||||
Sbjct  464419  CACGAGGAGCTCACATTTCCGCACGAAGCAGATGCACTGTTTGAACATGAACAATTTTAT  464360

Query  593     GCCATTTT  600
               ||||||||
Sbjct  464359  GCCATTTT  464352
```

Figure 2

1) REP-derived Splice Donor CTTCAGCCAGgtacatggag
2) Beta-Actin Splice Donor GTGGATCCAGgtgggtgtc
3) Beta-Actin Splice Acceptor ccctcctcagGAGGACCAG

SYNTHETIC GENETIC ELEMENTS FOR BIOMANUFACTURE

This application claims the benefit of U.S. Provisional Application No. 62/877,508 filed Jul. 23, 2019; U.S. Provisional Application No. 62/877,516 filed Jul. 23, 2019; U.S. Provisional Application No. 62/877,524 filed Jul. 23, 2019; U.S. Provisional Application No. 62/877,532 filed Jul. 23, 2019; U.S. Provisional Application No. 62/877,540 filed Jul. 23, 2019; U.S. Provisional Application No. 62/877,551 filed Jul. 23, 2019; U.S. Provisional Application No. 62/877,561 filed Jul. 23, 2019; and U.S. Provisional Application No. 62/877,577 filed Jul. 23, 2019, which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "14620-192-999_SEQ_LISTING" and a creation date of Jul. 20, 2020 and having a size of 152,403 bytes. The sequence listing submitted via EFS-Web is part of the specification and is herein incorporated by reference in its entirety.

BACKGROUND

Adeno-Associated Virus (AAV) has a linear single-stranded DNA (ssDNA) genome with two inverted terminal repeats (ITR) at the termini. The ITRs flank the two viral genes—rep (replication) and cap (capsid), which encode non-structural and structural proteins, respectively. The rep gene encodes four regulatory proteins Rep78, Rep68, Rep52 and Rep40, through the use of two promoters and alternative splicing. More specifically, Rep78 and Rep68 are transcribed from the P5 promoter and Rep 40 and Rep52 are transcribed from the P19 promoter (which is embedded within the Rep78 and Rep68 reading frame). The P5 and P19 promoters are activated by the adenovirus E1A gene and are active in cells such as HEK293 that was transformed using the adenovirus E1 genes. These Rep proteins are involved in AAV genome replication. The cap gene, through alternative splicing and initiation of translation, gives rise to three capsid proteins, VP1 (virion protein 1), VP2 and VP3, which assemble into a near-spherical protein shell of the virus. The AAV virus does not encode a polymerase, thus relying on cellular polymerases for genome replication.

Large-scale production of AAV in mammalian cells may be possible if the AAV rep and cap genes could be stably integrated or maintained in the cells and later induced to produce AAV in high density cultures. However, the expression of Rep proteins can be cytotoxic or cytostatic to the host cells, making it difficult to develop stable cell lines in hosts where rep genes are expressed such as those that express the Adenovirus E1 genes such as HEK293 cells. Because AAV encodes four Rep proteins with overlapping reading frames that result from the use of two promoters and alternate splicing, the use of an inducible promoter to control rep gene expression is not straightforward.

The cytotoxic or cytostatic nature of the four Rep proteins has prevented the development of stable cell lines that can produce high-titer AAV using native rep/cap promoters (Clark et al. (1995) Hum. Gene Ther. 6:1329-1341; Chadeuf et al. (2000) J. Gene med. 2:260-268). Several groups have attempted to regulate Rep expression recombinantly. Yang replaced the P5 promoter with the mouse metallothionein promoter. While stable clones in HEK293 demonstrated metal-inducible rep78 expression, rep50 and rep42 expression (driven by the internal P19 promoter) was only detected at low levels and the growth rate of the cells was substantially decreased (Yang et al. (1994) J. Virol 68: 4847-4856). Ogasawara replaced the P5 promoter with a ubiquitous promoter containing a loxP flanked stuffer that could be activated by Cre recombinase. Neither rep52, rep40, or cap genes were induced in stable clones infected with Adenovirus-Cre, which suggested constitutive rep521rep40 expression was also harmful to cells (Ogasawara et al. (1999) J. Gen. Virol. 80: 2477-2480).

Another approach to regulated rep expression was described by Xiao and coworkers (Qiao et al. (2002) J. Virol. 76: 13015-13027; Yuan et al. (2011) Hum. Gene Ther. 22:613-624). Xiao inserted an artificial intron into the rep gene in a coding region all four Rep proteins share and inserted a loxP flanked stop cassette containing the poly(A) sequences alone or in combination with puro, the puromycin resistance gene, into the intron. Expression of all the Rep proteins is inhibited, allowing stable cell lines in HEK293 cells to be generated. Delivery of Cre recombinase (by adenovirus infection) into the cell excises the stop cassette through recombining the loxP sites, allowing full length pre-mRNA to be transcribed. The remaining intron sequence is then precisely removed by RNA splicing, restoring the coding sequence for all four Rep proteins, and, thus, initiating the production of AAV from an integrated ITR-flanked transgene. However, because Cre recombinase recognizes two identical loxP sites, the loxP sites remain identical after recombination, thus additional recombination may be possible since Cre catalyzes both joining and excision reactions.

AAV rep genes are only expressed in cells that also express the adenovirus E1 (Early region 1) genes. Several stable rep/cap cell lines have been constructed in hosts that do not express the E1 genes including HeLa (Clark et al (1995) Hum. Gen. Therap. 6: 1329-1341; Yang et al. (1994) J. Virol. 68: 4847-4856; Gao et. Al (1998) Hu, Gen. Ther. 9: 2353-2362), A549 (Gao et al. (2002) Mol Ther. 5:644-659), and Vero (Beal et al. $(2007)_{10}$th Annual Meeting of American Society of Gene Therapy, Seattle, WA, May30-Jun. 3, 2007). The largest drawback to these cell lines is that an E1-intact (and usually replication competent) adenovirus is required for AAV production, which may pose increased safety risks as a contaminant of AAV virus preps.

AAV production systems have been described using several different viruses to provide helper functions and to deliver the recombinant transgene and/or AAV genes to human cells including Herpes (Thomas et al. (2009) Hum Gene Ther. 20:861-70; Clement et al. (2009) Hum Gene Ther. 20:796-806), Vaccinia virus (Wang et al. (2017) Mol. Ther. Methods Clin Devel. 7: 146-155.), and Adenovirus (Fisher et al. (1996) Hum gene Ther. 7: 2079-2087; Gao et al. (1998) Hum Gene Ther. 2353-2362. Liu et al. (1999) Gene Ther 6: 293-299). These approaches require production of several different viruses (and in some cases recombinant host cell lines). AAV has also been produced in insect cells using baculoviruses (Mietzsch et al. (2014) Hum Gene Ther. 25:212-22; Aslanidi et al. (2009) Proc Natl Acad Sci USA. 106:5059-5064; Cecchini et al. (2011) Hum Gene Ther. 22:1021-1030). Whether AAVs produced in insect versus human cells are functionally equivalent is still an open question.

There is a need for improved production of AAVs with recombinant constructs and cells.

SUMMARY

In one aspect, provided herein is a non-naturally occurring nucleic acid molecule comprising a modified adeno-associated virus (AAV) rep gene having an AAV rep gene encoding four Rep proteins Rep78, Rep68, Rep52 and Rep40 and an artificial intron inserted into a coding sequence of the rep gene shared by the four Rep proteins, wherein the artificial intron comprises a stop cassette inserted downstream of the 5' splice site and upstream of the branch site of the artificial intron, and the stop cassette comprises, in 5' to 3' order: (a) an attP site having a nucleotide sequence at least 90%, 91%, 92%, 93%, 94%, 95%, 96%, 97%, 98%, 99% or 100%, identical to SEQ ID NO:7, preferably, an attP site having the nucleotide sequence of SEQ ID NO:7; (b) a splice acceptor; (c) a terminator; and (d) an attB site having a nucleotide sequence at least 90%, 91%, 92%, 93%, 94%, 95%, 96%, 97%, 98%, 99% or 100%, identical of SEQ ID NO:8 or SEQ ID NO:9, preferably, an attB site having the nucleotide sequence of SEQ ID NO:8 or SEQ ID NO:9.

In one embodiment, the splice acceptor comprises the nucleotide sequence of SEQ ID NO:17.

In one embodiment, the terminator comprises a polyadenylation signal. In one embodiment, the terminator further comprises the nucleotide sequence of SEQ ID NO:19.

In one embodiment, the stop cassette comprises a gene encoding a selectable marker, preferably a neomycin phosphotransferase expression cassette having the nucleotide sequence of SEQ ID NO:18.

In one embodiment, the artificial intron comprises, in 5' to 3' order, the nucleotide sequence of SEQ ID NO:14, the stop cassette, and the nucleotide sequence of SEQ ID NO:15.

In one embodiment, the AAV rep gene comprises a rep gene of one of AAV1 to AAV8, or a hybrid thereof. In one embodiment, the AAV rep gene comprises the rep gene of human AAV2 having nucleotide numbers 190 to 2202 of the nucleotide sequence of GenBank accession number NC_001401.2. In one embodiment, the artificial intron is inserted between nucleotide numbers 996 to 1905 of the nucleotide sequence of GenBank accession number NC_001401.2. In one embodiment, the artificial intron is inserted immediately downstream of nucleotide number 1052, 1061, 1712, 1906, 1022, 1112, 1475, 1514, 1700, 1742, 1784 or 1340, preferably nucleotide number 1052, of the nucleotide sequence of GenBank accession number NC_001401.2.

In one aspect, provided herein is a non-naturally occurring nucleic acid molecule comprising a modified AAV rep gene comprising, in 5' to 3' order: (a) a 5' portion of an AAV rep gene having the nucleotide sequence of SEQ ID NO:55; (b) an artificial intron comprising, in 5' to 3' order: (i) a 5' intron fragment having the nucleotide sequence of SEQ ID NO:14; (ii) a stop cassette comprising, in 5' to 3' order: (1) an attP site having the nucleotide sequence of SEQ ID NO:7; (2) a splice acceptor having the nucleotide sequence of SEQ ID NO:17; (3) a neomycin phosphotransferase expression cassette having the nucleotide sequence of SEQ ID NO:18; (4) a terminator having the nucleotide sequence of SEQ ID NO:19; and (5) an attB site having the nucleotide sequence of SEQ ID NO:8 or SEQ ID NO:9; and (iii) a 3' intron fragment having the nucleotide sequence of SEQ ID NO:15; and (c) a 3' portion of the AAV rep gene having the nucleotide sequence of SEQ ID NO:56.

In one aspect, provided herein is a non-naturally occurring nucleic acid molecule comprising a modified AAV rep gene comprising, in 5' to 3' order: (a) a 5' portion of an AAV rep gene having the nucleotide sequence of SEQ ID NO:73; (b) an artificial intron comprising, in 5' to 3' order: (i) a 5' intron fragment having the nucleotide sequence of SEQ ID NO:14; (ii) a stop cassette comprising, in 5' to 3' order: (1) an attP site having the nucleotide sequence of SEQ ID NO:7; (2) a splice acceptor having the nucleotide sequence of SEQ ID NO:17; (3) a neomycin phosphotransferase expression cassette having the nucleotide sequence of SEQ ID NO:18; (4) a terminator having the nucleotide sequence of SEQ ID NO:19; and (5) an attB site having the nucleotide sequence of SEQ ID NO:8 or SEQ ID NO:9; and (iii) a 3' intron fragment having the nucleotide sequence of SEQ ID NO:66; and (c) a 3' portion of the AAV rep gene having the nucleotide sequence of SEQ ID NO:56. In one embodiment, the stop cassette comprises the nucleotide sequence of SEQ ID NO:16.

In one embodiment, the non-naturally occurring nucleic acid molecule further includes an AAV cap gene encoding three capsid proteins VP1, VP2 and VP3. In one embodiment, the AAV cap gene comprises a cap gene of one of AAV1 to AAV9 and AAVDJ, or a hybrid thereof. In one embodiment, the AAV cap gene comprises the cap gene of human AAV9 having the nucleotide sequence of GenBank accession number AY530579.1. In one embodiment, the AAV cap gene further comprises a polyadenylation signal, preferably a polyadenylation signal of AAV2 having nucleotide numbers 4411 to 4466 of the nucleotide sequence of GenBank accession number NC_001401.2, and an enhancer, preferably an AAV2 rep P5 promoter having nucleotide numbers 190 to 313 of the nucleotide sequence of GenBank accession number NC_001401.2, wherein the polyadenylation signal and the enhancer are both downstream of the coding sequence of the cap gene. In one embodiment, the non-naturally occurring nucleic acid molecule further includes a transgene flanked by a pair of AAV inverted terminal repeats (ITRs) downstream of the AAV cap gene.

In one embodiment, the non-naturally occurring nucleic acid molecule still further includes a first insulator upstream of the modified AAV rep gene and optionally a second insulator downstream of the transgene flanked by the ITRs, preferably, the first insulator and the second insulator are independently selected from the group consisting of: (a) a human anti-repressor element 40 having the nucleotide sequence of SEQ ID NO:24; (b) a mouse anti-repressor element 40 having the nucleotide sequence of SEQ ID NO:25; (c) an anti-repressor element 04 having the nucleotide sequence of GenBank accession number AY190749.1; (d) an anti-repressor element 06 having the nucleotide sequence of GenBank accession number AY190750.1; (e) an anti-repressor element 07 having the nucleotide sequence of GenBank accession number AY190751.1; (f) an anti-repressor element 12 having the nucleotide sequence of GenBank accession number AY190752.1; (g) an anti-repressor element 13 having the nucleotide sequence of GenBank accession number AY190753.1; (h) an anti-repressor element 35 having the nucleotide sequence of GenBank accession number AY190754.1; (i) an anti-repressor element 36 having the nucleotide sequence of GenBank accession number AY190755.1; (j) an anti-repressor element 52 having the nucleotide sequence of GenBank accession number AY190757.1; (k) an anti-repressor element 53 having the nucleotide sequence of GenBank accession number AY190758.1; and (1) a Chicken HS4 insulator from the globin locus having the nucleotide sequence of AY040835.1 in two or more copies, more preferably, the first insulator and the second insulator have the nucleotide sequences of SEQ ID NO:24 and SEQ ID NO:25, respectively. In one embodiment, the non-naturally occurring nucleic acid molecule comprises the first insulator upstream of the modified AAV rep gene, and further comprises a first spacer sequence and a second spacer sequence upstream and downstream of the transgene, respectively, wherein the first spacer sequence and the second spacer sequence are independently selected from the group consisting of: (a) a nucleotide sequence of SEQ ID NO:67; and (b) a nucleotide sequence of SEQ ID NO:68. In one embodiment, the ITR has the nucleotide sequence of SEQ ID NO:20, the transgene comprises a promoter operably linked to a coding sequence, and the coding sequence is operably linked a polyadenylation signal; preferably, the promoter has the nucleotide sequence of SEQ ID NO:21 and the polyadenylation signal has the nucleotide sequence SEQ ID NO:23.

In one aspect, provided herein is a non-naturally occurring nucleic acid molecule comprising, in 5' to 3' order: (A) a first insulator, preferably the first insulator has the nucleotide sequence of SEQ ID NO:24; (B) a modified AAV rep gene comprising, in 5' to 3' order: (i) a 5' portion of an AAV rep gene, preferably the 5' portion of the AAV rep gene has the nucleotide sequence of SEQ ID NO:55; (ii) an artificial intron comprising, in 5' to 3' order: (a) a 5' intron fragment, preferably the 5' intron fragment has the nucleotide sequence of SEQ ID NO:14; (b) a stop cassette comprising, in 5' to 3' order: (1) an attP site having the nucleotide sequence of SEQ ID NO:7; (2) a splice acceptor, preferably the splice acceptor has the nucleotide sequence of SEQ ID NO:17; (3) a gene encoding a selectable marker, preferably a neomycin phosphotransferase expression cassette having the nucleotide sequence of SEQ ID NO:18; (4) a terminator, preferably the terminator has the nucleotide sequence of SEQ ID NO:19; and (5) an attB site having the nucleotide sequence of SEQ ID NO:8 or SEQ ID NO:9; and (c) a 3' intron fragment, preferably the 3' intron fragment has the nucleotide sequence of SEQ ID NO:15; (iii) a 3' portion of the AAV rep gene, preferably the 3' portion of the AAV rep gene has the nucleotide sequence of SEQ ID NO:56; (C) an AAV cap gene, preferably the AAV cap gene comprises the nucleotide sequence of SEQ ID NO:57; (D) a transgene flanked by a pair of AAV ITRs, preferably, the AAV ITR has the nucleotide sequence of SEQ ID NO:20, and the transgene comprises a promoter operably linked to a coding sequence, and the coding sequence is operably linked a polyadenylation signal; more preferably, the promoter has the nucleotide sequence of SEQ ID NO:21 and the polyadenylation signal has the nucleotide sequence SEQ ID NO:23; and (E) a second insulator, preferably the second insulator has the nucleotide sequence of SEQ ID NO:25.

In one aspect, provided herein is a non-naturally occurring nucleic acid molecule comprising, in 5' to 3' order: (A) a first insulator, preferably the first insulator has the nucleotide sequence of SEQ ID NO:24; (B) a modified AAV rep gene comprising, in 5' to 3' order: (i) a 5' portion of an AAV rep gene, preferably the 5' portion of the AAV rep gene has the nucleotide sequence of SEQ ID NO:73; (ii) an artificial intron comprising, in 5' to 3' order: (a) a 5' intron fragment, preferably the 5' intron fragment has the nucleotide sequence of SEQ ID NO:14; (b) a stop cassette comprising, in 5' to 3' order: (1) an attP site having the nucleotide sequence of SEQ ID NO:7; (2) a splice acceptor, preferably the splice acceptor has the nucleotide sequence of SEQ ID NO:17; (3) a gene encoding a selectable marker, preferably a neomycin phosphotransferase expression cassette having the nucleotide sequence of SEQ ID NO:18; (4) a terminator, preferably the terminator has the nucleotide sequence of SEQ ID NO:19; and (5) an attB site having the nucleotide sequence of SEQ ID NO:8 or SEQ ID NO:9; and (c) a 3' intron fragment, preferably the 3' intron fragment has the nucleotide sequence of SEQ ID NO:66; (iii) a 3' portion of the AAV rep gene, preferably the 3' portion of the AAV rep gene has the nucleotide sequence of SEQ ID NO:56; (C) an AAV cap gene; (D) a transgene flanked by (1) a pair of AAV ITRs, preferably, the AAV ITR has the nucleotide sequence of SEQ ID NO:20, and the transgene comprises a promoter operably linked to a coding sequence, and the coding sequence is operably linked a polyadenylation signal; more preferably, the promoter has the nucleotide sequence of SEQ ID NO:21 and the polyadenylation signal has the nucleotide sequence SEQ ID NO:23; and (2) a pair of spacer sequences, preferably, the spacer sequences have a nucleotide sequence of SEQ ID NO:67 and SEQ ID NO:68.

In one aspect, provided herein is a vector comprising a non-naturally occurring nucleic acid molecule described above; preferably, the vector is a plasmid; more preferably, the plasmid comprises the nucleotide sequence of SEQ ID NO:12.

In one aspect, provided herein is a vector comprising a non-naturally occurring nucleic acid molecule described above; preferably, the vector is a plasmid; more preferably, the plasmid comprises the nucleotide sequence of SEQ ID NO:70.

In one aspect, provided herein is a method of making the non-naturally occurring nucleic acid molecule of described above. In specific embodiments, provided herein is a method of making the vector comprising a non-naturally occurring nucleic acid molecule described above; preferably, the vector is a plasmid; more preferably, the plasmid comprises the nucleotide sequence of SEQ ID NO:12. In another embodiment, provided herein is a method of making the vector comprising a non-naturally occurring nucleic acid molecule described above; preferably, the vector is a plasmid; more preferably, the plasmid comprises the nucleotide sequence of SEQ ID NO:70.

In one aspect, provided herein is a cell comprising a non-naturally occurring nucleic acid molecule comprising a modified adeno-associated virus (AAV) rep gene having an AAV rep gene encoding four Rep proteins Rep78, Rep68, Rep52 and Rep40 and an artificial intron inserted into a coding sequence of the rep gene shared by the four Rep proteins, wherein the artificial intron comprises a stop cassette inserted downstream of the 5' splice site and upstream of the branch site of the artificial intron, and the stop cassette comprises, in 5' to 3' order: (a) an attP site having a nucleotide sequence at least 90%, 91%, 92%, 93%, 94%, 95%, 96%, 97%, 98%, 99% or 100%, identical to SEQ ID NO:7, preferably, an attP site having the nucleotide sequence of SEQ ID NO:7; (b) a splice acceptor; (c) a terminator; and (d) an attB site having a nucleotide sequence at least 90%, 91%, 92%, 93%, 94%, 95%, 96%, 97%, 98%, 99% or 100%, identical of SEQ ID NO:8 or SEQ ID NO:9, preferably, an attB site having the nucleotide sequence of SEQ ID NO:8 or SEQ ID NO:9.

In one embodiment, the splice acceptor comprises the nucleotide sequence of SEQ ID NO:17.

In one embodiment, the terminator comprises a polyadenylation signal. In one embodiment, the terminator further comprises the nucleotide sequence of SEQ ID NO:19.

In one embodiment, the stop cassette comprises a gene encoding a selectable marker, preferably a neomycin phosphotransferase expression cassette having the nucleotide sequence of SEQ ID NO:18.

In one embodiment, the artificial intron comprises, in 5' to 3' order, the nucleotide sequence of SEQ ID NO:14, the stop cassette, and the nucleotide sequence of SEQ ID NO:15. In another embodiment, the artificial intron comprises, in 5' to 3' order, the nucleotide sequence of SEQ ID NO:14, the stop cassette, and the nucleotide sequence of SEQ ID NO:66.

In one embodiment, the AAV rep gene comprises a rep gene of one of AAV1 to AAV8, or a hybrid thereof. In one embodiment, the AAV rep gene comprises the rep gene of human AAV2 having nucleotide numbers 190 to 2202 of the nucleotide sequence of GenBank accession number NC_001401.2. In one embodiment, the artificial intron is inserted between nucleotide numbers 996 to 1905 of the nucleotide sequence of GenBank accession number NC_001401.2. In one embodiment, the artificial intron is inserted immediately downstream of nucleotide number 1052, 1061, 1712, 1906, 1022, 1112, 1475, 1514, 1700, 1742, 1784 or 1340, preferably nucleotide number 1052, of the nucleotide sequence of GenBank accession number NC_001401.2.

In one aspect, provided herein is a cell comprising a non-naturally occurring nucleic acid molecule comprising a modified AAV rep gene comprising, in 5' to 3' order: (a) a 5' portion of an AAV rep gene having the nucleotide sequence of SEQ ID NO:55; (b) an artificial intron comprising, in 5' to 3' order: (i) a 5' intron fragment having the nucleotide sequence of SEQ ID NO:14; (ii) a stop cassette comprising, in 5' to 3' order: (1) an attP site having the nucleotide sequence of SEQ ID NO:7; (2) a splice acceptor having the nucleotide sequence of SEQ ID NO:17; (3) a neomycin phosphotransferase expression cassette having the nucleotide sequence of SEQ ID NO:18; (4) a terminator having the nucleotide sequence of SEQ ID NO:19; and (5) an attB site having the nucleotide sequence of SEQ ID NO:8 or SEQ ID NO:9; and (iii) a 3' intron fragment having the nucleotide sequence of SEQ ID NO:15; and (c) a 3' portion of the AAV rep gene having the nucleotide sequence of SEQ ID NO:56.

In one aspect, provided herein is a cell comprising a non-naturally occurring nucleic acid molecule comprising a modified AAV rep gene comprising, in 5' to 3' order: (a) a 5' portion of an AAV rep gene having the nucleotide sequence of SEQ ID NO:73; (b) an artificial intron comprising, in 5' to 3' order: (i) a 5' intron fragment having the nucleotide sequence of SEQ ID NO:14; (ii) a stop cassette comprising, in 5' to 3' order: (1) an attP site having the nucleotide sequence of SEQ ID NO:7; (2) a splice acceptor having the nucleotide sequence of SEQ ID NO:17; (3) a neomycin phosphotransferase expression cassette having the nucleotide sequence of SEQ ID NO:18; (4) a terminator having the nucleotide sequence of SEQ ID NO:19; and (5) an attB site having the nucleotide sequence of SEQ ID NO:8 or SEQ ID NO:9; and (iii) a 3' intron fragment having the nucleotide sequence of SEQ ID NO:66; and (c) a 3' portion of the AAV rep gene having the nucleotide sequence of SEQ ID NO:56.

In one embodiment, the stop cassette comprises the nucleotide sequence of SEQ ID NO:16.

In one embodiment, the cell described above further includes an AAV cap gene encoding three capsid proteins VP1, VP2 and VP3. In one embodiment, the AAV cap gene comprises a cap gene of one of AAV1 to AAV9 and AAVDJ, or a hybrid thereof. In one embodiment, the AAV cap gene comprises the cap gene of human AAV9 having the nucleotide sequence of GenBank accession number AY530579.1. In one embodiment, the AAV cap gene comprises the cap gene of a hybrid of AAV9.

In one embodiment, the AAV cap gene further comprises a polyadenylation signal, preferably a polyadenylation signal of AAV2 having nucleotide numbers 4411 to 4466 of the nucleotide sequence of GenBank accession number NC_001401.2, and an enhancer, preferably an AAV2 rep P5 promoter having nucleotide numbers 190 to 313 of the nucleotide sequence of GenBank accession number NC_001401.2, wherein the polyadenylation signal and the enhancer are both downstream of the coding sequence of the cap gene.

In one embodiment, the cell comprising a cap gene further includes a transgene flanked by a pair of AAV inverted terminal repeats (ITRs) downstream of the AAV cap gene. In one embodiment, the cell further includes a first insulator upstream of the modified AAV rep gene and optionally a second insulator downstream of the transgene flanked by the ITRs, preferably, the first insulator and the second insulator are independently selected from the group consisting of: (a) a human anti-repressor element 40 having the nucleotide sequence of SEQ ID NO:24; (b) a mouse anti-repressor element 40 having the nucleotide sequence of SEQ ID NO:25; (c) an anti-repressor element 04 having the nucleotide sequence of GenBank accession number AY190749.1; (d) an anti-repressor element 06 having the nucleotide sequence of GenBank accession number AY190750.1; (e) an anti-repressor element 07 having the nucleotide sequence of GenBank accession number AY190751.1; (f) an anti-repressor element 12 having the nucleotide sequence of GenBank accession number AY190752.1; (g) an anti-repressor element 13 having the nucleotide sequence of GenBank accession number AY190753.1; (h) an anti-repressor element 35 having the nucleotide sequence of GenBank accession number AY190754.1; (i) an anti-repressor element 36 having the nucleotide sequence of GenBank accession number AY190755.1; (j) an anti-repressor element 52 having the nucleotide sequence of GenBank accession number AY190757.1; (k) an anti-repressor element 53 having the nucleotide sequence of GenBank accession number AY190758.1; and (l) a Chicken HS4 insulator from the globin locus having the nucleotide sequence of AY040835.1 in two or more copies, more preferably, the first insulator and the second insulator have the nucleotide sequences of SEQ ID NO:24 and SEQ ID NO:25, respectively. In one embodiment, the cell comprises the first insulator upstream of the modified AAV rep gene, and further comprises a first spacer sequence and a second spacer sequence upstream and downstream of the transgene, respectively, wherein the first spacer sequence and the second spacer sequence are independently selected from the group consisting of: (a) a nucleotide sequence of SEQ ID NO:67; and (b) a nucleotide sequence of SEQ ID NO:68.

In one embodiment, the ITR has the nucleotide sequence of SEQ ID NO:20, the transgene comprises a promoter operably linked to a coding sequence, and the coding sequence is operably linked a polyadenylation signal; preferably, the promoter has the nucleotide sequence of SEQ ID NO:21 and the polyadenylation signal has the nucleotide sequence SEQ ID NO:23.

In one aspect, provided herein is a cell comprising a non-naturally occurring nucleic acid molecule comprising, in 5' to 3' order: (A) a first insulator, preferably the first insulator has the nucleotide sequence of SEQ ID NO:24; (B) a modified AAV rep gene comprising, in 5' to 3' order: (i) a 5' portion of an AAV rep gene, preferably the 5' portion of the AAV rep gene has the nucleotide sequence of SEQ ID NO:55; (ii) an artificial intron comprising, in 5' to 3' order: (a) a 5' intron fragment, preferably the 5' intron fragment has the nucleotide sequence of SEQ ID NO:14; (b) a stop cassette comprising, in 5' to 3' order: (1) an attP site having the nucleotide sequence of SEQ ID NO:7; (2) a splice acceptor, preferably the splice acceptor has the nucleotide sequence of SEQ ID NO:17; (3) a gene encoding a selectable marker, preferably a neomycin phosphotransferase expression cassette having the nucleotide sequence of SEQ ID NO:18; (4) a terminator, preferably the terminator has the nucleotide sequence of SEQ ID NO:19; and (5) an attB site having the nucleotide sequence of SEQ ID NO:8 or SEQ ID NO:9; and (c) a 3' intron fragment, preferably the 3' intron fragment has the nucleotide sequence of SEQ ID NO:15; (iii) a 3' portion of the AAV rep gene, preferably the 3' portion of the AAV rep gene has the nucleotide sequence of SEQ ID NO:56; (C) an AAV cap gene, preferably the AAV cap gene comprises the nucleotide sequence of SEQ ID NO:57; (D) a transgene flanked by a pair of AAV ITRs, preferably, the AAV ITR has the nucleotide sequence of SEQ ID NO:20, and the transgene comprises a promoter operably linked to a coding sequence, and the coding sequence is operably linked a polyadenylation signal; more preferably, the promoter has the nucleotide sequence of SEQ ID NO:21 and the polyadenylation signal has the nucleotide sequence SEQ ID NO:23; and (E) a second insulator, preferably the second insulator has the nucleotide sequence of SEQ ID NO:25.

In one aspect, provided herein is a cell comprising a non-naturally occurring nucleic acid molecule comprising, in 5' to 3' order: (A) a first insulator, preferably the first insulator has the nucleotide sequence of SEQ ID NO:24; (B) a modified AAV rep gene comprising, in 5' to 3' order: (i) a 5' portion of an AAV rep gene, preferably the 5' portion of the AAV rep gene has the nucleotide sequence of SEQ ID NO:73; (ii) an artificial intron comprising, in 5' to 3' order: (a) a 5' intron fragment, preferably the 5' intron fragment has the nucleotide sequence of SEQ ID NO:14; (b) a stop cassette comprising, in 5' to 3' order: (1) an attP site having the nucleotide sequence of SEQ ID NO:7; (2) a splice acceptor, preferably the splice acceptor has the nucleotide sequence of SEQ ID NO:17; (3) a gene encoding a selectable marker, preferably a neomycin phosphotransferase expression cassette having the nucleotide sequence of SEQ ID NO:18; (4) a terminator, preferably the terminator has the nucleotide sequence of SEQ ID NO:19; and (5) an attB site having the nucleotide sequence of SEQ ID NO:8 or SEQ ID NO:9; and (c) a 3' intron fragment, preferably the 3' intron fragment has the nucleotide sequence of SEQ ID NO:66; (iii) a 3' portion of the AAV rep gene, preferably the 3' portion of the AAV rep gene has the nucleotide sequence of SEQ ID NO:56; (C) an AAV cap gene; and (D) a transgene flanked by (i) a pair of AAV ITRs, preferably, the AAV ITR has the nucleotide sequence of SEQ ID NO:20, and the transgene comprises a promoter operably linked to a coding sequence, and the coding sequence is operably linked a polyadenylation signal; more preferably, the promoter has the nucleotide sequence of SEQ ID NO:21 and the polyadenylation signal has the nucleotide sequence SEQ ID NO:23; and (ii) a pair of spacer sequences, preferably, the spacer sequences have a nucleotide sequence of SEQ ID NO:67 and SEQ ID NO:68.

In one embodiment, the non-naturally occurring nucleic acid molecule is episomal, having the nucleotide sequence of SEQ ID NO:12. In another embodiment, the non-naturally occurring nucleic acid molecule is episomal, having the nucleotide sequence of SEQ ID NO:70.

In one embodiment, the cell further includes a nucleic acid molecule encoding a recombinase having the amino acid sequence at least 85%, 86%, 87%, 88%, 89%, 90%, 91%, 92%, 93%, 94%, 95%, 96%, 97%, 98%, 99%, or 100% identical to the amino acid sequence of SEQ ID NO:2; preferably, the nucleic acid comprises the nucleotide sequence at least 85%, at least 85%, 86%, 87%, 88%, 89%, 90%, 91%, 92%, 93%, 94%, 95%, 96%, 97%, 98%, 99%, or 100% identical to the nucleotide sequence of SEQ ID NO:3; more preferably, the cell comprises a recombinant ΔE1/ΔE3 adenovirus serotype 5 (Ad5) virus encoding the recombinase having the amino acid sequence of SEQ ID NO:2.

In one embodiment, the cell further includes adenovirus E1A and E1B genes, preferably the cell is a 911 cell, a pTG6559 cell, a GH329 cell, a N52.E6 cell, a HeLa-E1 cell, an UR cell, a VLI-293 cell, a HEK293 cell, or a PER.C6 cell.

In one aspect, provided herein is a method of producing a recombinant AAV comprising a transgene, comprising: (A) obtaining a first host cell comprising: (i) a modified AAV rep gene comprising, in 5' to 3' order: (a) a 5' portion of an AAV rep gene, preferably the AAV rep gene has the nucleotide sequence of SEQ ID NO:55; (b) an artificial intron comprising, in 5' to 3' order: (1) a 5' intron fragment, preferably the 5' intron fragment has the nucleotide sequence of SEQ ID NO:14; (2) a stop cassette comprising, in 5' to 3' order: (aa) an attP site having the nucleotide sequence of SEQ ID NO:7; (bb) a splice acceptor, preferably the splice acceptor has the nucleotide sequence of SEQ ID NO:17; (cc) a gene encoding a selectable marker, preferably a neomycin phosphotransferase expression cassette having the nucleotide sequence of SEQ ID NO:18; (dd) a terminator, preferably the terminator has the nucleotide sequence of SEQ ID NO:19; and (ee) an attB site having the nucleotide sequence of SEQ ID NO:8 or SEQ ID NO:9; and (3) a 3' intron fragment, preferably the 3' intron fragment has the nucleotide sequence of SEQ ID NO:15; (c) a 3' portion of the AAV rep gene, preferably the 3' portion of the AAV rep gene has the nucleotide sequence of SEQ ID NO:56; (ii) an AAV cap gene, preferably the AAV cap gene comprises the nucleotide sequence of SEQ ID NO:57; and (iii) the transgene flanked by a pair of AAV ITRs, preferably, the ITR has the nucleotide sequence of SEQ ID NO:20, the transgene comprises a promoter operably linked to a coding sequence, and the coding sequence is operably linked a polyadenylation signal; more preferably, the promoter has the nucleotide sequence of SEQ ID NO:21 and the polyadenylation signal has the nucleotide sequence SEQ ID NO:23; (B) infecting the first host cell with a recombinant adenovirus comprising a recombinase gene encoding a recombinase having at least 85%, 86%, 87%, 88%, 89%, 90%, 91%, 92%, 93%, 94%, 95%, 96%, 97%, 98%, 99%, or 100%, sequence identity to the amino acid sequence of SEQ ID NO:2 to obtain a second host cell further containing the recombinase gene; (C) growing the second host cell under conditions in which the recombinant AAV comprising the transgene is produced; and (D) optionally collecting the recombinant AAV.

In one aspect, provided herein is a method of producing a recombinant AAV comprising a transgene, comprising: (A) obtaining a first host cell comprising: (i) a modified AAV rep gene comprising, in 5' to 3' order: (a) a 5' portion of an AAV rep gene, preferably the AAV rep gene has the nucleotide sequence of SEQ ID NO:73; (b) an artificial intron comprising, in 5' to 3' order: (1) a 5' intron fragment, preferably the 5' intron fragment has the nucleotide sequence of SEQ ID NO:14; (2) a stop cassette comprising, in 5' to 3' order: (aa) an attP site having the nucleotide sequence of SEQ ID NO:7; (bb) a splice acceptor, preferably the splice acceptor has the nucleotide sequence of SEQ ID NO:17; (cc) a gene encoding a selectable marker, preferably a neomycin phosphotransferase expression cassette having the nucleotide sequence of SEQ ID NO:18; (dd) a terminator, preferably the terminator has the nucleotide sequence of SEQ ID NO:19; and (ee) an attB site having the nucleotide sequence of SEQ ID NO:8 or SEQ ID NO:9; and (3) a 3' intron fragment, preferably the 3' intron fragment has the nucleotide sequence of SEQ ID NO:66; (c) a 3' portion of the AAV rep gene, preferably the 3' portion of the AAV rep gene has the nucleotide sequence of SEQ ID NO:66; (ii) an AAV cap gene; and (iii) the transgene flanked by: (a) a pair of AAV ITRs, preferably, the ITR has the nucleotide sequence of SEQ ID NO:20, the transgene comprises a promoter operably linked to a coding sequence, and the coding sequence is operably linked a polyadenylation signal; more preferably, the promoter has the nucleotide sequence of SEQ ID NO:21 and the polyadenylation signal has the nucleotide sequence SEQ ID NO:23; and (b) a pair of spacer sequences, preferably, the spacer sequences have a nucleotide sequence of SEQ ID NO:67 and SEQ ID NO:68; (B) infecting the first host cell with a recombinant adenovirus comprising a recombinase gene encoding a recombinase having at least 85%, 86%, 87%, 88%, 89%, 90%, 91%, 92%, 93%, 94%, 95%, 96%, 97%, 98%, 99%, or 100%, sequence identity to the amino acid sequence of SEQ ID NO:2 to obtain a second host cell further containing the recombinase gene; (C) growing the second host cell under conditions in which the recombinant AAV comprising the transgene is produced; and (D) optionally collecting the recombinant AAV.

In one embodiment, the first host cell further comprises a first insulator upstream of the modified AAV rep gene and optionally a second insulator downstream of the transgene flanked by the ITRs, preferably, the first insulator and the second insulator are independently selected from the group consisting of: (a) a human anti-repressor element 40 having the nucleotide sequence of SEQ ID NO:24; (b) a mouse anti-repressor element 40 having the nucleotide sequence of SEQ ID NO:25; (c) an anti-repressor element 04 having the nucleotide sequence of GenBank accession number AY190749.1; (d) an anti-repressor element 06 having the nucleotide sequence of GenBank accession number AY190750.1; (e) an anti-repressor element 07 having the nucleotide sequence of GenBank accession number AY190751.1; (f) an anti-repressor element 12 having the nucleotide sequence of GenBank accession number AY190752.1; (g) an anti-repressor element 13 having the nucleotide sequence of GenBank accession number AY190753.1; (h) an anti-repressor element 35 having the nucleotide sequence of GenBank accession number AY190754.1; (i) an anti-repressor element 36 having the nucleotide sequence of GenBank accession number AY190755.1; (j) an anti-repressor element 52 having the nucleotide sequence of GenBank accession number AY190757.1; (k) an anti-repressor element 53 having the nucleotide sequence of GenBank accession number AY190758.1; and (1) a Chicken HS4 insulator from the globin locus having the nucleotide sequence of AY040835.1 in two or more copies, more preferably, the first insulator and the second insulator have the nucleotide sequences of SEQ ID NO:24 and SEQ ID NO:25, respectively.

In one embodiment, the first host cell comprises the first insulator upstream of the modified AAV rep gene, and further comprises a first spacer sequence and a second spacer sequence upstream and downstream of the transgene, respectively, wherein the first spacer sequence and the second spacer sequence are independently selected from the group consisting of: (a) a nucleotide sequence of SEQ ID NO:67; and (b) a nucleotide sequence of SEQ ID NO:68.

In one embodiment, the first host cell is obtained by introducing into a cell one or more nucleic acid molecules comprising the modified AAV rep gene, the AAV cap gene, the transgene flanked by the ITRs, the first insulator and the second insulator. In one embodiment, the first host cell is obtained by introducing into the cell a nucleic acid molecule comprising, in 5' to 3' order, the first insulator, the modified AAV rep gene, the AAV cap gene, the transgene flanked by the ITRs, the first insulator and the second insulator, preferably, a plasmid comprising the nucleotide sequence of SEQ ID NO:12.

In one embodiment, the first host cell is obtained by introducing into a cell one or more nucleic acid molecules comprising the modified AAV rep gene, the AAV cap gene, the transgene flanked by the ITRs, the first insulator, the first spacer sequence, and the second spacer sequence. In one embodiment, the first host cell is obtained by introducing into a cell one or more nucleic acid molecules comprising the modified AAV rep gene, the AAV cap gene, the transgene flanked by the ITRs, the first insulator, the first spacer sequence, and the second spacer sequencer, preferably, a plasmid comprising the nucleotide sequence of SEQ ID NO:70.

In one embodiment, the recombinant adenovirus is a recombinant ΔE1/ΔE3 adenovirus serotype 5 (Ad5) virus comprising a nucleotide sequence of SEQ ID NO:3.

In one embodiment, the host cell comprises adenovirus E1A and E1B genes, preferably the host cell is a 911 cell, pTG6559 cell, GH329 cell, N52.E6 cell, HeLa-E1 cell, UR cell, VLI-293 cell, HEK293 cell, or a PER.C6 cell.

In one embodiment, the conditions for growing the second host cell comprise culturing the second cell with 2-aminopurine. In one embodiment, the 2-aminopurine concentration is less than about 1.25 mM. In one embodiment, the 2-aminopurine concentration is about 1 μM to about 1.25 mM. In one embodiment, the 2-aminopurine concentration is about 10 μM to about 1.25 mM. In one embodiment, the 2-aminopurine concentration is about 100 μM to about 1.25 mM. In one embodiment, the 2-aminopurine concentration is about 1.25 mM.

In one embodiment, culturing the second cell with 2-aminopurine is initiated about 24 hours post-infection with the first host cell with a recombinant adenovirus.

In one aspect, provided herein is a composition comprising the cell comprising a nucleic acid molecule encoding a recombinase, as described above, and 2-aminopurine. In one embodiment, the 2-aminopurine concentration is less than about 1.25 mM. In one embodiment, the 2-aminopurine concentration is about 1 μM to about 1.25 mM. In one embodiment, the 2-aminopurine concentration is about 10 μM to about 1.25 mM. In one embodiment, the 2-aminopurine concentration is about 100 μM to about 1.25 mM. In one embodiment, the 2-aminopurine concentration is about 1.25 mM.

In one aspect, provided herein is a non-naturally occurring nucleic acid molecule comprising a nucleotide sequence encoding a serine recombinase having an amino acid sequence having at least 85%, 86%, 87%, 88%, 89%, 90%, 91%, 92%, 93%, 94%, 95%, 96%, 97%, 98%, 99% or 100%, identity to the amino acid sequence of SEQ ID NO:2. In one embodiment, the non-naturally occurring nucleic acid molecule includes a nucleotide sequence having at least 85%, 86%, 87%, 88%, 89%, 90%, 91%, 92%, 93%, 94%, 95%, 96%, 97%, 98%, 99% or 100%, identity to the nucleotide sequence of SEQ ID NO:3.

In one aspect, provided herein is a vector comprising the non-naturally occurring nucleic molecule comprising a nucleotide sequence encoding a serine recombinase having an amino acid sequence having at least 85%, 86%, 87%, 88%, 89%, 90%, 91%, 92%, 93%, 94%, 95%, 96%, 97%, 98%, 99% or 100%, identity to the amino acid sequence of SEQ ID NO:2.

In one aspect, provided herein is a vector comprising the non-naturally occurring nucleic molecule comprising a nucleotide sequence encoding a serine recombinase having an amino acid sequence having at least 85%, 86%, 87%, 88%, 89%, 90%, 91%, 92%, 93%, 94%, 95%, 96%, 97%, 98%, 99% or 100%, identity to the amino acid sequence of SEQ ID NO:3.

In one embodiment, the vector further includes a promoter, preferably a cytomegalovirus (CMV) promoter operably linked to the nucleotide sequence encoding the serine recombinase.

In one embodiment, the vector further includes a polyadenylation signal, such as a simian virus 40 (SV40) polyadenylation signal, operably linked to the nucleotide sequence encoding the serine recombinase.

In one embodiment, the vector is a DNA plasmid. In one embodiment, the vector is a recombinant adenoviral vector.

In one embodiment, the vector is a recombinant ΔE1/ΔE3 adenovirus serotype 5 (Ad5) virus comprising a nucleotide sequence encoding a serine recombinase having the amino acid sequence of SEQ ID NO:2 under the control of a CMV promoter, wherein the nucleotide sequence is further operably linked to a SV40 polyadenylation signal (NC_001669.1, nt 2550 to 2774).

In one aspect, provided herein is a cell comprising a non-naturally occurring nucleic acid molecule comprising a nucleotide sequence encoding a serine recombinase having an amino acid sequence having at least 85%, such as at least 85%, 86%, 87%, 88%, 89%, 90%, 91%, 92%, 93%, 94%, 95%, 96%, 97%, 98%, 99% or 100%, identity to the amino acid sequence of SEQ ID NO:2. In one embodiment, the cell includes a nucleotide sequence having at least 85%, such as at least 85%, 86%, 87%, 88%, 89%, 90%, 91%, 92%, 93%, 94%, 95%, 96%, 97%, 98%, 99% or 100%, identity to the nucleotide sequence of SEQ ID NO:3.

In one aspect, provided herein is a cell that includes the vector comprising the non-naturally occurring nucleic acid molecule comprising a nucleotide sequence encoding a serine recombinase having an amino acid sequence having at least 85%, such as at least 85%, 86%, 87%, 88%, 89%, 90%, 91%, 92%, 93%, 94%, 95%, 96%, 97%, 98%, 99% or 100%, identity to the amino acid sequence of SEQ ID NO:2. In another aspect, provided herein is a cell that includes the vector comprising the non-naturally occurring nucleic acid molecule comprising a nucleotide sequence encoding a serine recombinase having an amino acid sequence having at least 85%, such as at least 85%, 86%, 87%, 88%, 89%, 90%, 91%, 92%, 93%, 94%, 95%, 96%, 97%, 98%, 99% or 100%, identity to the amino acid sequence of SEQ ID NO:3.

In one embodiment, the cell further includes a promoter, preferably a cytomegalovirus (CMV) promoter operably linked to the nucleotide sequence encoding the serine recombinase.

In one embodiment, the cell further includes a polyadenylation signal, such as a simian virus 40 (SV40) polyadenylation signal, operably linked to the nucleotide sequence encoding the serine recombinase.

In one embodiment, the vector is a DNA plasmid. In one embodiment, the vector is a recombinant adenoviral vector.

In one embodiment, the recombinant adenoviral vector includes a recombinant ΔE1/ΔE3 adenovirus serotype 5 (Ad5) virus comprising a nucleotide sequence encoding a serine recombinase having the amino acid sequence of SEQ ID NO:2 under the control of a CMV promoter, wherein the nucleotide sequence is further operably linked to a SV40 polyadenylation signal (NC_001669.1, nt 2550 to 2774).

In one embodiment, the cell includes adenovirus ElA and E1B genes, preferably the cell is a 911 cell, pTG6559 cell, GH329 cell, N52.E6 cell, HeLa-E1 cell, UR cell, VLI-293 cell, HEK293 cell, or a PER.C6 cell.

In one aspect, provided herein is a method of conducting a site-specific recombination in a cell, comprising: (a) obtaining a cell comprising a nucleic acid molecule having an attP site having a nucleotide sequence at least 90%, 91%, 92%, 93%, 94%, 95%, 96%, 97%, 98%, 99% or 100%, identical to SEQ ID NO:7, preferably, an attP site having the nucleotide sequence of SEQ ID NO:7, and an attB site having a nucleotide sequence at least 90%, 91%, 92%, 93%, 94%, 95%, 96%, 97%, 98%, 99% or 100%, identical of SEQ ID NO:8 or SEQ ID NO:9, preferably, an attB site having the nucleotide sequence of SEQ ID NO:8 or SEQ ID NO:9; (b) introducing to the cell a non-naturally occurring nucleic acid molecule encoding a serine recombinase having at least 85%, 86%, 87%, 88%, 89%, 90%, 91%, 92%, 93%, 94%, 95%, 96%, 97%, 98%, 99% or 100% identity, to SEQ ID NO:2; and (c) growing the cell under conditions to allow the serine recombinase to catalyze the site-specific recombination between the attP and attB sites.

In one aspect, provided herein is a product produced by the process of conducting a site-specific recombination in a cell, comprising: (a) obtaining a cell comprising a nucleic acid molecule having an attP site having a nucleotide sequence at least 90%, 91%, 92%, 93%, 94%, 95%, 96%, 97%, 98%, 99% or 100%, identical to SEQ ID NO:7, preferably, an attP site having the nucleotide sequence of SEQ ID NO:7, and an attB site having a nucleotide sequence at least 90%, 91%, 92%, 93%, 94%, 95%, 96%, 97%, 98%, 99% or 100%, identical of SEQ ID NO:8 or SEQ ID NO:9, preferably, an attB site having the nucleotide sequence of SEQ ID NO:8 or SEQ ID NO:9; (b) introducing to the cell a non-naturally occurring nucleic acid molecule encoding a serine recombinase having at least 85%, 86%, 87%, 88%, 89%, 90%, 91%, 92%, 93%, 94%, 95%, 96%, 97%, 98%, 99% or 100% identity, to SEQ ID NO:2; and (c) growing the cell under conditions to allow the serine recombinase to catalyze the site-specific recombination between the attP and attB sites.

In one aspect, provided herein is a process for obtaining a product from a cell, comprising: (a) obtaining a cell comprising a nucleic acid molecule having an attP site having a nucleotide sequence at least 90%, 91%, 92%, 93%, 94%, 95%, 96%, 97%, 98%, 99% or 100%, identical to SEQ ID NO:7, preferably, an attP site having the nucleotide sequence of SEQ ID NO:7, and an attB site having a nucleotide sequence at least 90%, 91%, 92%, 93%, 94%, 95%, 96%, 97%, 98%, 99% or 100%, identical of SEQ ID NO:8 or SEQ ID NO:9, preferably, an attB site having the nucleotide sequence of SEQ ID NO:8 or SEQ ID NO:9; (b) introducing to the cell a non-naturally occurring nucleic acid molecule encoding a serine recombinase having at least 85%, 86%, 87%, 88%, 89%, 90%, 91%, 92%, 93%, 94%, 95%, 96%, 97%, 98%, 99% or 100% identity, to SEQ ID NO:2; (c) growing the cell under conditions to allow the serine recombinase to catalyze the site-specific recombination between the attP and attB sites; and (d) producing and recovering from the cell a product.

In one aspect, provided herein is a non-naturally occurring system, comprising: a means for AAV mediated recombination, wherein the means optionally comprises a transgenic element. In one aspect, provided herein is a means for transferring the non-naturally occurring system comprising: a means for AAV mediated recombination, wherein the means optionally comprises a transgenic element.

In one aspect, provided herein is a non-naturally occurring system, comprising: a recombination means for recombining the system of comprising: a means for AAV mediated recombination, wherein the means optionally comprises a transgenic element, wherein the recombination means includes using at least one serine residue during catalysis. In one aspect, provided herein is a means for transferring the non-naturally occurring system, comprising: a recombination means for recombining the system of comprising: a means for AAV mediated recombination, wherein the means optionally comprises a transgenic element, wherein the recombination means includes using at least one serine residue during catalysis.

In one aspect, provided herein is a means for manufacturing a molecule, wherein the means for manufacturing a molecule comprises the any of the means described above, and is capable of replication.

In one aspect, provided herein is a process for AAV mediated site-specific recombination, comprising: (a) a step for performing a function of obtaining a cell comprising a means for AAV mediated recombination, wherein the means optionally comprises a transgenic element; (b) a step for performing a function of growing the cell under conditions to allow site-specific recombination using at least one serine residue during catalysis. In one embodiment, the process includes obtaining a product, wherein, optionally the product is a therapeutic product.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 1 shows the alignment statistics and the sequence alignment of SPBetac2 integrase protein (SEQ ID NO:1, query) with a putative serine recombinase identified in the genome of *Bacillus safensis* strain CCMA-560 (SEQ ID NO:2, Sbjct), sequence ID: WP_029708089.1, with a length of 535 amino acids. The two proteins have 64% sequence identity at the protein level ranging from amino acids 1-529. This putative serine recombinase is named herein as SR21 (Serine Recombinase 21).

FIG. 2 shows the identification of a strain representing the pre-insertion locus: the alignment statistics and the sequence alignment of nucleotide 113 to 600 of a CCMA-560 DNA sequence (SEQ ID NO:58, query) with nucleotide 464352 to 464839 of whole genome shotgun sequence of *Bacillus safensis* strain Fairview contig56_1 (SEQ ID NO:59 Sbjct), Sequence ID: NZ_JFBY01000018.1, with a length of 568093 nucleotides.

DETAILED DESCRIPTION

Figure 3:
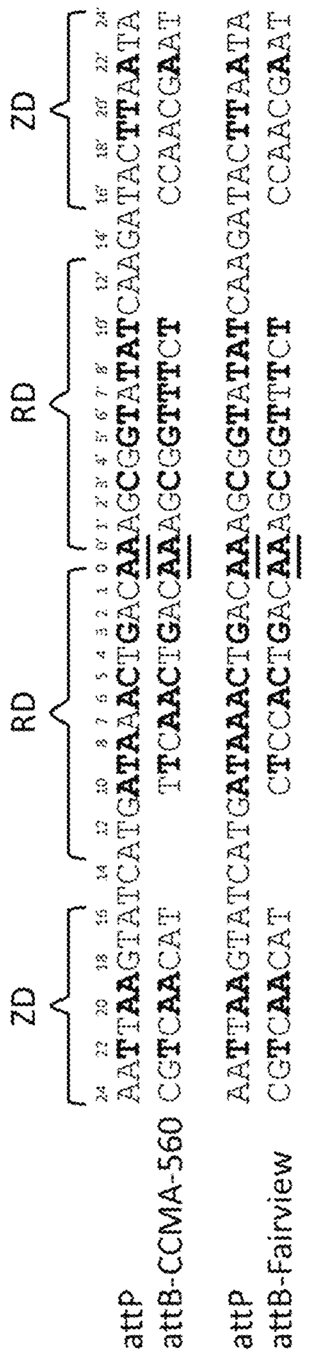
FIG. 3 shows SR21 recombinase attP and attB Sites. The attP and attB sites are composed of a dyad symmetry around a central dinucleotide recombination crossover site (underlined). Half sites are numbered. Spaces were introduced in attB sequences to show alignment of the sequence predicted to be bound by the zinc ribbon domain (ZD) and recombinase domain (RD) extrapolating from previous studies (Rutherford et al. (2013) Nucleic Acids Res. 41:8341-8356). Residues that are identical in three or four of the ZD or RD domains are in bold. The attP (SEQ ID NO:7) alignments to two alternate attB sequences (SEQ ID NO:8) and (SEQ ID NO:9) are shown.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the application can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Unless otherwise stated, any numerical value, such as a concentration or a concentration range described herein, are to be understood as being modified in all instances by the term "about." Thus, a numerical value typically includes 10% of the recited value. For example, a concentration of 1 mg/mL includes 0.9 mg/mL to 1.1 mg/mL. Likewise, a concentration range of 1 mg/mL to 10 mg/mL includes 0.9 mg/mL to 11 mg/mL. As used herein, the use of a numerical range expressly includes all possible subranges, all individual numerical values within that range, including integers within such ranges and fractions of the values unless the context clearly indicates otherwise.

The phrases "percent (%) sequence identity" or "% identity" or "% identical to" when used with reference to an amino acid sequence describe the number of matches ("hits") of identical amino acids of two or more aligned amino acid sequences as compared to the number of amino acid residues making up the overall length of the amino acid sequences. In other terms, using an alignment, for two or more sequences the percentage of amino acid residues that are the same (e.g. 90%, 91%, 92%, 93%, 94%, 95%, 97%, 98%, 99%, or 100% identity over the full-length of the amino acid sequences) may be determined, when the sequences are compared and aligned for maximum correspondence as measured using a sequence comparison algorithm as known in the art, or when manually aligned and visually inspected. The sequences which are compared to determine sequence identity may thus differ by substitution(s), addition(s) or deletion(s) of amino acids. Suitable programs for aligning protein sequences are known to the skilled person. The percentage sequence identity of protein sequences can, for example, be determined with programs such as CLUSTALW, Clustal Omega, FASTA or BLAST, e.g using the NCBI BLAST algorithm (Altschul S F, et al (1997), *Nucleic Acids Res.* 25:3389-3402).

As used herein, a "non-naturally occurring" nucleic acid or polypeptide, refers to a nucleic acid or polypeptide that does not occur in nature. A "non-naturally occurring" nucleic acid or polypeptide can be synthesized, treated, fabricated, and/or otherwise manipulated in a laboratory and/or manufacturing setting. In some cases, a non-naturally occurring nucleic acid or polypeptide can comprise a naturally-occurring nucleic acid or polypeptide that is treated, processed, or manipulated to exhibit properties that were not present in the naturally-occurring nucleic acid or polypeptide, prior to treatment. As used herein, a "non-naturally occurring" nucleic acid or polypeptide can be a nucleic acid or polypeptide isolated or separated from the natural source in which it was discovered, and it lacks covalent bonds to sequences with which it was associated in the natural source. A "non-naturally occurring" nucleic acid or polypeptide can be made recombinantly or via other methods, such as chemical synthesis.

As used herein, the term "hybrid" when used in reference to an AAV cap gene is intended to mean a cap gene that includes portions of one serotype capsid combined with portions of a different serotype capsid. The term also includes an AAV cap gene variant in which the naturally occurring AAV serotype sequence contains one or more non-naturally occurring mutations.

As used herein, the term "spacer sequence" is intended to mean a region of non-coding nucleotides that has no apparent function except to separation other genetic elements.

As used herein, the term "operably linked" refers to a linkage or a juxtaposition wherein the components so described are in a relationship permitting them to function in their intended manner. For example, a promoter is operably linked to a coding sequence if it affects the transcription of the coding sequence, or a signal sequence operably linked to an amino acid sequence of interest is capable of secret or translocate the amino acid sequence of interest over a membrane.

In an attempt to help the reader of the application, the description has been separated in various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples. For example, while embodiments of non-naturally occurring nucleic acids or recombinant vectors of the application (e.g., plasmid DNA or viral vectors) described herein may contain particular components, including, but not limited to, certain promoter sequences, enhancer or regulatory sequences, intron, coding sequence of AAV Rep and/or Cap, polyadenylation signal sequences, etc. arranged in a particular order, those having ordinary skill in the art will appreciate that the concepts disclosed herein may equally apply to other components arranged in other orders that can be used in nucleic acids or vectors of the application. The application contemplates use of any of the applicable components in any combination having any sequence that can be used in nucleic acids or vectors of the application, whether or not a particular combination is expressly described.

As used herein, a "vector" is a nucleic acid molecule used to carry genetic material into a cell, where it can be replicated and/or expressed. Any vector known to those skilled in the art in view of the present disclosure can be used. Examples of vectors include, but are not limited to, plasmids, viral vectors (bacteriophage, animal viruses, and plant viruses), cosmids, and artificial chromosomes (e.g., YACs). Preferably, a vector is a DNA plasmid. One of ordinary skill in the art can construct a vector of the application through standard recombinant techniques in view of the present disclosure.

A vector of the application can be an expression vector. As used herein, the term "expression vector" refers to any type of genetic construct comprising a nucleic acid coding for an RNA capable of being transcribed. Expression vectors include, but are not limited to, vectors for recombinant protein expression, such as a DNA plasmid or a viral vector, and vectors for delivery of nucleic acid into a subject for expression in a tissue of the subject, such as a DNA plasmid or a viral vector. It will be appreciated by those skilled in the art that the design of the expression vector can depend on such factors as the choice of the host cell to be transformed, the level of expression of protein desired, etc.

In some embodiments of the application, a vector is a non-viral vector. Examples of non-viral vectors include, but are not limited to, DNA plasmids, bacterial artificial chromosomes, yeast artificial chromosomes, bacteriophages, etc. Preferably, a non-viral vector is a DNA plasmid. A "DNA plasmid", which is used interchangeably with "DNA plasmid vector," "plasmid DNA" or "plasmid DNA vector," refers to a double-stranded and generally circular DNA sequence that is capable of autonomous replication in a suitable host cell. DNA plasmids used for expression of an encoded polynucleotide typically comprise an origin of replication, a multiple cloning site, and a selectable marker, which for example, can be an antibiotic resistance gene. Examples of DNA plasmids suitable that can be used include, but are not limited to, commercially available expression vectors for use in well-known expression systems (including both prokaryotic and eukaryotic systems), such as pSE420 (Invitrogen, San Diego, Calif.), which can be used for production and/or expression of protein in *Escherichia coli*; pYES2 (Invitrogen, Thermo Fisher Scientific), which can be used for production and/or expression in *Saccharomyces cerevisiae* strains of yeast; MAXBAC©complete baculovirus expression system (Thermo Fisher Scientific), which can be used for production and/or expression in insect cells; pcDNA™ or pcDNA3™ (Life Technologies, Thermo Fisher Scientific), which can be used for high level constitutive protein expression in mammalian cells; and pVAX or pVAX-1 (Life Technologies, Thermo Fisher Scientific), which can be used for high-level transient expression of a protein of interest in most mammalian cells. The backbone of any commercially available DNA plasmid can be modified to optimize protein expression in the host cell, such as to reverse the orientation of certain elements (e.g., origin of replication and/or antibiotic resistance cassette), replace a promoter endogenous to the plasmid (e.g., the promoter in the antibiotic resistance cassette), and/or replace the polynucleotide sequence encoding transcribed proteins (e.g., the coding sequence of the antibiotic resistance gene), by using routine techniques and readily available starting materials. (See, e.g., Sambrook et al., Molecular Cloning a Laboratory Manual, Second Ed. Cold Spring Harbor Press (1989)).

Preferably, a DNA plasmid is an expression vector suitable for protein expression in mammalian host cells. Expression vectors suitable for protein expression in mammalian host cells include, but are not limited to, pUC, pcDNA™, pcDNA3™, pVAX, pVAX-1, ADVAX, NTC8454, etc. For example, the vector can be based on pUC57, containing a pUC origin of replication and ampicillin resistance gene (SEQ ID NO:30). It can further comprise a mammalian puromycin resistance gene cassette constructed from the Herpes virus thymidine kinase gene promoter (SEQ ID NO:26), the puromycin N-acetyl transferase coding region (SEQ ID NO:27), and a polyadenylation signal from bovine growth hormone gene (SEQ ID NO:28). The vector can also comprise an Epstein Barr Virus (EBV) OriP replication origin fragment (SEQ ID NO:29), which represents a composite of the 'Dyad Symmetry' region and the 'Family of Repeats' region of EBV.

A vector of the application can also be a viral vector. In general, viral vectors are genetically engineered viruses carrying modified viral DNA or RNA that has been rendered non-infectious, but still contains viral promoters and transgenes, thus allowing for translation of the transgene through a viral promoter. Because viral vectors are frequently lacking infectious sequences, they require helper viruses or packaging lines for large-scale transfection. Examples of viral vectors that can be used include, but are not limited to, adenoviral vectors, adeno-associated virus vectors, pox virus vectors, enteric virus vectors, Venezuelan Equine Encephalitis virus vectors, Semliki Forest Virus vectors, Tobacco Mosaic Virus vectors, lentiviral vectors, etc. The vector can also be a non-viral vector.

Preferably, a viral vector is an adenovirus vector, e.g., a recombinant adenovirus vector. As used herein, the terms "recombinant adenovirus vector" and "recombinant adenoviral vector" and "recombinant adenoviral particles" are used interchangeably and refer to a genetically-engineered adenovirus that is designed to insert a polynucleotide of interest into a eukaryotic cell, such that the polynucleotide is subsequently expressed. Examples of adenoviruses that can be used as a viral vector of the invention include those having, or derived from, the serotypes Ad2, Ad5, Ad11, Ad2, Ad24, Ad26, Ad34, Ad35, Ad40, Ad48, Ad49, Ad50, Ad52 (e.g., RhAd52), and Pan9 (also known as AdC68); these vectors can be derived from, for example, human, chimpanzee (e.g., ChAd1, ChAd3, ChAd7, ChAd8, ChAd21, ChAd22, ChAd23, ChAd24, ChAd25, ChAd26, ChAd27.1, ChAd28.1, ChAd29, ChAd30, ChAd31.1, ChAd32, ChAd33, ChAd34, ChAd35.1, ChAd36, ChAd37.2, ChAd39, ChAd40.1, ChAd41.1, ChAd42.1, ChAd43, ChAd44, ChAd45, ChAd46, ChAd48, ChAd49, ChAd49, ChAd50, ChAd67, or SA7P), or rhesus adenoviruses (e.g., rhAd51, rhAd52, or rhAd53). A recombinant adenovirus vector can for instance be derived from a human adenovirus (HAdV, or AdHu), or a simian adenovirus such as chimpanzee or gorilla adenovirus (ChAd, AdCh, or SAdV) or rhesus adenovirus (rhAd).

Preferably, an adenovirus vector is a recombinant human adenovirus vector, for instance a recombinant human adenovirus serotype 5, or any one of recombinant human adenovirus serotype 26, 4, 35, 7, 48, etc. A recombinant viral vector useful for the application can be prepared using methods known in the art in view of the present disclosure. For example, in view of the degeneracy of the genetic code, several nucleic acid sequences can be designed that encode the same polypeptide. A polynucleotide encoding a protein of interest can optionally be codon-optimized to ensure proper expression in the host cell (e.g., bacterial or mammalian cells). Codon-optimization is a technology widely applied in the art, and methods for obtaining codon-optimized polynucleotides will be well known to those skilled in the art in view of the present disclosure.

A non-naturally occurring nucleic acid molecule or a vector can comprise one or more expression cassettes. An "expression cassette" is part of a nucleic acid molecule or vector that directs the cellular machinery to make RNA and protein. An expression cassette can comprise a promoter sequence, an open reading frame, a 3'-untranslated region (UTR) optionally comprising a polyadenylation signal. An open reading frame (ORF) is a reading frame that contains a coding sequence of a protein of interest (e.g., Rep, Cap, recombinase or a recombinant protein of interest) from a start codon to a stop codon. Regulatory elements of the expression cassette can be operably linked to a polynucleotide sequence encoding a protein of interest.

A non-naturally occurring nucleic acid molecule or a vector of the application can contain a variety of regulatory sequences. As used herein, the term "regulatory sequence" refers to any sequence that allows, contributes or modulates the functional regulation of the nucleic acid molecule, including replication, duplication, transcription, splicing, translation, stability and/or transport of the nucleic acid or one of its derivative (i.e. mRNA) into the host cell or organism. Regulatory elements include, but are not limited to, a promoter, an enhancer, a polyadenylation signal, translation stop codon, a ribosome binding element, a transcription terminator, selection markers, origin of replication, etc.

A non-naturally occurring nucleic acid molecule or a vector can comprise a promoter sequence, preferably within an expression cassette, to control expression of a protein of interest. The term "promoter" is used in its conventional sense and refers to a nucleotide sequence that initiates the transcription of an operably linked nucleotide sequence. A promoter is located on the same strand near the nucleotide sequence it transcribes. Promoters can be a constitutive, inducible, or repressible. Promoters can be naturally occurring or synthetic. A promoter can be derived from sources including viral, bacterial, fungal, plants, insects, and animals. A promoter can be a homologous promoter (i.e., derived from the same genetic source as the vector) or a heterologous promoter (i.e., derived from a different vector or genetic source). For example, if the vector to be employed is a DNA plasmid, the promoter can be endogenous to the plasmid (homologous) or derived from other sources (heterologous). Preferably, the promoter is located upstream of the polynucleotide encoding a protein of interest within an expression cassette.

Examples promoters that can be used include, but are not limited to, a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter (CMV-IE), Epstein Barr virus (EBV) promoter, or a Rous sarcoma virus (RSV) promoter. A promoter can also be a promoter from a human gene such as human actin, human myosin, human hemoglobin, human muscle creatine, or human metalothionein. A promoter can also be a tissue specific promoter, such as a muscle or skin specific promoter, natural or synthetic. Preferably, a promoter is a strong eukaryotic promoter, such as a cytomegalovirus (CMV) promoter (nt −672 to +15), EF1-alpha promoter, herpes virus thymidine kinase gene promoter (SEQ ID NO:26), etc.

A non-naturally occurring nucleic acid molecule or a vector can comprise additional polynucleotide sequences that stabilize the expressed transcript, enhance nuclear export of the RNA transcript, and/or improve transcriptional-translational coupling. Examples of such sequences include polyadenylation signals and enhancer sequences. A polyadenylation signal is typically located downstream of the coding sequence for a protein of interest (e.g., Rep, Cap, recombinase) within an expression cassette of the vector. Enhancer sequences are regulatory DNA sequences that, when bound by transcription factors, enhance the transcription of an associated gene. An enhancer sequence is preferably downstream of a promoter sequence and can be downstream or upstream of a coding sequence within an expression cassette of the vector.

Any polyadenylation signal known to those skilled in the art in view of the present disclosure can be used. For example, the polyadenylation signal can be a SV40 polyadenylation signal (e.g., SEQ ID NO:60), AAV2 polyadenylation signal (bp 4411-4466, NC_001401.2), a polyadenylation signal from the Herpes Simplex Virus Thymidine Kinase Gene (SEQ ID NO:23), LTR polyadenylation signal, bovine growth hormone (bGH) polyadenylation signal, human growth hormone (hGH) polyadenylation signal, or human β-globin polyadenylation signal. Preferably, a polyadenylation signal is a bovine growth hormone (bGH) polyadenylation signal (SEQ ID NO:28), the polyadenylation signal of AAV2 having nucleotide numbers 4411 to 4466 of the nucleotide sequence of GenBank accession number NC_001401.2, or a SV40 polyadenylation signal (SEQ ID NO:60).

Any enhancer sequence known to those skilled in the art in view of the present disclosure can be used. For example, an enhancer sequence can be human actin, human myosin, human hemoglobin, human muscle creatine, or a viral enhancer, such as one from CMV, HA, RSV, or EBV. Examples of particular enhancers include, but are not limited to, Woodchuck HBV Post-transcriptional regulatory element (WPRE), intron/exon sequence derived from human apolipoprotein A1 precursor (ApoAI), untranslated R-U5 domain of the human T-cell leukemia virus type 1 (HTLV-1) long terminal repeat (LTR), a splicing enhancer, a synthetic rabbit β-globin intron, or any combination thereof.

Preferably, an enhancer sequence comprises a P5 promoter of an AAV. The P5 promoter is part of a cis-acting Rep-dependent element (CARE) inside the coding sequence of the rep gene. CARE was shown to augment the replication and encapsidation when present in cis. CARE is also important for amplification of chromosomally integrated rep genes (if AAV ITRs are not present) as in some AAV producer cell lines. While not wishing to be bound by theories, it is believed that a P5 promoter placed downstream of a cap coding sequence potentially act as an enhancer to increase Cap expression, thus AAV yields, and that it also provides enhancer activity for amplifying genes integrated into a chromosome.

A non-naturally occurring nucleic acid molecule or a vector, such as a DNA plasmid, can also include a bacterial origin of replication and an antibiotic resistance expression cassette for selection and maintenance of the plasmid in bacterial cells, e.g., *E. coli*. An origin of replication (ORI) is a sequence at which replication is initiated, enabling a plasmid to reproduce and survive within cells. Examples of ORIs suitable for use in the application include, but are not limited to ColE1, pMB1, pUC, pSC101, R6K, and 15A, preferably pUC.

Vectors for selection and maintenance in bacterial cells typically include a promoter sequence operably linked to an antibiotic resistance gene. Preferably, the promoter sequence operably linked to an antibiotic resistance gene differs from the promoter sequence operably linked to a polynucleotide sequence encoding a protein of interest. The antibiotic resistance gene can be codon optimized, and the sequence composition of the antibiotic resistance gene is normally adjusted to bacterial, e.g., *E. coli*, codon usage. Any antibiotic resistance gene known to those skilled in the art in view of the present disclosure can be used, including, but not limited to, kanamycin resistance gene ($Kan^r$), ampicillin resistance gene ($Amp^r$), and tetracycline resistance gene ($Tet^r$), as well as genes conferring resistance to chloramphenicol, bleomycin, spectinomycin, carbenicillin, etc.

Vectors for selection and maintenance in mammalian cells typically include a promoter sequence operably linked to a gene encoding a protein that confers a selectable marker. Preferably, the gene further comprises a polyadenylation signal. For example, a mammalian puromycin resistance gene cassette can comprise a herpes virus thymidine kinase gene promoter (SEQ ID NO:26), a puromycin N-acetyl transferase coding region (SEQ ID NO:27), and a polyadenylation signal from bovine growth hormone gene (SEQ ID NO:28).

Manufacturing of recombinant AAV in human cells requires expression of AAV replication (rep) and capsid (cap) genes, adenovirus genes and an AAV-packagable transgene consisting of an expression cassette flanked by AAV inverted terminal repeats (ITRs). All three components can be delivered to cells on separate plasmids for AAV production, but existing transfection methods are difficult to scale to large-scale cultures. Incorporating some of these elements into the host cell line could make AAV production more efficient, however, some of the AAV and adenovirus genes are cytostatic or cytotoxic, limiting this approach.

The present application describes non-naturally occurring nucleic acid molecules, vectors, cells and methods to reversibly-inactivate the AAV rep gene such that AAV rep gene, AAV cap gene and a packagable transgene can be maintained and/or integrated into suitable host cells and expanded. Infection of these cells by a recombinant adenovirus expressing a recombinase reactivates the rep genes and induces AAV replication and packaging. Different from the approach described by Xiao and coworkers (Qiao et al. (2002) J. Virol. 76: 13015-13027; Yuan et al. (2011) Hum. Gene Ther. 22:613-624), which uses Cre, a tyrosine recombinase that recognizes two identical loxP sites and catalyzes both joining and excision reactions, the present invention uses Serine Recombinase 21 (SR21), a serine recombinase newly characterized by the inventors of this application. Unlike Cre, SR21 recognizes the attP and attB sites, which have different sequences. After the joining reaction catalyzed by SR21, the attP and attB sites are recombined and destroyed so that no additional recombination is possible. Thus, a method of the application can be more efficient than that catalyzed by Cre. Certain embodiments of the application include additional features, such as different stop cassette inserted in different artificial introns, enhancers, insulators, etc., which make further improvements to the approaches in the prior art. The reversible inactivation/reactivation system of the application allows the AAV rep gene to be tightly controlled during packaging cell growth to thus avoid the cytostatic/cytotoxic effect of the Rep proteins to the host cell. It also provides strong induction of the AAV rep gene and high yields of AAV vectors during production of the vectors.

Serine Recombinase

Site specific recombination catalyzed by members of the large serine recombinase family (such as SR21) does not require cellular machinery for homologous recombination. Typically, it requires a specialized recombinase that recognizes the sites, breaks and joins the DNA. Based on amino acid sequence homology and mechanistic relatedness, most site-specific recombinases are grouped into one of two families: the tyrosine recombinase family or the serine recombinase family. The names stem from the conserved nucleophilic amino acid residue that they use to attack the DNA and which becomes covalently linked to it during strand exchange.

Serine recombinases bind and recombine separate recombination recognition sites known as "attachment sites": attP, "attachment phage" and attB, "attachment bacterial" chromosome. The attP and attB sites are composed of a dyad symmetry around a central dinucleotide recombination crossover site. The left and right halves of attP and attB sites are bound by recombinase monomers by the zinc ribbon (ZD) and recombinase (RD) domains (Rutherford et al. (2013) Nucleic Acids Res. 41:8341-8356).

As described in more detail below in the Example, a serine recombinase, herein referred to as "Serine Recombinase 21" or "SR21" was newly identified in the present invention in the genome of *Bacillus safensis* strain CCMA-560. The attP and attB sites recognized by SR21 were also characterized in the present invention.

In one general aspect, the application relates to a non-naturally occurring nucleic acid molecule comprising a nucleotide sequence encoding a serine recombinase having an amino acid sequence having at least 85%, such as at least 85%, 86%, 87%, 88%, 89%, 90%, 91%, 92%, 93%, 94%, 95%, 96%, 97%, 98%, 99% or 100%, identity to the amino acid sequence of SEQ ID NO:2. Preferably, the non-naturally occurring nucleic acid molecule comprises a nucleotide sequence encoding a serine recombinase having the amino acid sequence of SEQ ID NO:2. In one embodiment, the non-naturally occurring nucleic acid molecule comprises a nucleotide sequence having at least 85%, such as at least 85%, 86%, 87%, 88%, 89%, 90%, 91%, 92%, 93%, 94%, 95%, 96%, 97%, 98%, 99% or 100%, identity to the nucleotide sequence of SEQ ID NO:3.

In certain embodiments, the application relates to a vector comprising the non-naturally occurring nucleic acid. The vector can be an expression vector that expresses the serine recombinase in a cell of interest, e.g., a bacterial cell or a mammalian cell. In one embodiment, the vector expresses the serine recombinase in a mammalian cell under control of a cytomegalovirus (CMV) promoter or any other suitable promoter described herein or known in the art. In certain embodiments, the vector can further include a polyadenylation signal, such as a simian virus 40 (SV40) polyadenylation signal or any other suitable polyadenylation signal described herein or known in the art.

In one embodiment, the vector is a DNA plasmid, such as plasmid P175 having the nucleotide sequence of SEQ ID NO:10.

In another embodiment, the vector is a viral vector, such as a recombinant adenoviral vector.

In one embodiment, the vector is a recombinant ΔE1/ΔE3 adenovirus serotype 5 (Ad5) virus comprising a nucleotide sequence encoding a serine recombinase having at least 85% identity, such as at least 85%, 86%, 87%, 88%, 89%, 90%, 91%, 92%, 93%, 94%, 95%, 96%, 97%, 98%, 99% or 100% identity, to the amino acid sequence of SEQ ID NO:2, and the coding sequence is under the control of a promoter functional in a mammalian cell. Preferably, the promoter is a CMV promoter. More preferably, the recombinant Ad5 vector comprises, in 5' to 3' order, a CMV promoter operably linked to a nucleotide sequence encoding the amino acid sequence of SEQ ID NO:2, which is operably linked to a SV40 polyadenylation signal (NC_001669.1, nt 2550 to 2774). In one embodiment, the nucleotide sequence encoding the amino acid sequence of SEQ ID NO:2 is the same as SEQ ID NO:3 except that the bacterial translation initiation codon "TTG" is replaced by an "ATG", and three point-mutations were introduced to destroy restriction endonuclease recognition sites within SEQ ID NO:3. These restriction endonuclease recognition sites are Xba I site (TCTAGA); Sac I site (GAGCTC); EcoRI site (GAATTC).

A vector encoding a serine recombinase of the application can be made using any methods known in the art in view of the present disclosure.

As described in more detail in the Example below, attP and attB sites for a serine recombinase of the application are identified in the present invention. In certain embodiments, a serine recombinase of the application recognizes an attP site comprising the nucleotide sequence of SEQ ID NO:7 or a variant thereof. In certain embodiments, a serine recombinase of the application recognizes an attP site comprising a nucleotide sequence at least 90%, such as at least 91%, 92%, 93%, 94%, 95%, 96%, 97%, 98%, 99% or 100%, identical to SEQ ID NO:7.

In certain embodiments, a serine recombinase of the application recognizes an attB site comprising the nucleotide sequence of SEQ ID NO:8 or SEQ ID NO:9, or a variant thereof. In certain embodiments, a serine recombinase of the application recognizes an attB site comprising a nucleotide sequence at least 90%, such as at least 91%, 92%, 93%, 94%, 95%, 96%, 97%, 98%, 99% or 100%, identical to SEQ ID NO:8 or SEQ ID NO:9.

In one embodiment, the application relates to a method of conducting a site-specific recombination in a cell. The method comprises:

1) obtaining a cell comprising a nucleic acid molecule having an attP site having a nucleotide sequence at least 90% identical to SEQ ID NO:7, and an attB site having a nucleotide sequence at least 90% identical to SEQ ID NO:8 or SEQ ID NO:9;
2) introducing to the cell a non-naturally occurring nucleic acid molecule encoding a serine recombinase having at least 85% identity, such as at least 85%, 86%, 87%, 88%, 89%, 90%, 91%, 92%, 93%, 94%, 95%, 96%, 97%, 98%, 99% or 100% identity, to SEQ ID NO:2; and
3) growing the cell under conditions to allow the serine recombinase to catalyze the site-specific recombination between the attP and attB sites.

In a preferred embodiment, the application relates to a method of conducting a site-specific recombination in a cell. The method comprises:

1) obtaining a cell comprising a nucleic acid molecule having an attP site having the nucleotide sequence of SEQ ID NO:7, and an attB site having the nucleotide sequence of SEQ ID NO:8 or SEQ ID NO:9;
2) introducing to the cell a non-naturally occurring nucleic acid molecule encoding a serine recombinase having the amino acid sequence of SEQ ID NO:2; and
3) growing the cell under conditions to allow the serine recombinase to catalyze the site-specific recombination between the attP and attB sites.

Constructs, Cells and Methods for Production of Recombinant AAV

As illustrated in the Example below, the newly identified serine recombinase of the application can be used to improve production of recombinant AAVs.

Modified AAV Rep Gene Construct

In one general aspect, the application is related to a non-naturally occurring nucleic acid molecule comprising a modified adeno-associated virus (AAV) rep gene, which has an AAV rep gene encoding four Rep proteins Rep78, Rep68, Rep52 and Rep40 and an artificial intron inserted into a coding sequence of the rep gene shared by the four Rep proteins. The artificial intron comprises a stop cassette inserted downstream of the 5' splice site and upstream of the branch site of the artificial intron, and the stop cassette comprises, in 5' to 3' order: (i) an attP site having a nucleotide sequence at least 90%, such as at least 91%, 92%, 93%, 94%, 95%, 96%, 97%, 98%, 99% or 100%, identical to SEQ ID NO:7, (ii) a splice acceptor; (iii) a terminator; and (iv) an attB site having the nucleotide sequence at least 90%, such as at least 91%, 92%, 93%, 94%, 95%, 96%, 97%, 98%, 99% or 100%, identical to SEQ ID NO:8 or SEQ ID NO:9. Preferably, the attP site has the nucleotide sequence of SEQ ID NO:7 and the attB site has the nucleotide sequence of SEQ ID NO:8 or SEQ ID NO:9.

As used herein, an "intron" is broadly defined as a sequence of nucleotides that is removable by RNA splicing. "RNA splicing" means the excision of introns from a pre-mRNA to form a mature mRNA. An "artificial intron" as used herein refers to a sequence of nucleotides that is not a naturally occurring intron for a gene but is nonetheless removable by RNA splicing. For example, an "artificial intron" can be a naturally occurring intron with an inserted stop cassette.

An intron, including an artificial intron, contains a 5' splice site or junction, a splice acceptor or branch point, and a 3' splice site or splice junction. The term "5' splice site" or "5' splice junction" means the location of the exon-intron junction wherein the junction is between the 3' end of the 5' fragment of a gene or nucleic acid fragment and the 5' end of the intron, and includes the consensus sequence at the 5' end of the intron that is required for RNA splicing. The term "splice acceptor" or "branch point" refers to the nucleotide, usually adenosine, located approximately 20-50 bp from the 3' splice site that helps form the lariat structure during the first trans-esterification reaction during RNA splicing. The term "3' splice site" or "3' splice junction" means the location of the exon-intron junction wherein the junction is between the 5' end of the 3' fragment of a gene or nucleic acid fragment and the 3' end of the intron, and also includes the consensus sequence at the 3' end of the intron that is required for RNA splicing. The term "consensus sequence" means the nucleotides in/or adjacent to either the 5' or 3' splice junction that are required for RNA splicing; these sequences are usually either invariant or highly conserved.

Analysis of a large number of mRNAs has revealed that certain nucleotides are conserved in typical introns and splice junctions. For example, nearly invariant bases of an intron are the 5'-GU and the 3'-AG. Certain bases that flank these 5' and 3' conserved regions often are found in abnormal (non-random) frequencies. Also conserved is the branch-point adenosine, usually 20-50 bases from the 3' splice site. See, e.g., FIG. 4 of Gao et al (2008) Nucleic Acids Research 36: 2257-2267, that shows the general consensus for introns in the context of an exon, the entire content of Gao et al (2008) is incorporated herein by reference. However, the central region of the intron, which may range from 40 to 50,000 bases in length, is generally unnecessary for splicing to occur. Introns are removed from RNA or pre-mRNA as a lariat structure by spliceosomes. The splicing together of exons proceeds via two sequential transesterification reactions.

Insertion of an intron into an expressed sequence can be accomplished by any method known in the art. The flanking exonic context as well the actual intronic sequence to be used play a role in whether the new "intron" will be effectively spliced out. Introns suitable for the invention can be tested by making composite sequences in silico and using online splice prediction programs to find combinations of the rep gene sequence and intron sequences that give high enough scores for efficient RNA splicing. Any of the introns in the genome or synthetic sequences can be tested and optimized for use in constructs of the invention in view of the present disclosure.

To disrupt expression of all four rep open reading frames for Rep78, Rep68, Rep52 and Rep40, an artificial intron is preferably inserted into a coding sequence of the rep gene shared by the four Rep proteins. Accordingly, in certain embodiments, to disrupt all four ORFs, an artificial intron is inserted after nucleotides 996 and up to 1905 of AAV2 (NC_001401.2) or corresponding positions in another AAV rep gene. But for the stop cassette to work when inserted in the artificial intron, it is preferred to have the intron inserted in the rep gene as far upstream as possible.

Additionally, the exonic context just upstream and downstream of the intron insertion site is important to defining what will work as a possible insertion site, e.g., the general consensus for introns in the context of an exon discussed above. In one embodiment, the consensus sequence CAG^G (where ^ marks where the insertion would go) occurs in the relevant region of rep gene in AAV2 as follows where the number indicates the last nucleotide of AAV before the insertion: 1052, 1061, 1712, and 1906. In another embodiment, the consensus sequence AAG^G occurs in locations 1022 (as used by Qiao), 1112, 1475, 1514, 1700, 1742, and 1784 of AAV2. Other consensus sites, such as AAG^A, occur at, e.g., nucleotide 1340 of AAV2. The preferred insertion site can also be identified in rep genes of other AAVs in view of the present disclosure.

The artificial intron useful for the invention can be derived from any source, such as from a genomic library. An intron can be obtained by polymerase chain reaction (PCR) from human DNA using primers, as described below. Any intron capable of RNA splicing in cells can be used in the method of the present invention. In the Example below, the intron is an intron of human R-Actin gene.

According to embodiments of the application, in addition to RNA splicing via an artificial intron, the expression of Rep proteins is also regulated by DNA splicing via a stop cassette inserted into the artificial intron. The stop cassette comprises a transcription terminator flanked by the attP and attB sites specifically recognized by a serine recombinase, such as that characterized in the invention. In one embodiment, the terminator comprises one or more polyadenylation signals. In another embodiment, the terminator comprises another sequence for efficient transcription termination, such as a sequence from the human β-globin gene downstream of the polyadenylation signal that encodes a self-cleaving RNA motif, preferably having the nucleotide sequence of SEQ ID NO:19. Other terminators can also be used in the invention, such as a hammerhead ribozyme that cleave its own RNA. See West (2008) Molecular Cell 29:600-610 for use of other ribozyme replacing the beta globin element, and Kharma (2016) Nucleic Acids Res. 44:e39 for description of designing ribozymes, the contents of both are incorporated herein by reference in their entireties.

In one embodiment, the stop cassette further comprises a gene encoding a selectable marker. In one embodiment, the selectable marker gene comprises a neomycin phosphotransferase expression cassette (neo) (SEQ ID NO:18), which is driven by a mammalian promoter (e.g., mouse phosphoglycerate kinase 1) and a bacterial (e.g., Lac zya) promoter and followed by a polyadenylation signal, such as that from SV40. This gene confers resistance to neomycin and kanamycin in mammalian and bacterial cells, respectively. While not wishing to be bound by theories, it is believed that, in addition to serving a selectable marker for cell line development, a selectable marker gene can further block the transcription of the rep gene to thereby increase the stability of a host cell containing the modified rep gene. Other selectable marker genes that can be used in the invention include, but are not limited to, antibiotic selection genes (puromycin, hygromycin, bleomycin), a metabolic gene (e.g. glutamine synthase or hypoxanthine-guanine phosphoribosyltransferase (HPRT)), a visual marker such as mCherry, an enzyme such as beta-glactosidase, secreted alkaline phosphatase, or any other suitable marker genes.

In another embodiment, the stop cassette comprises a splice acceptor to prevent the stop cassette from being splice out of primary mRNA transcripts. Any naturally occurring splice acceptor site or synthetic sequence can be used, provided that the splice acceptor is not skipped. According to embodiments of the application, the splice acceptor contains a branch point sequence conforming to the consensus (yTnAynn), wherein y is a C or T and n is any nucleotide, a polypyrimidine tract (4-24 nt), an "AG" dinucleotide and a eukaryotic gene exon sequence (or synthetic sequence that acts like an exon when placed next to the intron sequence) of 20-80 bp. The sequence should be recognized as a splice acceptor site by NetGene2 Splice prediction software (cbs.dtu.dk/services/NetGene2/; Brunak, S., Engelbrecht, J., and Knudsen, S.: Prediction of Human mRNA Donor and Acceptor Sites from the DNA Sequence, Journal of Molecular Biology, 1991, 220, 49-65) with a confidence score of 0.4 or better (or with similar splice prediction software); scores closer to 1.0 are better. In one embodiment, the splice acceptor comprises the nucleotide sequence of SEQ ID NO:17 (NC_000086.7, nucleotides 53001998 to 53002138 from the mouse HPRT gene, plus a 29 nt region from the human agouti signaling protein (NC_000020.11, nucleotides 34262765 to 34262793).

According to embodiments of the application, the stop cassette is inserted downstream of the 5' splice donor site and upstream of the splice acceptor "branch point" of the artificial intron. The stop cassette can be inserted at any position between the two sites, provided that the insertion does not damage the functions of the sites. In one embodiment, the stop cassette is inserted in the middle of the two sites. In one exemplary embodiment described in the Example below, the stop cassette is inserted into the intron of human β-Actin gene such that the 5' intron fragment has the nucleotide sequence of SEQ ID NO:14 and the 3' intron fragment has the nucleotide sequence of SEQ ID NO:15.

As provided herein, in some embodiments the 3' intron fragment can include a spacer sequence that makes the REP/CAP gene too large to package in AAV. For example, the AAV packaging limit is approximately 5.0 kb. Thus, a spacer sequence that makes the REP/CAP gene greater than approximately 5.0 kb can be generated according to the disclosure provided herein. In some embodiments, the spacer sequence is a 2 kb random spacer inserted in the 3' intron fragment. Accordingly, in an exemplary embodiment described in the Example below, the stop cassette is inserted into the intron of human β-Actin gene such that the 5' intron fragment has the nucleotide sequence of SEQ ID NO:14 and the 3' intron fragment has the nucleotide sequence of SEQ ID NO:66. However, it is understood that the spacer sequence need not be 2 kb, and can be any length that results in the REP/CAP gene being larger than approximately 5.0 kb.

Any AAV rep gene can be included in the modified rep gene of the invention. For example, the AAV rep gene can comprise a rep gene of one of AAV1 to AAV8, or a hybrid thereof. The sequences of the AAV rep gene are available from, e.g., GenBank, with the following GenBank accession numbers for the various AAV genomes: AAV1, GenBank accession No. NC_002077.1; AAV2, GenBank accession No. NC_001401.2; AAV3, GenBank accession No. NC_001729.1; AAV4, GenBank accession No. NC_001829.1; AAV5, GenBank accession No. NC_006152.1; AAV6, GenBank accession No. AF028704.1; AAV7, GenBank accession No. NC_006260.1; and AAV8, GenBank accession No. NC_006261.1.

In the Example below, a rep gene of human AAV2 having nucleotide numbers 190 to 2202 of the nucleotide sequence of GenBank accession number NC_001401.2 is used.

In some embodiments, modifications to a cryptic splice site in the rep gene can be made to eliminate splicing at this site. For example, a synonymous mutation to the DNA sequence can be made in which the DNA sequence is mutated, but the mutation does not change the encoded amino acid.

Constructs with a Modified AAV Rep Gene and an AAV Cap Gene

In another general aspect, the application relates to a non-naturally occurring nucleic acid molecule comprising a modified AAV rep gene of the application and an AAV cap gene, or hybrid thereof. Preferably, the AAV cap gene is downstream of the modified AAV rep gene.

In one embodiment, the AAV cap gene further comprises a polyadenylation signal operably linked to a coding sequence of the gene. In an exemplary embodiment described in the example below, an AAV2 polyadenylation signal (bp 4411-4466, NC_001401.2) is included downstream of the AAV9 cap coding sequence.

In another embodiment, the AAV cap gene further comprises an enhancer. In the example below, an AAV2 rep P5 promoter (bp 190-313, NC_001401.2) is included downstream of the AAV2 polyadenylation signal.

In certain embodiment, the AAV cap gene encodes all three of the capsid proteins VP1, VP2 and VP3.

In other embodiments, the AAV cap gene encodes less than three of the capsid proteins. For example, it was reported that AAV serotypes 1 through 5 could successfully package, replicate in, and transduce cells without VP2 (Grieger et al., J Virol. 2005 August; 79(15): 9933-9944). According, in one embodiment, the AAV cap gene encodes VP1 and VP3, but not VP2, of any of AAV 1 to AAV5, or a hybrid thereof.

Any AAV cap gene can be used in the invention. For example, the AAV cap gene can be a cap gene of one of AAV1 to AAV8, AAV9, AAVDJ, or a hybrid thereof. In one embodiment, the cap gene is an AAV9 variant. The sequences of the AAV cap gene are available from, e.g., GenBank. See the above described GenBank accession numbers for the AAV1 to AAV8 genomes. The AAV9 genome has the GenBank accession No. AY530579.1, and the AAVDJ has the GenBank protein accession No, 3J1Q_A.

In one embodiment, described in the Example below, a cap open reading frame of human AAV9 having the nucleotide sequence of GenBank accession number AY530579.1 is used.

Constructs with a Modified AAV Rep Gene, an AAV Cap Gene and a Transgene

In another general aspect, the application relates to a non-naturally occurring nucleic acid molecule comprising a modified AAV rep gene of the application, an AAV cap gene and a transgene flanked by AAV Inverted Terminal Repeats (ITRs).

The ITRs are important cis-active sequences in the biology of AAV. A key role of the ITRs is in AAV DNA replication. In addition to its role in AAV replication, the ITR is also essential for AAV genome packaging, transcription, negative regulation under nonpermissive conditions, and site-specific integration.

In one embodiment, a 130 bp ITR comprises the nucleotide sequence of SEQ ID NO:20 derived from the 3' AAV2 ITR (Nucleotides 4535-4664, NC_001401.2) is used to flank the transgene. In another embodiment, a shorter mutated ITR is used. For example, for shorter genes, an ITR is mutated to be shorter and the gene can fold into a double-stranded form to increase expression and speed up expression after infection. See McCarty 2008 Mol Ther. 2008; 16(10):1648-56.

In another embodiment, the transgene comprises a promoter, preferably a promoter functional in a mammalian cell. In the Example described below, a human EF1-alpha promoter (including exon 1, intron 1, and part of exon 2) (SEQ ID NO:21) is included in the transgene.

In another embodiment, the transgene comprises a polyadenylation signal. In the Example described below, a polyadenylation signal from the Herpes Simplex Virus Thymidine Kinase Gene (SEQ ID NO:23) is included in the transgene.

In yet another embodiment, a non-naturally occurring nucleic acid molecule comprises a pair of insulators flanking a modified AAV rep gene, an AAV cap gene and an ITR flanked transgene. In another embodiment, a non-naturally occurring nucleic acid molecule comprises a single insulator upstream of a modified AAV rep gene, an AAV cap gene and an ITR flanked transgene. In one embodiment, the insulator comprises genomic elements that block chromatin-associated repression of gene expression (Kwaks et al. (2003) Nature Biotechnology 21: 554-558; Kwaks et al. (2003) Nature Biotechnology 21: 822).

Any suitable insulator, such as those described herein, can be used in the invention. In one embodiment the insulator is a human anti-repressor element 40 having the nucleotide sequence of SEQ ID NO:24. In another embodiment, the insulator is a mouse anti-repressor element 40 having the nucleotide sequence of SEQ ID NO:25. In another embodiment, In another embodiment, the insulator is an anti-repressor element 04 having the nucleotide sequence of GenBank accession number AY190749.1. In another embodiment, the insulator is an anti-repressor element 06 having the nucleotide sequence of GenBank accession number AY190750.1. In another embodiment, the insulator is an anti-repressor element 07 having the nucleotide sequence of GenBank accession number AY190751.1. In another embodiment, the insulator is an anti-repressor element 12 having the nucleotide sequence of GenBank accession number AY190752.1. In another embodiment, the insulator is an anti-repressor element 13 having the nucleotide sequence of GenBank accession number AY190753.1. In another embodiment, the insulator is an anti-repressor element 35 having the nucleotide sequence of GenBank accession number AY190754.1. In another embodiment, the insulator is an anti-repressor element 36 having the nucleotide sequence of GenBank accession number AY190755.1. In another embodiment, the insulator is an anti-repressor element 52 having the nucleotide sequence of GenBank accession number AY190757.1. In another embodiment, the insulator is an anti-repressor element 53 having the nucleotide sequence of GenBank accession number AY190758.1. In another embodiment, the insulator is a Chicken HS4 insulator from the globin locus having the nucleotide sequence of AY040835.1 in two or more copies.

The non-naturally occurring nucleic acid molecule that comprises a pair of insulators can have the same or different insulators as a pair to flank the gene segment of interest. Preferably, different insulators are used as a pair to flank the gene segment of interest. In one exemplary embodiment described the Example below, human anti-repressor element 40 (AY190756.1, SEQ ID NO:24) and mouse anti-repressor element 40 (SEQ ID NO:25) are used as the insulators. In another exemplary embodiment described the Example below, human anti-repressor element 40 (AY190756.1, SEQ ID NO:24) is used as the insulator.

As provided herein, the constructs on the present disclosure can also include spacer sequences on both sides of the AAV transgene to decrease the risk of mispackaging other vector components. In one embodiment, the non-naturally occurring nucleic acid molecule comprises a first and a second spacer sequence upstream and downstream of the transgene, respectively. In certain embodiments, the spacer sequences are 2 kb spacer sequences. In a specific embodiment, the non-naturally occurring nucleic acid molecule comprises the first insulator upstream of the modified AAV rep gene, and further comprises a first and a second spacer sequence upstream and downstream of the transgene, respectively, wherein the first insulator and the second spacer sequence are independently selected from the group consisting of: (a) a nucleotide sequence of SEQ ID NO:67; and (b) a nucleotide sequence of SEQ ID NO:68.

Cells and Methods for Production of Recombinant AAV

Expression of the Rep proteins from a modified AAV rep gene of the application is under tight control by both DNA splicing and RNA splicing mechanisms, thus allowing stable host cells containing the modified rep gene to be generated and grown to high numbers in a bioreactor. For AAV production, a stable host cells containing a modified AAV rep gene, an AAV cap gene and a transgene flanked by ITRs are first grown to high numbers, then infected with a replication deficient adenovirus expressing a serine recombinase that recognizes the attP and attB sites in the modified AAV rep gene. A site-specific recombination between the attP and attB sites catalyzed by the serine recombinase splices out the stop cassette, resulting in the production of a pre-mRNA comprising both the 5' and 3' rep coding sequences separated by a functional intron. The intron is then excised by ubiquitous cellular machinery (spliceosomes), resulting in an mRNA encoding the four Rep proteins, allowing production of AVVs at high titer.

Stable host cells containing a modified AAV rep gene, an AAV cap gene and a transgene flanked by ITRs can be obtained by transducing a cell with one or more nucleic acid molecules encoding the genes. In one embodiment, a stable host cell is obtained by transducing a cell with a first nucleic acid molecule encoding a modified AAV rep gene and an AAV cap gene to obtain a first host cell comprising the modified AAV rep gene and AAV cap gene, and further transducing the first host cell with a second nucleic acid molecule encoding a transgene flanked by ITRs. In one embodiment, the modified AAV rep gene and the AAV cap gene are stably integrated into the chromosome of the first host cell. In another embodiment, the modified AAV rep gene and the AAV cap gene remain episomal in the first host cell. The transgene flanked by ITRs can also be stably integrated into the host cell or remain episomal.

In another embodiment, a stable host cell is obtained by transducing a cell with a nucleic acid molecule encoding a modified AAV rep gene, an AAV cap gene and a transgene flanked by ITRs. The modified AAV rep gene, the AAV cap gene and the transgene flanked by ITRs can be stably integrated into the host cell or remain episomal.

The stable host cells can be grown to high cell density before being infected with an adenovirus expressing a serine recombinase.

A replication deficient adenovirus expressing a serine recombinase of the application is introduced to the stable host cells using any methods known in the art in view of the present disclosure. In one embodiment, the replication deficient adenovirus is a recombinant ΔE1/ΔE3 adenovirus serotype 5 (Ad5) virus comprising a nucleotide sequence encoding an amino acid sequence at least 85% identical to the amino acid sequence of SEQ ID NO:2, preferably 100% identical to SEQ ID NO:2. For example, the adenovirus can comprise a nucleotide sequence that is at least 85% identical to SEQ ID NO:3, preferably at least 95% identical to SEQ ID NO:3.

As disclosed herein, the present disclosure also includes methods and compositions for increasing AAV production by contacting the cells described herein with 2 aminopurine (2-AP). At late stages of the adenovirus life cycle, the virus inhibits host protein synthesis. This results in part from the actions of the late adenovirus 100-kilodalton (kDa) protein, which displaces Mnkl kinase from the cap-initiation complex eIF4F, leading to dephosphorylation of eIF4E and the inhibition of cap-dependent mRNA translation (see, e.g., Cuesta (2004), J. Virology 78: 7707-7716). Adenoviral late gene transcripts include a tripartite leader sequence at their 5' end that promotes translation by a mechanism called ribosome shunting (see, e.g., Yueh (2000) Genes Dev 14: 414-421). In the context of an AAV producer cell line, inhibition of cap-dependent translation is predicted to block expression of AAV REP and CAP genes as well as early adenoviral proteins needed for AAV replication and packaging. Thus, in some embodiments, the cells are cultured with chemicals that block host protein translation shutdown to increase the efficiency of AAV producer cell lines using an adenoviral inducer.

In certain embodiments, the chemical that blocks host protein translation shutdown is 2-aminopurine (2-AP). 2-AP has been shown to block the shutdown of host protein synthesis induced by adenovirus (see, e.g., Zhang and Schneider (1994) J. Virology 68: 2544-2555; Huang and Schneider (1990) PNAS 87: 7115-7119). Treatment of AAV producing cells with 2-AP was able to reduce the cytopathic effects of infection including restoration of the cytokeratin network normally degraded by late infection (Zhang and Schneider (1994) J. Virology 68: 2544-2555). 2-AP inhibits a number of kinases in vitro including the RNA-dependent protein kinase PKR (also known as eukaryotic translation initiation factor 2 alpha kinase 2, EIF2AK2) (DeBenedetti (1983) J Biol Che, 258: 14556-14562), but was unable to block PKR activation in cells and the phosphorylation of eIF-2a that occurs after adenoviral infection (Huang and Schneider (1990) PNAS 87: 7115-7119). 2-AP did increase the early adenovirus DNA-binding protein (DBP) levels 10 to 20-fold without increasing mRNA levels (Huang and Schneider (1990) PNAS 87: 7115-7119), consistent with an effect on cap-dependent translation.

Accordingly, in some embodiments, the method of producing a recombinant AAV comprising a transgene includes culturing cells of the present disclosure with 2-aminopurine. In some embodiments, the 2-aminopurine concentration is less than about 10 mM. In some embodiments, the 2-aminopurine concentration is less than about 5 mM. In some embodiments, the 2-aminopurine concentration is less than about 2.25 mM. In some embodiments, the 2-aminopurine concentration is less than about 1.25 mM. In some embodiments, the 2-aminopurine concentration is about 1 μM to about 1.25 mM. In some embodiments, the 2-aminopurine concentration is about 10 μM to about 1.25 mM. In some embodiments, the 2-aminopurine concentration is about 100 μM to about 1.25 mM. In some embodiments, the 2-aminopurine concentration is about 1.25 mM.

In specific embodiments, the cells of the present disclosure are contacted with 2-aminopurine about 24 hours post-infection with a recombinant adenovirus. In some embodiments, the cells of the present disclosure are contacted with 2-aminopurine about 20 hours post-infection with a recombinant adenovirus. In some embodiments, the cells of the present disclosure are contacted with 2-aminopurine about 12 hours post-infection with a recombinant adenovirus. In some embodiments, the cells of the present disclosure are contacted with 2-aminopurine about 30 hours post-infection with a recombinant adenovirus. In some embodiments, the cells of the present disclosure are contacted with 2-aminopurine about 36 hours post-infection with a recombinant adenovirus. In some embodiments, the cells of the present disclosure are contacted with 2-aminopurine about 48 hours post-infection with a recombinant adenovirus.

EXAMPLES

The following examples of the application are to further illustrate the nature of the application. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

Materials

Cells:

HEK293 Cells (American Type Culture Collection (ATCC), Manassas, VA, Catalog Number CRL-1573); PEAK-rapid (ATCC, Manassas, VA, Catalog Number CRL2828).

Tissue Culture Media and Reagents:

OptiMEM Medium (Thermo-fisher, Waltham, MA; Catalog Number 31985-062); DMEM, high glucose (Thermo-fisher, Catalog Number 10569-010); DMEM, No Phenol Red (Thermo-fisher; Catalog Number A14430-01); Hyclone Dialyzed Fetal Bovine Serum (Thermo-fisher; Catalog Number SH30079.03); 96-well TC plate (Corning, Corning NY; Catalog Number 3596); 6-well tissue culture plates, clear (Corning Catalog #3516); Culture Plate 96, Opaque White (PerkinElmer, Waltham, MA; Catalog Number 6005680); TrypLE Select Cell disassociation reagent (Thermo-fisher, Catalog Number 12563-011); Dulbecco's Phosphate Buffered Saline, no calcium, no magnesium, D-PBS (Thermo-fisher, Catalog #14190-144); Geneticin (G418) 50 mg/ml (Thermo-fisher, Catalog Number 10131-027); Puromycin dihydrochloride from *Streptomyces alboniger* (Sigma Aldrich P9620); T150 tissue culture flasks 150 mm2 (Corning, Catalog Number CLS430825); GlutaMax 100× (Thermo-fisher, Catalog Number 35050-061); Non-tissue culture treated 6-well culture plates (Corning, Catalog Number 351146); Hyperflask M vessels (Corning, Catalog Number 10030); 2.5% ClonaCell methylcellulose in DMEM (without L-glutamine and contains glucose, sodium pyruvate, and sodium bicarbonate) (StemCell Technologies, Vancouver, British Columbia, Canada Catalog Number 03899-DI).

Transfection Reagents:

Fugene-HD Transfection Reagent (Promega, Madison WI, Catalog Number E2311); Lipofectamine 3000 transfection reagent (Thermo-fisher Catalog Number L3000008); Deoxynucleotides (Millipore-Sigma, St. Louis, MO, Catalog Number D7295-2ML).

Tubes:

15 ml conical tubes (Corning, Catalog Number 430053); 1.5 ml screw cap tube (Sarstedt AG & Co. KG, Germany, Catalog Number 72.692.005).

Purification Kits and Assay Reagents:

Plasmid Spin Miniprep kit (Qiagen, Hilden, Germany, Catalog Number 27106); CHROMA SPIN™+TE-1000 Columns (Takara Bio USA, Mountainview CA, Catalog Number 636079); Dual-Glo Luciferase Assay System (Promega, Madison WI, Catalog Number E2940); Silver staining Kit (Thermo-fisher Catalog number 24600); Trizol Plus RNA purification kit with Phase-maker tubes (Thermo-fisher Catalog Number A33254); DNA-Free Kit (Thermo-fisher Catalog Number AM1906); Nucleospin Gel and PCR Cleanup Kit (Takara Bio USA, Catalog Number 740609.5).

Enzymes:

Spe I-HF (New England Biolabs, Ipswich, MA, Catalog Number R3133S); DNAse I grade II from bovine pancreas (Sigma-Aldrich, Catalog Number 10104159001); NEXT Ultra II Q5 Master Mix (New England Biolabs, Catalog Number M05445S).

Buffers and Chemicals:

CutSmart® Buffer (1× Buffer Components: 50 mM Potassium Acetate, 20 mM Tris-acetate, 10 mM Magnesium Acetate, 100 g/ml BSA, pH 7.9@25° C.) (New England Biolabs, Catalog Number B7204S); Benzonase Nuclease (Sigma-Aldrich, Catalog Number E1014-25K); 10× GeneAmp PCR Buffer I containing 1.5 mM MgCl2 (Thermo-fisher Catalog Number N8080006); Sodium Deoxycholate (Sigma-Aldrich, Catalog Number D6750-25g); 1M TRIS-HCL PH8.5 (Thermo-fisher, Catalog number T1085); 10× GeneAmp PCR Buffer I (Thermo-Fisher Catalog Number N8080006) [100 mM Tris-HCl, pH 8.3 (at 25° C.); 500 mM KCl; 15 mM MgCl2; 0.01% gelatin in autoclaved, deionized, ultrafiltered water]; 10% Pluronic F-68 (Thermo-Fisher Catalog Number 24040-032); Sheared salmon sperm DNA (10 mg/ml) (Thermo-Fisher Catalog Number AM9680); Virus Dilution Buffer (VDB) [1× GeneAmp PCR Buffer I, 2 μg/ml sheared salmon sperm DNA, and 0.05% Pluronic F-68); β-mercaptoethanol (Sigma-Aldrich, Catalog number M3148); Adenovirus formulation buffer (10 mM Tris (pH 7.4), 1 mM MgCl2, 75 mM NaCl, 5% sucrose, 0.02% Polysorbate 80, 0.1 mM EDTA, 10 mM histidine, 0.5% EtOH); 2-Aminopurine, nitrate salt (Sigma-Aldrich, Catalog number A2380), dissolved to 100 mM in DMEM+2% FBS.

RT-PCR Reagents:

SuperScript III First-Strand Synthesis System (Thermofisher Catalog Number 188080-051); Q5 Hot Start High-Fidelity 2× Master Mix (New England Biolabs, Catalog Number M0494S); 1% TAE Mini ReadyAgarose Gel with ethidium bromide (Bio-RAD, Catalog Number 1613016); Dark Reader Blue Light Transilluminator (Clare Chemicals, Dolores, CO, Catalog Number DR46B)

Digital Droplet PCR:

2× SuperMix for Probes (Bio-Rad Catalog Number 186-3026); DG32 AutoDG Cartridges (Bio-Rad Catalog Number 1864108); Auto Droplet Generator Oil in PBS (Bio-Rad Catalog Number 1864110); Droplet reader oil (Bio-Rad Catalog Number 1863004); Eppendorf twin.tec 96-Well PCR Plates (Catalog Number 951020346); Automated Droplet Generator (Bio-Rad Catalog number 186-4101); QX200 Droplet Reader (Bio-Rad Catalog number 186-4003); C1000Touch Thermal Cycler with Deep Well Reaction Module (Bio-Rad Catalog number 185-1197).

PrimeTime gPCR Assays:

A 20× stock of these assays consist of a forward and reverse PCR primer (at 1 μM) and 5' nuclease probe containing fluorescence quenchers ZEN and Black Hole Quencher 1 (3IABkFQ) and either FAM or HEX fluorescent Reporter Dyes (at 5 μM). Assays were synthesized by Integrated DNA Technologies, Inc., Coralville IA. Primer and Probe sequences for qPCR assays are as follows:

```
mCherry:
Primer 1
(SEQ ID NO: 36, 5'-CTGTTCCACGATGGTGTAGTC-3');

Primer 2
(SEQ ID NO: 37, 5'-TGAGGTCAAGACCACCTACA-3');

Probe
(SEQ ID NO: 38, 5'-FAM-TTGGACATC-ZEN-ACCTCCCACAACG

AG-3IABkFQ-3');

Adenovirus Exon 2 (Ad5E2):
Primer 1
(SEQ ID NO: 39, 5'-GGGTGATGCAGTAGAAGGTAAG-3');

Primer 2
(SEQ ID NO: 40, 5'-ATGAAGTTCGGCGGAGATG-3');

Probe
(SEQ ID NO: 41, 5'-HEX-TC TTGTTCC-Zen-CAGCGGTCCCAT

C-3IABkFQ-3');

P5 (P5 Promoter region of AAV):
Primer 1
(SEQ ID NO: 42, 5'-GTGGTCACGCTGGGTATTTA-3');

Primer 2
(SEQ ID NO: 43, 5'-GGGACCTTAATCACAATCTCGT-3');

Probe
(SEQ ID NO: 44, 5'-FAM-TTTGAAGCG-ZEN-GGAGGTTTGAACG

C-31ABkFQ-3');

AAV REP Gene:
Primer 1
(SEQ ID NO: 45, 5'-GTCCGTGAGTGAAGCAGATATT-3');
```

-continued

```
Primer 2
(SEQ ID NO: 46, 5'-TTCGATCAACTACGCAGACAG-3');

Probe
(SEQ ID NO: 47, 5'-FAM-TCTGATGCT-ZEN-GTTTCCCTGCAGA

CA-3IABkFQ-3');

AAV9 CAP Gene:
Primer 1
(SEQ ID NO: 48, 5'-CCGGGTCCAAGGTATTTGTAA-3');

Primer 2
(SEQ ID NO: 49, 5'-CTCAACCCAAGGCAAATCAAC-3');

Probe
(SEQ ID NO: 50, 5'-FAM-ACATCAAGA-ZEN-CAACGCTCGAGGT

CT-3IABkFQ-3');
and

Beta lactamase (Ampicillin resistance) gene:
Primer 1
(SEQ ID NO: 51, 5'-CCAGAAACGCTGGTGAAAGTA-3');

Primer 2
(SEQ ID NO: 52, 5'-CTCAAGGATCTTACCGCTGTTG-3');

Probe
(SEQ ID NO: 53, 5'-FAM-TGCACGAGT-ZEN-GGGTTACATCGAA

CT-3IABkFQ-3').
```

PAGE Electrophoresis:

4× NuPAGE LDS sample buffer (Thermo-Fisher, Catalog number NP0007); 4-12% Bis-Tris PAGE gel in 1× MOPS running buffer (Thermo-Fisher, Catalog number NP0322PK2); 20× NuPAGE MOPS SDS Running Buffer (Thermo-Fisher, Catalog number NP0001).

AAV Purification Buffer and Supplies:

0.2 μm PES membrane filter (Thermo-Fisher Catalog number 567-0020); 0.5×5 cm POROS GoPure chromatography column, pre-packed with POROS CaptureSelect AAVX resin (Thermo-fisher Catalog Number A36652); Amicon 15 100 kDa MWCO Filter (Millipore-Sigma Catalog Number UFC910024); CIM QA Disk 0.34 ml volume (BIA Separations, Slovenia); Buffer A (20 mM Tris pH7.5, 400 mM NaCl); Buffer B (25 mM Tris pH7.5, 40 mM NaCl, and 1.5 mM MgCl2); Buffer C (20 mM Sodium Citrate pH 2.5, 400 mM NaCl); Buffer D (100 mM Sodium Citrate, 10 mM Tris, pH 8.0); Buffer E (20 mM BTP pH10.0, 0.001% Pluronic F68, 10 mM NaCl); Buffer F (20 mM Bis-TRIS Propane pH 10.0, 0.001% Pluronic F68, 400 mM NaCl); Bis-TRIS Propane (BTP) (Millipore Sigma Catalog Number B4679).

Other Equipment:

AKTA Explorer FPLC system (GE Healthcare Life Sciences, Marlborough, MA); AKTA Purifier system (GE Healthcare Life Sciences); Envision multilabel reader Model 2104 (PerkinElmer, Waltham, MA).

Identification and Recombinant Expression of SR21 Recombinase

Using BLAST searches of the Non-redundant protein database at NCBI with SPBeta c2 integrase protein (Query, SEQ ID NO:1) as a query, a putative serine recombinase (Sbjct, SEQ ID NO:2) was identified in the genome of *Bacillus safensis* strain CCMA-560 with 64% sequence identity at the protein level (FIG. 1). The putative serine recombinase or integrase is part of a putative prophage insertion. This recombinase was named SR21 (Serine Recombinase 21). The DNA sequence encoding SR21 is shown in SEQ ID No:3.

A bacterial strain that is closely related to CCMA-560 that does not contain the prophage insertion (the "Fairview" strain) was identified by BLAST searches of sequence databases at NCBI using a CCMA-560 DNA sequence from the 3' end of the recombinase coding region and beyond as a query (SEQ ID NO:58) (FIG. 2). A DNA sequence of the Fairview strain corresponding to the upstream and downstream sequences of the putative prophage insertion site in CCMA-560 is referred to herein as the "pre-insertion sequence," and is shown in SEQ ID NO:4. Using this sequence (SEQ ID NO:4) as a query to BLAST the genomic sequence of CCMA-560 strain identified the other Prophage-host DNA junction 94 kb upstream. The sequences of the right and left prophage-host DNA junctions of *Bacillus safensis* strain CCMA-560 are shown in SEQ ID NO:5 and SEQ ID NO:6, respectively.

SR21 recombinase attP and attB sequences were reconstructed from the host DNA junctions (SEQ ID NO:5) and (SEQ ID NO:6), respectively by exchanging sequences upstream of a central identical region ("ACTGACAAAGCGGT") (SEQ ID NO:54) and picking the central dinucleotide and att site boundaries that maximized the dyad symmetry: attP (SEQ ID NO:7); attB-CCMA-560 (SEQ ID NO:8). The attB sequence (SEQ ID NO:9) derived from the host DNA junction (SEQ ID NO:4) of the Fairview strain of *Bacillus safensis* contains two mismatches relative to the reconstructed attB sequence from strain CCMA-560 (SEQ ID NO:8). FIG. 3 shows the alignment of attP with these two alternate attB sequences, highlighting positions of dyad symmetry.

Measuring Recombinase Activity in Mammalian Cells

A vector (P175) (SEQ ID NO:10) was constructed by Gene Synthesis (GENEWIZ, Plainfield, N.J.) to express SR21 recombinase in mammalian cells under control of the CMV promoter and followed by an SV40 polyadenylation signal. The SR21 recombinase open reading frame is the same as SEQ ID NO:3 except that the bacterial translation initiation codon "TTG" is replaced by an "ATG", and three point-mutations were introduced to destroy restriction endonuclease recognition sites. These changes in the open reading frame do not result in any change in the encoded SR21 recombinase amino acid sequence.

Figure 4:
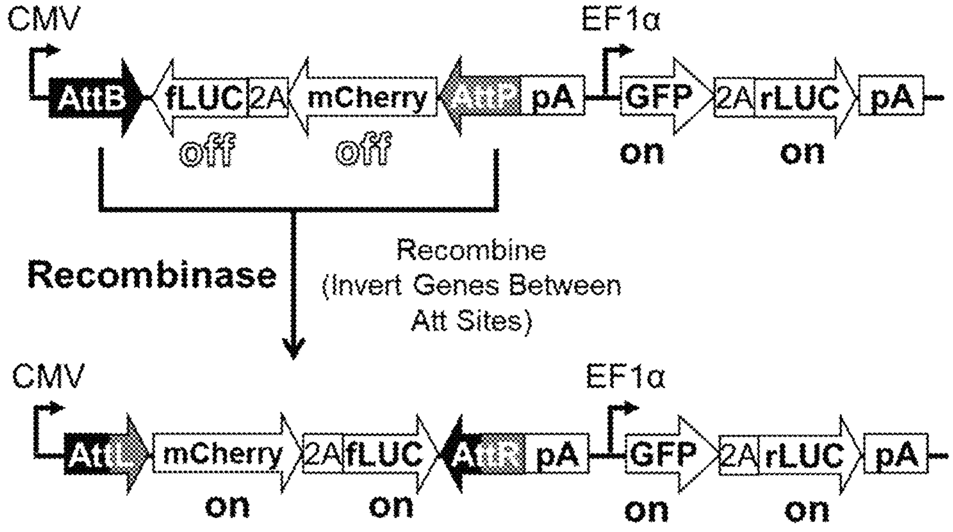
FIG. 4 illustrates recombinase activation of reporter genes. Plasmid P41 encodes two reporter gene transcripts. The first driven by the EF1α promoter is constitutively active and encodes a fusion protein between green fluorescent protein (GFP) and *renilla* luciferase linked by a self-cleaving F2A peptide linker. The second transcript driven by CMV includes the SR21 Recombinase attB site (SEQ ID NO:9) followed by an inverted fusion protein coding region encoding mCherry and firefly luciferase linked by the P2A self-cleaving peptide linker and a SR21 attP site. Neither luciferase nor mCherry is expressed since they are in the opposite orientation relative the promoter. When SR21 recombinase is expressed, the attB and attP sequences are recombined, which results in the inversion of the reporter genes and expression of firefly luciferase and mCherry.

A recombinase reporter plasmid (P41) was also constructed by gene synthesis (GENEWIZ, Plainfield, N.J.) (SEQ ID NO:11; FIG. 4). It encodes a constitutively expressed green fluorescent protein (GFP)—self-cleaving F2A—*Renilla* luciferase (rLUC) fusion protein driven by the EF1α promoter. It also encodes recombinase activated—mCherry-self cleaving P2A-firefly luciferase (fLUC) reporter gene flanked by SR21 attP (SEQ ID NO:7) and attB (SEQ ID NO:9) signals in the antisense orientation relative to the CMV promoter. When SR21 recombinase recombines the attP and attB signals, the coding region is inverted into the sense orientation and the mCherry-P2A-fLUC protein is expressed (See FIG. 4).

To measure SR21 recombinase activity in human cells, 75,000 HEK293 cells were plated into each well of 96-well tissue culture plates in 100 of high-glucose DMEM+10% Fetal Bovine Serum. The recombinase reporter plasmid (P041) the SR21 Recombinase expression plasmid (P175)+ deoxynucleotides (to normalize DNA amounts) were complexed with Fugene-HD transfection reagent in OptiMEM medium for 15 minutes at room temperature as shown in Table 1 and transfected into triplicate wells of the plated cells. Plates were incubated at 37° C. for 48 hours.

TABLE 1

Transfection Conditions

| Sample | P41 Recombinase Reporter | P175 Recombinase Expression Plasmid | Deoxynucleotides | Fugene-HD | OptiMEM |
|---|---|---|---|---|---|
| 1 | 4 μl (100 ng) | none | 12 μl (300 ng) | 1.2 μl | 22.8 μl |
| 2 | 4 μl (100 ng) | 4 μl (100 ng) | 8 μl (200 ng) | 1.2 μl | 22.8 μl |

Firefly Luciferase (fLUC) and *Renilla* luciferase (rLUC) was assayed sequentially in transfected wells using the Dual Glo assay kit from Promega. Medium was removed from the transfected wells of the tissue culture plate and 100 μl of a 1:1 mixture of DMEM medium (without phenol red) and the Dual Glo luciferase+fLUC substrate was added. The plate was incubated at room temperature for 10 minutes. The lysate was transferred to an opaque white 96-well plate. fLUC activity was measured using the Envision multilabel reader. Next, 50 μl per well of the Stop-and-Glo buffer+ *Renilla* substrate was added and the plate was incubated with gentle shaking for 10 minutes. The *Renilla* luciferase signal was read on the same Envision reader.

Results:

The recombinase reporter produced 1535-fold-more firefly luciferase when co-transfected with the recombinase expression plasmid than when co-transfected with deoxynucleotides instead (Table 2). This difference is not explained by different transfection efficiencies since *Renilla* luciferase (rLUC) activity was 5-fold higher in the reporter alone transfection. This data demonstrates that SR21 recombinase is highly active in human cells and this result is representative of three independent experiments.

TABLE 2

Recombinase Activity in HEK293 Cells

| Sample | Description | fLUC | rLUC | Fold-Increase in fLUC Activity |
|---|---|---|---|---|
| 1 | Reporter alone | 4.3E03 ± 1.2E03 | 1.4E07 ± 2.6E06 | |
| 2 | Reporter + Recombinase | 6.6E06 ± 3.9E05 | 3.4E06 ± 1.6E05 | 1535 |

Constructing REP/CAP+Transgene Plasmid

Large-scale production of AAV in mammalian cells may be possible if the AAV replication (REP) and Capsid (CAP) genes could be stably integrated and later induced to produce AAV in high density cultures. However, the expression of REP proteins is toxic, making it difficult to develop stable cell lines in hosts where REP genes are expressed such as those that express the Adenovirus E1 genes such as HEK293 cells. Wild-type AAV encodes four REP proteins with overlapping reading frames that result from the use of two promoters and alternate splicing. Hence, the use of an inducible promoter to control REP expression is not straightforward. Previous work demonstrated that a "Stop Cassette" inserted into the REP coding region inside an artificial intron allowed stable cell lines to be generated in HEK293 cells (Qiao et al. (2002) J. Virol. 76: 13015; Yuan et al. (2011) Hum Gene Therap. 22: 613-624). Excision of the Stop Cassette using Cre Recombinase delivered by adenovirus infection restored REP expression and initiated AAV replication of an ITR-flanked transgene. In this example, an improved version of a Recombinase-activated REP gene in the context of a REP/CAP expression cassette in a plasmid that contained an ITR-flanked transgene was constructed.

An AAV REP/CAP9 expression cassette (SEQ ID NO:13) was constructed using the AAV2 REP gene (bp 190-2202 of human AAV2, NC_001401.2), followed by the AAV9 CAP open reading frame (AY530579.1), the AAV2 polyadenylation signal (bp 4411-4466, NC_001401.2), and a second copy of the AAV2 REP P5 promoter (bp 190-313, NC_001401.2).

Splice site prediction software (NetGene2 at www.cbs.dtu.dk/services/NetGene2/; Brunak, S., Engelbrecht, J., and Knudsen, S.: Prediction of Human mRNA Donor and Acceptor Sites from the DNA Sequence, Journal ofMolecular Biology, 1991, 220, 49-65.) was used to pick a suitable location to insert an intron from the Human 3-Actin gene into the REP coding region. The intron was inserted downstream of nucleotide number 1052 in AAV2 (NC_001401.2) in a region that is common to all four REP transcripts. Both the intron and the insertion location are different than that used by Qiao et al. (2002) J. Virol. 76: 13015). The Stop Cassette (below) was subsequently inserted between the upstream and downstream halves of this β-Actin intron (SEQ IDs 14 and 15, respectively).

STOP Cassette

The transcriptional STOP cassette (SEQ ID NO:16) was composed of the following elements:

SR21 attP (SEQ ID NO:7)

A strong splice acceptor (SEQ ID NO:17) (NC_000086.7, nucleotides 53001998 to 53002138 from the mouse HPRT gene, plus a 29 nt region from the Human Agouti Signaling protein (NC_000020.11, nucleotides 34262765 to 34262793). This was included to prevent the STOP cassette from being splice out of primary mRNA transcripts.

A neomycin phosphotransferase expression cassette (SEQ ID NO:18) was driven by a mammalian promoter (mouse phosphoglycerate kinase 1) and a bacterial (Lac zya) promoter and followed by a polyadenylation signal from SV40. This gene confers resistance to neomycin and kanamycin in mammalian and bacterial cells, respectively.

A sequence from the human β-globin gene downstream of the polyadenylation signal that encodes a self-cleaving RNA motif that is important for efficient transcription termination (Teixeira et al. (2004) Nature 432: 526-30; SEQ ID No:19).

SR21 attB (SEQ ID NO:8).

AAV Transgene

An AAV Inverted Terminal Repeat (ITR)-flanked transgene was encoded in the P439 vector (SEQ ID NO:12) downstream of the AAV REP/CAP region. The 130 bp ITR (SEQ ID NO:20) was derived from the 3' AAV2 ITR (Nucleotides 4535-4664, NC_001401.2) and was inserted upstream of the HPRT-E2A-mCherry transgene and reverse direction 3' of the transgene.

The transgene consisted of the Human EF1-alpha promoter (including exon 1, intron 1, and part of exon 2) (SEQ ID NO:21), a sequence encoding a mCherry—self-splicing E2A linker—Human HPRT fusion gene (SEQ ID NO:22), and a polyadenylation signal from the Herpes Simplex Virus Thymidine Kinase Gene (SEQ ID NO:23).

Insulators

The REP/CAP and ITR-Transgene elements were flanked by genomic elements that block chromatin-associated repression of gene expression (Kwaks et al. (2003) Nature Biotechnology 21: 554-558; Kwaks et al. (2003) Nature Biotechnology 21: 822): Human anti-repressor element 40 (AY190756.1, SEQ ID NO:24) and Mouse anti-repressor element 40 (SEQ ID NO:25).

Plasmid Backbone

The plasmid backbone contains the following elements:

A mammalian puromycin resistance gene cassette constructed from the Herpes virus thymidine kinase gene promoter (SEQ ID NO:26), the puromycin N-acetyl transferase coding region (SEQ ID NO:27), and a polyadenylation signal from bovine growth hormone gene (SEQ ID NO:28).

An Epstein Barr Virus (EBV) OriP replication origin fragment (SEQ ID NO:29), which represents a composite of the 'Dyad Symmetry' region and the 'Family of Repeats' region of EBV pUC57 vector sequence encoding plasmid replication origin and ampicillin resistance gene (SEQ ID NO:30).

The sequence of the complete Plasmid P439 is given in SEQ ID NO:12.

Test Efficiency of STOP Cassette Removal by SR21 Recombinase

To test whether the Stop Cassette could be precisely removed by SR21 Recombinase in human cells, vector P439 (SEQ ID NO:12) and the SR21 Recombinase expression vector P175 (SEQ ID NO:10) were co-transfected into PEAK-Rapid cells using Lipofectamine 3000 according to manufacturer's instructions and were cultured in media containing DMEM and 10% FBS for three days at 37° C. in 5% CO2. Media was removed, cells were washed once with D-PBS and then incubated with TrypLE for 5 minutes at 37° C. Cells were transferred to a sterile microfuge tube, pelleted by centrifugation, washed once with 1 ml D-PBS and pelleted again. Episomal plasmids were recovered by alkaline lysis using the Qiagen Spin Miniprep kit designed for isolating plasmids from bacteria.

To destroy unrecombined plasmid DNA, an aliquot of the recovered DNA was digested with enzyme Spe I-HF in 1× CutSmart Buffer at 37° C. Ihour and 80° C. 20 minutes. The recovered DNA was subjected to PCR amplification with primers P349F3 (SEQ ID NO:32) and P349R9 (SEQ ID NO:33) using NEXT Ultra II Q5 Master Mix with the following cycling conditions: 98° C. 1 min; 35× (98° C. 10s, 72° C. 10s); 5 min 72° C. A single PCR product of the predicted size was observed when subjected to electrophoresis on a 1% agarose gel. The PCR product was purified by size exclusion chromatography using a CHROMA SPIN™+ TE-1000 Column. The PCR product was sequenced using the same primers used for PCR (GeneWiz). The resulting sequence (SEQ ID NO:34) demonstrated that the STOP cassette had been precisely removed from plasmid P439 by SR21 recombinase through recombining the attP (SEQ ID NO:7) and attB (SEQ ID NO:8) sequences, producing an attL recombined sequence (SEQ ID NO:35).

Construction of Recombinant Adenovirus Serotype 5 Expressing SR21 Recombinase

Recombinant ΔE1/ΔE3 Adenovirus serotype 5 (Ad5) virus was generated at Batavia Biosciences (Leiden, the Netherlands) by a homologous recombination procedure in PER.C6 cells (Fallaux et al. (1998) Hum Gene Ther. 9: 1909-1917) as previously described for production of E1 deleted vectors (Havenga et a. (2001) J. Virol 75:3335-3342) except that a modified cosmid (pWE/Ad5.AflII-rITRsp.ΔE3, U.S. Pat. No. 6,340,595B1) lacking the E3 region was used. Co-expression of PER.C6 cells with this cosmid and plasmid P321 (SEQ ID NO:31) that contains the Ad5 sequence from 1 to 454 (left ITR and packaging signal), a cassette for transgene expression containing the cytomegalovirus (CMV) promoter (nt −672 to +15), the SR21 Recombinase coding region, simian virus 40 (SV40) polyadenylation signal (NC_001669.1, nt 2550 to 2774) and a second Ad5 sequence ranging from nt 3511 to 6095). Homologous recombination between the P321 Ad5 sequence (nt 3511-6095) and cosmid pWE/Ad5.AflII-rITRsp.ΔE3 in PER.C6 cells produces a recombinant adenovirus. Purified virus stocks were obtained by a two-step CsCl-gradient banding procedure and the isolated virus stocks were dialyzed into the adenovirus formulation buffer (10 mM Tris (pH 7.4), 1 mM MgC2, 75 mM NaCl, 5% sucrose, 0.02% Polysorbate 80, 0.1 mM EDTA, 10 mM histidine, 0.5% EtOH).

Stable Cell Line Generation

Plasmid P439 (SEQ ID NO:12) was transfected into adherent PEAK-RAPID cells using Lipofectamine 3000 according to manufacturer's instructions and cultured in a T25 flask in DMEM+10% FBS+0.05 mg/ml Geneticin at 37° C. After 24 hours, cells were treated with TrypLE and transferred to a T75 flask containing DMEM+10% FBS+0.05 mg/ml Geneticin+0.5 μg/ml puromycin. Cells were split 1:10 weekly into the same medium for two successive weeks. At the third week post transfection, the cells were split 1:10 weekly for three weeks into media containing DMEM+10% FBS+0.05 mg/ml Geneticin+5.0 μg/ml puromycin.

Single-cell clones were produced by diluting cells into 1% ConaCell Methylcellulose in DMEM+30% FBS+1× GlutaMax+5 μg/ml puromycin+0.05 mg/ml Geneticin, plating into non-tissue culture treated 6-well plates, and culturing at 37° C. for three weeks. Using a pipettor, clones were transferred from methylcellulose plates into 96-well TC-treated plates containing DMEM+10% FBS+0.05 mg/ml Geneticin+5.0 μg/ml puromycin. Clones were expanded in the same medium by standard methods.

Screening Clones

To screen clones for AAV production, cells were plated in duplicate into 96-well plates in 100 μl DMEM+10% FBS and incubated overnight at 37° C. SR21 Adenovirus was diluted to 1E8 viral genomes per ml in serum-free DMEM. The media from the plated cells was replaced with 100 μl diluted adenovirus and the plate was incubated at 37° C. for four days. Cells were lysed by adding 10 of the following mixture: 5% Deoxycholate in PBS+10 units Benzonase. The plate was incubated at 37° C. 2 hours. The plate was centrifuged at 3000 rpm for 5 minutes to pellet cellular debris, and AAV viruses in the supernatant were quantitated by digital droplet PCR (ddPCR).

Digital Droplet PCR (ddPCR)

ddPCR quantitation was based on the method described by Lock et al. (2014) Human Gene Therapy methods 23: 115-125. Two 1 of the lysate was DNAse digested in 20 reactions containing 1× PCR buffer+20 mM Tris pH 8.5+8 units DNAse I at 37° C. for 1 hour 96-well plates in a thermocycler. 2 μl of the DNAse digested samples were diluted with 98 Virus Dilution Buffer (VDB) and 2 μl of this dilution was added to ddPCR reactions containing 1× PCR SuperMix+1× PCR Primer/Probe for the mCherry transgene (See Materials section). ddPCR droplets were formed using the Bio-Rad automated droplet maker. PCR cycling was as follows: 95° C. 10 min; 42× (94° C. 30s, 60° C. 1 min, 72° C. 15s all three at cycling time of 2° C. per s); 98° C. 10 min; 4° C. hold. FAM fluorescence was detected on the Bio-Rad droplet reader as per manufacturer's instructions. The clones that produced the highest DNAse-resistant particles as detected as FAM-fluorescence positive droplets were subjected to expansion and further screening.

Screening Clones—Second Assay 1.25E6 cells of clones to be screened were plated into single wells of a 6-well plate in 3 mls DMEM+10% FBS and incubated for 2 days at 37° C. The growth medium was replaced with 3 mls DMEM+10% FBS containing 5E8 Ad5-SR21 virus particles. Plates were returned to 37° C. to incubate for 3 days. Cells and media were transferred to 15 ml tubes and subjected to 3 freeze thaw cycles (Dry ice/37° C. incubation) followed by centrifugation at 3000 rpm for 5 minutes to pellet cellular debris. 2 μl of each sample was subjected to DNAse digestion and ddPCR quantitation with the mCherry assay as described above. P439C4 cells produced the most AAV upon infection with Ad5-SR21 virus and was selected for further characterization (Table 3).

TABLE 3

AAV Production in Screening Assays

| Clone # | Total AAV (DNAse-Resistant Particles) |
|---|---|
| clone 1 | 4.4E+08 ± 7.6E+07 |
| clone 3 | 2.5E+09 ± 3.4E+08 |
| clone 4 | 4.4E+09 ± 5.6E+07 |
| clone 5 | 1.8E+09 ± 1.9E+08 |
| clone 12 | 7.5E+08 ± 9.8E+07 |
| clone 18 | 1.6E+08 ± 2.6E+07 |
| clone 20 | 9.8E+07 ± 1.4E+07 |
| clone 25 | 1.2E+09 ± 6.4E+07 |
| clone 28 | 1.3E+08 ± 1.2E+07 |
| clone 32 | 1.5E+09 ± 1.3E+08 |
| clone 36 | 2.8E+08 ± 3.0E+07 |
| clone 41 | 1.0E+09 ± 8.9E+07 |

Time Course Experiment

A new experiment was conducted to determine the kinetics of AAV production and secretion in the culture media at two different growth temperatures. Two mls of a non-enzymatic dissociation solution was added to PBS-washed monolayers of P439-C4 cells in T150 flasks and the flask was incubated at 37° C. for 5 minutes. Flasks were washed with 8 mls of DMEM+10% FBS and the cells were transferred to 50 ml centrifuge tube. Cells were centrifuged at 1500 rpm for 5 minutes and the pellets were resuspended in DMEM+2% FBS. Cells were diluted to 1.25E6 cells per ml in the same medium. Four mls of cell were plated into each well of four 6-well plates. 1 ml (2E8 vp) of Ad5-CMV-SR21 adenovirus in DMEM+2% FBS was added to wells. Two plates were incubated at 37° C. and two plates were incubated at 32° C. at 5% CO2. Each day for 8 days, cells and media were recovered using a cell scraper to dislodge attached cells and samples were transferred to 15 ml conical tubes. Tubes were spun for 5 minutes at 3000 rpm and an aliquot was transferred to a 1.5 ml screw cap tube and frozen at −20° C. until ddPCR assays.

Samples were DNAse treated in duplicate as described above and three serial dilutions were made in VDB for each DNAse-treated sample. Samples were quantitated in ddPCR reactions containing 1× PCR Master Mix+1× mCherry-FAM Assay+1× Ad5E2-HEX Assay (See Materials section). ddPCR was performed as described above.

Results:

Adenovirus and AAV in the cell culture medium increased over the 8-day time course (Table 4). Adenovirus replication was slower at 32° C. resulting in higher AAV production, probably as a result of delayed adenovirus cytopathic effect. AAV production at 32° C. exceeded 14,000 genome copies per cell.

TABLE 4

AAV and Adenovirus Yields Over 8-Day Time Course

| Days Post-Infection | AAV GC/Cell | | Ad5 GC/Cell | |
|---|---|---|---|---|
| | 32° C. | 37° C. | 32° C. | 37° C. |
| 1 | 4 ± 1 | 22 ± 0 | 8 ± 1 | 161 ± 4 |
| 2 | 11 ± 2 | 174 ± 26 | 223 ± 14 | 1319 ± 292 |
| 3 | 2009 ± 137 | 803 ± 110 | 2028 ± 155 | 4941 ± 75 |
| 4 | 4275 ± 274 | 975 | 2600 ± 168 | 5806 ± 159 |
| 5 | 7406 ± 309 | 1672 ± 49 | 5041 ± 446 | 12000 ± 442 |
| 6 | 7469 ± 75 | 4109 ± 214 | 4781 ± 610 | 33344 ± 1781 |
| 7 | 10313 ± 619 | 5034 ± 75 | 8344 ± 663 | 20594 ± 1547 |
| 8 | 14031 ± 221 | 5563 ± 88 | 13313 ± 177 | 22875 ± 442 |

Hyperflask Cultures 8.3E07 P439C4 cells were plated into two Hyperflask M vessels in 550 mls of DMEM+10% FBS+0.5 μg/mL Puromycin, +50.0 μg/mL G418 and incubated at 37° C. for 3 days. Density after 3 days growth was estimated to be 3.6E8 cells per flask. Flasks were infected at 40 MOI (1.4E10 vp) or 20 MOI (7.2E09 vp) by diluting virus in 550 mls of DMEM+10% FBS and replacing the medium in the hyperflasks with the diluted virus. The cells were incubated at 32° C. at 5% CO2 for 7 days. Supernatants were collected from the infections after 7 days and were clarified by passing through a 0.2 m PES membrane filter.

AAVX Purification

A 0.5×5 cm POROS GoPure chromatography column, pre-packed with POROS CaptureSelect AAVX resin to a bed volume of 1 mL, attached to an AKTA Explorer FPLC system was equilibrated with 10 column volumes (CV) buffer A (20 mM Tris pH7.5, 400 mM NaCl) at a flow rate of 3 ml/min. Virus suspension was loaded at a flow rate of 4.5 mL/min, followed by 10 mL of Buffer A to wash out unbound sample. An on-column DNA digestion was performed by equilibrating the column with 5 ml of a low salt benzonase buffer, buffer B (25 mM Tris pH7.5, 40 mM NaCl, and 1.5 mM MgCl2), then loading the column with 15 mls buffer B containing 250 units/ml Benzonase. The column was then incubated at room temperature for 30 minutes, followed by a 15 CV wash with buffer A. Virus was eluted with 15 CV buffer C (20 mM Sodium Citrate pH 2.5, 400 mM NaCl) in 0.5 mL fractions that were immediately neutralized with 25 μL of 500 mM Bis-TRIS Propane pH 10.0. Single peak elution observed. All fractions under the curve were pooled, concentrated and buffer exchanged into buffer D (100 mM Sodium Citrate, 10 mM Tris, pH 8.0) using an Amicon 15 100 kDa MWCO (Cat #UFC910024, Fisher) using three rounds of buffer addition/centrifugation. The buffer-exchanged and concentrated affinity chromatography product was subjected to anion exchange chromatography to further purify AAV away from empty capsids.

Ion Exchange Chromatography

The affinity chromatography product (viral suspension) was diluted to 45 mL in buffer E (20 mM BTP pH10.0, 0.001% Pluronic F68, 10 mM NaCl) and loaded onto a CIM QA Disk (BIA Separations, 0.34 ml volume) at a flow rate of 2 ml/min on an AKTA Purifier system (GE Healthcare Life Sciences). Column was washed with 10 CV of sterile filtered Buffer E (20 mM BTP pH10.0, 0.001% Pluronic F68, 10 mM NaCl). Virus was eluted over a 60 CV gradient from 100% Buffer E to 100% Buffer F (20 mM Bis-TRIS Propane pH 10.0, 0.001% Pluronic F68, 400 mM NaCl), collecting 0.5 mL fractions. All fractions under the curve were pooled and concentrated using an Amicon 15 100 kDa MWCO (cat #: UFC910024, Fisher) by a 5 min centrifugation at 2000×g and buffer exchanged into buffer D (100 mM Sodium Citrate, 10 mM Tris, pH 8.0).

Protein Visualization

2 μL of concentrated eluate was heat denatured (95° C. for 10 min) in NuPage LDS sample buffer (4×) supplemented with 5% β-mercaptoethanol and electrophoresed on 4-12% Bis-Tris PAGE gel in 1× MOPS running buffer. The gel was subjected to silver staining according to the manufacturer's instructions.

ddPCR

Viral concentration was measured by digital droplet PCR using the mCherry assay as described above.

Results

Figure 5:
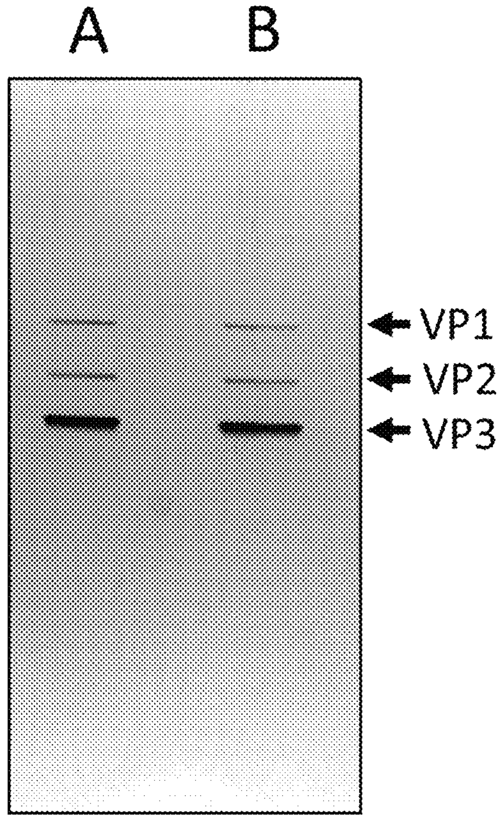
FIG. 5 shows AAV capsid proteins in purified recombinant AAV samples produced according to an embodiment of the application. Samples were purified from cells stably transfected with plasmid P439, grown and infected in Hyperflask vessels at 20 MOI (A) and 40 MOI (B) and were subjected to PAGE and silver staining.
Figure 6:
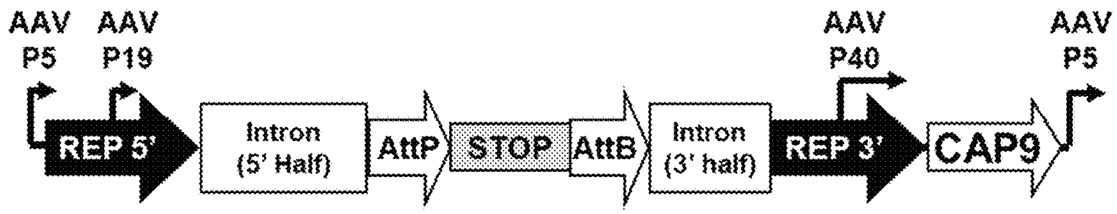
FIG. 6 illustrates a rep/cap expression cassette with an artificial intron having a stop cassette inserted therein, according to an embodiment of the application.
Figure 7:
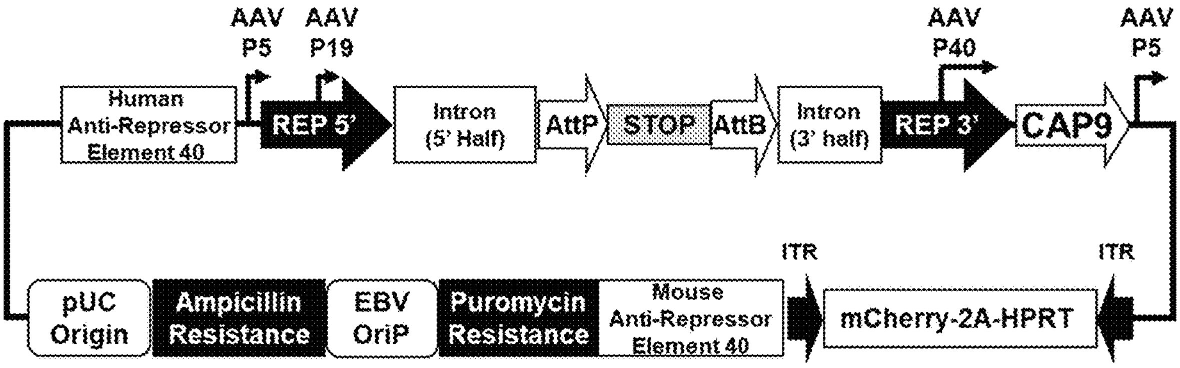
FIG. 7 illustrates a vector (plasmid P439) according to an embodiment of the application.

Infection and growth of P439C4 cells in Hyperflask vessels produced 1.9E13 and 7.0E13 genome copies (GC) when infected at 20 and 40 MOI, respectively. This corresponds to 5.2E4 and 1.9E5 GC per cell for the 20 and 40 MOI infections, respectively. The purity of the virus samples was examined through PAGE electrophoresis and silver staining. Only three bands corresponding to the sizes expected for the three AAV9 capsid isoforms (VP1, VP2, and VP3) were visible (FIG. 5). The capsid proteins (VP1 (87 kDa), VP2 (72 kDa), and VP3 (62 kDa) are present in the expected stoichiometry of approximately 1:1:10 as reported previously for other recombinant AAV vectors (Daya and Berns (2008) Clin Microbiol Rev. 21: 583-593).

Measuring the Level of Mispackaged DNA

Sequences encoding AAV REP or CAP genes and prokaryotic sequences derived from plasmid vectors used during production can be non-specifically packaged into AAV particles and represent potential safety risks when used for gene therapy (see, e.g., Schnodt and Buning, *Hum Gene Ther Methods.,* 2017; 28(3):101-108). Risks include the generation of replication-competent AAV through homologous recombination, capsid gene expression triggers cytotoxic T lymphocyte reactions, and immune system recognition of prokaryotic sequences resulting in inflammatory responses and/or gene silencing. Encapsidated rep, cap, and prokaryotic sequences of 2%, 0.4%-1.0%, and 1.3%-6.3%, respectively have been reported in purified recombinant AAV preparations produced by triple transfection or from produced cell lines (Nony et al. (2003) J. Virology 77: 776-781; Gao et al. (2008) Molecular Therapy 16: S105; Chaudeuf et al. (2005) Molecular therapy 12: 744-753).

To determine the level of mispackaging associate with the producer system described above, the abundance of four sequences in the transfected vector (outside of the ITR-flanked transgene) was determined by ddPCR: a) the P5 promoter; b) the AAV REP gene; c) the AAV9 CAP gene; and d) the beta-lactamase (ampicillin resistance) gene. Purified virus preparations from the 20 and 40 MOI hyperflask cultures previously described were DNAse digested in triplicate, serially diluted in VDB and subjected to ddPCR. The concentration of virus particles containing these sequences were expressed as percentages of AAV particles containing the mCherry transgene (Table 5). The highest encapsidation rate of 0.04% was that of the P5 promoter in the virus A prep (produced with 20 MOI of infecting recombinant adenovirus). However, the P5 encapsidation rate in prep B (40 MOI) where AAV yield was much higher was only 0.007%. REP, CAP, and Ampicillin gene sequences were the same or lower. CAP levels were 0.007%-0.009%, which are lower than the 0.016%-0.021% cap encapsidation rate previously reported for four clinical lots of recombinant AAV2 produced for a hemophilia B gene therapy trial (Hauck et al. (2009) Molecular Therapy 17: 144-152.) Thus, the method described here for producing and purifying recombinant AAV results in a very low rate of mispackaged DNA in line with what may be required for clinical gene therapy programs.

TABLE 5

Abundance of Non-Transgene Sequences Packaged in Purified Virus

| | P5 Promoter | REP | CAP | Ampicillin |
|---|---|---|---|---|
| Virus A (20 MOI) | 0.0398% ± 0.0023% | 0.0078% ± 0.0003% | 0.0092% ± 0.0002% | 0.0051% ± 0.005% |
| Virus B (40 MOI) | 0.0074% ± 0.0032% | 0.0005% ± 0.0002% | 0.007% ± 0.0001% | 0.0003% ± 0.0001% |

The mean percentage of DNAse-resistant particles standard deviation for four probes relative to mCherry transgene containing particles is shown for analyses of two AAV vector preparations.

RT-PCR Analysis of RNA Splicing of the REP Gene after Stop Cassette Excision

To determine whether the intron inserted into the REP gene in construct P439 is accurately spliced when the STOP cassette is excised, an RT-PCR experiment was conducted.

Ten million cells from a stable pool of P439 in PEAK-RAPID cells were pelleted by centrifugation and resuspended in 15 mls of DMEM+2% FBS+1E9 Ad5-CMV-SR21 virus particles. Cells were plated into a T75 flask and incubated at 37° C. for forty-eight hours. Cells were detached using a cell scraper. Media and cells were transferred to a 15 ml centrifuge tube and were centrifuged at 1500 rpm for 10 minutes to pellet the cells. RNA was purified from the cell pellet using the Trizol Plus RNA purification kit with Phase-maker tubes.

To remove any contaminating DNA, 31 g of RNA was treated with 1 μl of DNAse from the DNA-Free kit in 1× digestion buffer at 37° C. for 30 minutes. 5 μl of the DNAse inactivation slurry was added and the sample was inverted several times during a 2-minute incubation. The RNA sample was centrifuged at 10,000×g for 5 minutes and the RNA was transferred to a new sterile tube.

The RNA was reverse transcribed with the SuperScript III First Strand Synthesis System. 80 g RNA, 1 μl 50 μM Oligo-DT, and 1 μl 10 mM dNTPS were mixed in a sterile tube and incubated at 65° C. for 5 minutes and on ice for 2 minutes. Ten 1 of a 2× mixture was added (2× RT buffer, 10 mM MgCl2, 20 mM dithiothreitol, 0.5 1 RNAse-out, and 0.5 1 Reverse Transcriptase). Mock RT reactions were identical except that reverse transcriptase was replaced with water. The reactions were incubated at 50° C. for 50 min and on ice for 2 minutes. One 1 RNAse H was added and samples were incubated for 20 minutes at 37° C.

Fifty μl PCR reactions contained 1 μl of reverse transcribed RNA, 25 μl Q5 Hot Start High-Fidelity 2× Master Mix, and 0. μM of two primers. Reactions were subjected to thermocycling as follows:

98° C. 1 min; 35 cycles of (98° C. 10s, 69° C. 10s, 72° C. 36s); 5 min 72° C.

Five μl of the reactions were resolved on 1% Agarose gels in 1×TAE buffer and ethidium bromide. Bands were visualized under blue light illumination on the Dark Reader transilluminator. DNA was recovered from excised bands using the Nucleospin gel and PCR cleanup kit. DNA was sequenced at GeneWiz (South Plainfield, N.J.) with the PCR primers using cycle-sequencing and dye-terminator chemistry.

Results

Figure 8:
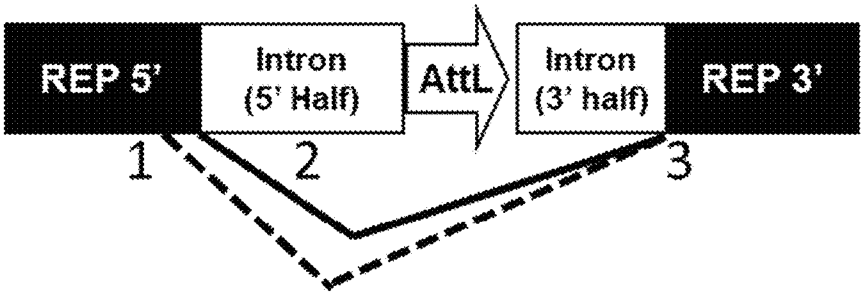
FIG. 8 illustrates the position and sequence of RNA splice sites identified in P439 by RT-PCR. The top drawing represents the structure of the REP gene after STOP cassette excision. The 5' and 3' halves of REP are separated by the upstream half of the beta-Actin intron (SEQ ID NO:14), the SR21 AttL element (SEQ ID 35), and the downstream half of beta-Actin intron (SEQ ID NO:15). Splicing between (2) the beta-Actin splice donor (SEQ ID NO:71) and (3) beta-Actin splice acceptor (SEQ ID NO:72) are denoted by the solid line. Splicing between (1) an upstream splice donor in the 5'REP sequence (SEQ ID NO:64), and (3) the 3' beta-Actin acceptor (SEQ ID NO:72) are shown with dotted lines. The sequences of splice donor and acceptors are shown below. Lower case sequence denotes the intron sequence.

PCR reactions from mock-RT templates did not produce detectable products, indicating that genomic DNA had been eliminated from RNA samples. PCR using primers AAVRT-F1 (SEQ ID NO:62) and P349R9 (SEQ ID NO:63) produced two PCR products of similar fluorescent intensity derived from spliced transcripts after the STOP cassette has been excised from P439. One product resulted from splicing at the engineered beta-Actin splice donor and acceptor sites (SEQ ID NO:14 and SEQ ID NO:15 respectively; FIG. 8). The second product results from splicing between a donor site in the 5' REP gene (SEQ ID NO:64) and the downstream beta-Actin acceptor (FIG. 8). This splicing event is predicted to remove 64 bp of the REP coding sequence relative to wild-type AAV2, creating a frameshift and producing truncated REP proteins. This suggests that mutating this upstream splice donor site could increase the abundance of active REP proteins and make AAV production more efficient.

Updating the AAV Construct: P600 (SEQ ID NO:70)

Several changes were made to plasmid P439 (SEQ ID NO:12), resulting in construct P600 (SEQ ID NO:70). First, the splice donor site of the REP gene upstream of the STOP cassette was mutated. Briefly, the nucleotides GT of the splice donor site identified in the 5' REP sequence (SEQ ID NO:64) was mutated to AT (SEQ ID NO:65). This mutation is predicted to eliminate splicing at this site without changing the REP protein sequence.

To reduce the possibility that the REP/CAP gene could be packaged into AAV capsids following excision of the STOP cassette, a 2 kb random sequence (SEQ ID NO:66) was designed and inserted downstream of the attB sequence and upstream of the Actin splice acceptor to increase the size of the engineered intron. Potential splice sites were identified using NetGene 2 software (Cited above) and removed. This insertion increased the size of the REP/CAP gene from 4.3 kb to 6.4 kb, which is well above the 5.0 kb AAV packaging limit.

Based on the hypothesis that sequences adjacent to AAV ITRs may also be amplified during transgene rescue from the genome and might be mispackaged into AAV capsids (see, e.g., Schnodt and Buning, *Hum Gene Ther Methods.*, 2017; 28(3):101-108), two, random 2 kb non-coding spacer elements were design to flank the transgene to decrease the potential impact of mispackaged DNA. One element (SEQ ID NO:67) was inserted upstream of the left AAV ITR and the second (SEQ ID NO:68) replaced mouse anti-repressor element 40 (SEQ ID NO:25) downstream of the right AAV ITR.

In addition, the cap gene was an AAV9 variant (see, e.g., Hinderer et al., *Hum Gene Ther.* 2018; 29(3):285-298).

Finally, the coding sequence of the ITR-flanked transgene in P439 was replaced by SEQ ID NO:69 encoding an mCherry-IRES-SEAP (secreted alkaline phosphatase) protein.

Figure 9:
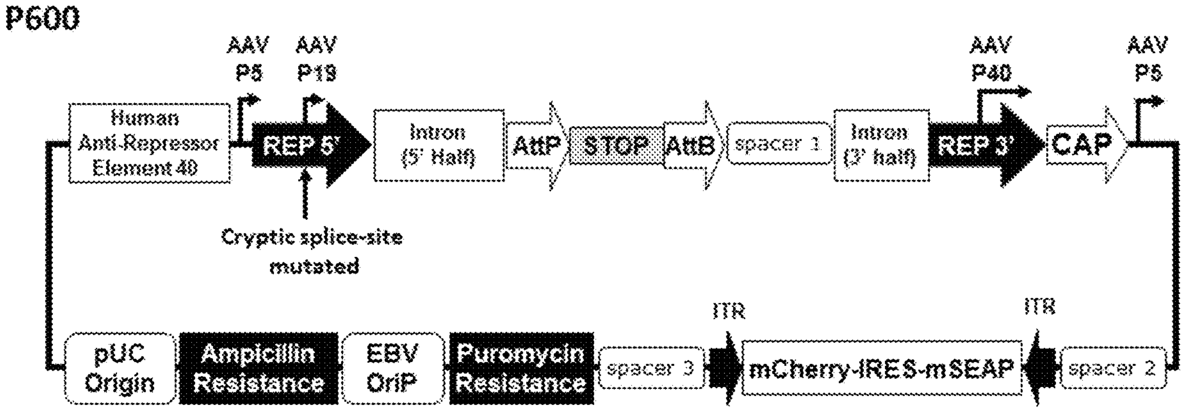
FIG. 9 illustrates a vector (plasmid P600) according to an embodiment of the application.

The complete sequence of the resulting construct P600 is disclosed in SEQ ID NO:70 and an illustration of the plasmid is shown in FIG. 9.

AAV Production from P600 in Stable Pools

Construct P600 was transfected into Peak-RAPID cells and a stable pool was generated through selection with 0.5 µg/ml puromycin essentially as described for P439 cells above. Cells were passed 1:10 for 6 weeks prior to assaying AAV production.

2.5E6 P600-PEAK-Rapid p6 cells were plated into three T25 flasks in 5 mls DMEM+10% FBS and incubated for three days at 37° C. The cells density on the day of infection was determined to be 6.6E6 viable cells in one of the flasks where cells were recovered with TrypLE and counted using Trypan blue exclusion. Media in the two remaining flasks were replaced with 11 mls DMEM+2% FBS containing 2.6E8 Ad5-CMV-SR21 virus particles. The flasks were incubated for 24 hours at 32° C. One ml of 1.25 mM 2-Aminopurine in DMEM+2% FBS was added to one flask. One ml of DMEM+2% FBS was added to the other flask, and both flasks were incubated at 32° C. for 7 additional days. Media was recovered from the flasks, centrifuged at 3,000 rpm for 5 minutes to pellet cells and debris. 2 µl of each sample supernatant was subjected to DNAse digestion and ddPCR quantitation using the mCherry assay as described above.

AAV production levels are shown in Table 6. The P600 stable pool is active in producing AAV upon infection with Ad5-CMV-SR21. AAV virus production was increased 2.5-fold in the presence of 2-aminopurine, a drug reported to block adenovirus-induced inhibition of CAP-dependent mRNA translation (see, e.g., Zhang and Schneider (1994) J. Virology 68: 2544-2555; and Huang and Schneider (1990) PNAS 87: 7115-7119). While it has been reported that 10 mM 2-AP treatment 1-2 hours post infection blocked cytopathic effect of adenovirus infection and was nontoxic for at least three days (see, e.g., Zhang and Schneider (1994) J. Virology 68: 2544-2555; and Huang and Schneider (1990) PNAS 87: 7115-7119), we found concentrations above 1.25 mM and addition earlier than 24 hours to be inhibitory to AAV production in our AAV producer cell system. These data suggest that inhibiting late adenoviral gene programs, especially the shutdown of cap-dependent mRNA translation, is a useful strategy for increasing AAV production in producer cell lines.

TABLE 6

| Sample | Media | AAV GC/Cell |
|---|---|---|
| 1 | DMEM + 2% FBS | 23,826 ± 2990 |
| 2 | DMEM + 2% FBS + 1.25 mM2-AP | 59,356 ± 11,026 |

Manufacturing of recombinant adeno-associated virus (AAV) in human cells requires expression of AAV replication (REP) and capsid (CAP) genes, adenovirus genes and an AAV-packagable transgene consisting of an expression cassette flanked by AAV inverted terminal repeats (ITRs). All three components can be delivered to cells on separate plasmids for AAV production, but existing transfection methods are difficult to scale to large-scale cultures. Incorporating some of these elements into the host cell line could make AAV production more efficient, however, some of the AAV and adenovirus genes are cytostatic or cytotoxic, limiting this approach. The present invention describes a way to reversibly-inactivate the AAV REP genes such that AAV REP, CAP, and a packagable transgene can be integrated into suitable host cells and expanded. Infection of these cells by a replication-deficient recombinant adenovirus (e.g., ΔE1/ΔE3) expressing a recombinase reactivates the REP genes and induces AAV replication and packaging.

What is claimed is:

1. A non-naturally occurring nucleic acid molecule comprising a nucleotide sequence encoding a serine recombinase having at least 99% identity to SEQ ID NO:3, wherein the non-naturally occurring nucleic acid molecule is codon optimized for expression in a mammalian cell.

2. A cultured mammalian cell comprising:
(a) the non-naturally occurring nucleic acid molecule of claim 1; or
(b) a vector comprising the non-naturally occurring nucleic acid molecule of claim 1.

3. The cell of claim 2, wherein the cell is a 911 cell, pTG6559 cell, GH329 cell, N52.E6 cell, HeLa-E1 cell, UR cell, VLI-293 cell, HEK293 cell, or a PER.C6 cell.

4. The cell of claim 2, wherein the cell further comprises adenovirus E1A and E1B genes.

5. The cell of claim 2, wherein the cell further comprises:
(a) a nucleic acid sequence comprising an attP site, wherein the attP site comprises a nucleotide sequence that is at least 98% identical to the nucleotide sequence of SEQ ID NO: 7; and/or
(b) a nucleic acid sequence comprising an attB site, wherein the attB site comprises a nucleotide sequence that is at least 98% identical to the nucleotide sequence of SEQ ID NO: 8 or 9.

6. The cell of claim 2, wherein the cell further comprises:
(a) a nucleic acid sequence comprising an attP site, wherein the attP site comprises the nucleotide sequence of SEQ ID NO: 7; and/or
(b) a nucleic acid sequence comprising an attB site, wherein the attB site comprises a nucleotide sequence that is at least 98% identical to the nucleotide sequence of SEQ ID NO: 8 or 9.

7. The cell of claim 2, wherein the cell further comprises:
(a) a nucleic acid sequence comprising an attP site, wherein the attP site comprises a nucleotide sequence that is at least 98% identical to the nucleotide sequence of SEQ ID NO: 7; and/or
(b) a nucleic acid sequence comprising an attB site, wherein the attB site comprises the nucleotide sequence of SEQ ID NO: 8 or 9.

8. The cell of claim 2, wherein the cell further comprises:
(a) a nucleic acid sequence comprising an attP site, wherein the attP site comprises the nucleotide sequence of SEQ ID NO: 7; and
(b) a nucleic acid sequence comprising an attB site, wherein the attB site comprises the nucleotide sequence of SEQ ID NO: 8 or 9.

9. A non-naturally occurring nucleic acid molecule comprising the nucleotide sequence of SEQ ID NO:3 and a heterologous promoter operably linked to the nucleotide sequence.

10. A vector comprising a non-naturally occurring nucleic acid molecule comprising a nucleotide sequence encoding a serine recombinase having at least 99% identity to SEQ ID NO:3.

11. The vector of claim 10, further comprising a promoter operably linked to said nucleic acid molecule.

12. The vector of claim 11, wherein the promoter is a cytomegalovirus (CMV) promoter, a simian virus 40 (SV40) promoter, a mouse mammary tumor virus (MMTV) promoter, a human immunodeficiency virus (HIV) promoter, a Moloney virus promoter, an avian leukosis virus (ALV) promoter, an Epstein Barr virus (EBV) promoter, or a Rous sarcoma virus (RSV) promoter.

13. The vector of claim 11, wherein the promoter is a tissue specific promoter.

14. The vector of claim 11, further comprising a polyadenylation signal operably linked to the nucleic acid molecule.

15. The vector of claim 14, wherein the polyadenylation signal is a simian virus 40 (SV40) polyadenylation signal, bovine growth hormone (bGH) polyadenylation signal, human growth hormone (hGH) polyadenylation signal, or human b-globin polyadenylation signal.

16. The vector of claim 11, wherein the vector is a DNA plasmid or a viral vector.

17. The vector of claim 16, wherein the viral vector is an adenoviral vector, adeno-associated virus vector, a pox virus vector, an enteric virus vector, a Venezuelan Equine Encephalitis virus vector, a Semliki Forest Virus vector, Tobacco Mosaic Virus vector, or lentiviral vector.

18. The vector of claim 16, wherein the viral vector is a recombinant adenoviral vector.

19. A vector comprising a non-naturally occurring nucleic acid molecule comprising the nucleotide sequence of SEQ ID NO:3.

20. A cultured mammalian cell comprising:
(a) a non-naturally occurring nucleic acid molecule comprising the nucleotide sequence of SEQ ID NO:3; or
(b) a vector comprising the non-naturally occurring nucleic acid molecule comprising the nucleotide sequence of SEQ ID NO:3.

* * * * *

SEQUENCE LISTING

```
<160> NUMBER OF SEQ ID NOS: 73

<210> SEQ ID NO 1
<211> LENGTH: 545
<212> TYPE: PRT
<213> ORGANISM: Artificial Sequence
<220> FEATURE:
<223> OTHER INFORMATION: SPBetac2 Integrase (NP_046553.1) Protein
      Sequence

<400> SEQUENCE: 1
```

-continued

```
Met Glu Leu Lys Asn Ile Val Asn Ser Tyr Asn Ile Thr Asn Ile Leu
1               5                   10                  15

Gly Tyr Leu Arg Arg Ser Arg Gln Asp Met Glu Arg Glu Lys Arg Thr
            20                  25                  30

Gly Glu Asp Thr Leu Thr Glu Gln Lys Glu Leu Met Asn Lys Ile Leu
        35                  40                  45

Thr Ala Ile Glu Ile Pro Tyr Glu Leu Lys Met Glu Ile Gly Ser Gly
    50                  55                  60

Glu Ser Ile Asp Gly Arg Pro Val Phe Lys Glu Cys Leu Lys Asp Leu
65                  70                  75                  80

Glu Glu Gly Lys Tyr Gln Ala Ile Ala Val Lys Glu Ile Thr Arg Leu
                85                  90                  95

Ser Arg Gly Ser Tyr Ser Asp Ala Gly Gln Ile Val Asn Leu Leu Gln
            100                 105                 110

Ser Lys Arg Leu Ile Ile Ile Thr Pro Tyr Lys Val Tyr Asp Pro Arg
        115                 120                 125

Asn Pro Val Asp Met Arg Gln Ile Arg Phe Glu Leu Phe Met Ala Arg
    130                 135                 140

Glu Glu Phe Glu Met Thr Arg Glu Arg Met Thr Gly Ala Lys Tyr Thr
145                 150                 155                 160

Tyr Ala Ala Gln Gly Lys Trp Ile Ser Gly Leu Ala Pro Tyr Gly Tyr
                165                 170                 175

Gln Leu Asn Lys Lys Thr Ser Lys Leu Asp Pro Val Glu Asp Glu Ala
            180                 185                 190

Lys Val Val Gln Leu Ile Phe Asn Ile Phe Leu Asn Gly Leu Asn Gly
        195                 200                 205

Lys Asp Tyr Ser Tyr Thr Ala Ile Ala Ser His Leu Thr Asn Leu Gln
    210                 215                 220

Ile Pro Thr Pro Ser Gly Lys Lys Arg Trp Asn Gln Tyr Thr Ile Lys
225                 230                 235                 240

Ala Ile Leu Gln Asn Glu Val Tyr Ile Gly Thr Val Lys Tyr Lys Val
                245                 250                 255

Arg Glu Lys Thr Lys Asp Gly Lys Arg Thr Ile Arg Pro Glu Lys Glu
            260                 265                 270

Gln Ile Val Val Gln Asp Ala His Ala Pro Ile Ile Asp Lys Glu Gln
        275                 280                 285

Phe Gln Gln Ser Gln Val Lys Ile Ala Asn Lys Val Pro Leu Leu Pro
    290                 295                 300

Asn Lys Asp Glu Phe Glu Leu Ser Glu Leu Ala Gly Val Cys Thr Cys
305                 310                 315                 320

Ser Lys Cys Gly Glu Pro Leu Ser Lys Tyr Glu Ser Lys Arg Ile Arg
                325                 330                 335

Lys Asn Lys Asp Gly Thr Glu Ser Val Tyr His Val Lys Ser Leu Thr
            340                 345                 350

Cys Lys Lys Asn Lys Cys Thr Tyr Val Arg Tyr Asn Asp Val Glu Asn
        355                 360                 365

Ala Ile Leu Asp Tyr Leu Ser Ser Leu Asn Asp Leu Asn Asp Ser Thr
    370                 375                 380

Leu Thr Lys His Ile Asn Ser Met Leu Ser Lys Tyr Glu Asp Asp Asn
385                 390                 395                 400

Ser Asn Met Lys Thr Lys Lys Gln Met Ser Glu His Leu Ser Gln Lys
                405                 410                 415
```

```
Glu Lys Glu Leu Lys Asn Lys Glu Asn Phe Ile Phe Asp Lys Tyr Glu
            420                 425                 430

Ser Gly Ile Tyr Ser Asp Glu Leu Phe Leu Lys Arg Lys Ala Ala Leu
        435                 440                 445

Asp Glu Glu Phe Lys Glu Leu Gln Asn Ala Lys Asn Glu Leu Asn Gly
    450                 455                 460

Leu Gln Asp Thr Gln Ser Glu Ile Asp Ser Asn Thr Val Arg Asn Asn
465                 470                 475                 480

Ile Asn Lys Ile Ile Asp Gln Tyr His Ile Glu Ser Ser Ser Glu Lys
                485                 490                 495

Lys Asn Glu Leu Leu Arg Met Val Leu Lys Asp Val Ile Val Asn Met
            500                 505                 510

Thr Gln Lys Arg Lys Gly Pro Ile Pro Ala Gln Phe Glu Ile Thr Pro
        515                 520                 525

Ile Leu Arg Phe Asn Phe Ile Phe Asp Leu Thr Ala Thr Asn Ser Phe
    530                 535                 540

His
545


<210> SEQ ID NO 2
<211> LENGTH: 535
<212> TYPE: PRT
<213> ORGANISM: Artificial sequence
<220> FEATURE:
<223> OTHER INFORMATION: SR21 Recombinase (WP_029708089.1) Protein
      Sequence

<400> SEQUENCE: 2

Met Glu Leu Lys His Ile Val Asn Ser Tyr Asn Val Thr Lys Ile Ile
1               5                   10                  15

Gly Tyr Leu Arg Arg Ser Arg Gln Asp Val Glu Arg Glu Lys Arg Thr
            20                  25                  30

Gly Glu Asp Thr Leu Thr Glu Gln Lys Glu Leu Met Asn Lys Ile Leu
        35                  40                  45

Thr Gly Ile Glu Ile Pro Tyr Glu Thr Arg Thr Glu Ile Gly Ser Gly
    50                  55                  60

Glu Ser Ile Glu Gly Arg Pro Val Phe Lys Ser Cys Leu Ala Asp Leu
65                  70                  75                  80

Arg Ser Gly Lys Phe Gln Ala Ile Ala Val Lys Glu Ile Thr Arg Leu
                85                  90                  95

Ser Arg Gly Ser Tyr Ser Asp Ala Gly Glu Ile Val Asn Leu Leu Asn
            100                 105                 110

Glu Lys Arg Ile Ile Ile Ile Thr Pro Tyr Lys Ile Tyr Asp Pro Arg
        115                 120                 125

Asn Pro Val Asp Ala Arg Gln Ile Arg Phe Glu Leu Phe Met Ala Arg
    130                 135                 140

Glu Glu Phe Glu Met Thr Arg Glu Arg Met Asn Gly Ala Lys Phe Thr
145                 150                 155                 160

Tyr Ala Ala Gln Gly Lys Trp Ile Ser Gly Leu Ala Pro Phe Gly Tyr
                165                 170                 175

Lys Leu Asn Lys Arg Thr Ser Arg Leu Glu Pro Ser Asp Glu Asp Lys
            180                 185                 190

Val Val Val Lys Leu Ile Phe Asp Ile Phe Leu Asn Gly Leu Asp Gly
        195                 200                 205

Lys Asp Leu Ser Tyr Thr Ala Ile Ala Thr His Leu Ser Lys Leu Gln
    210                 215                 220
```

-continued

```
Phe Thr Thr Pro Arg Gly Gly Lys Arg Trp Ser Lys Asp Thr Val Arg
225                 230                 235                 240

Lys Ile Leu Gln Asn Glu Ala Tyr Met Gly Arg Val Arg Tyr Lys Ala
                245                 250                 255

Arg Glu Thr Thr Lys Asp Gly Lys Lys Val Phe Arg Pro Glu Ser Glu
            260                 265                 270

His Ile Val Val Asp Asp Ala His Glu Pro Ile Ile Asn Lys Glu Asp
        275                 280                 285

Phe Glu Ala Val Gln Glu Lys Ile Lys Asn Lys Val Pro Leu Leu Pro
    290                 295                 300

Val Val Thr Ser Tyr Glu Pro Asn Glu Leu Ala Gly Ile Cys Val Cys
305                 310                 315                 320

Ser Val Cys Gly Lys Ser Leu Gln Lys Phe Glu Ser Glu Tyr Asn Arg
                325                 330                 335

Lys Asn Lys Asp Gly Thr Ser Ser Tyr Phe His Val Lys Leu Leu Ile
            340                 345                 350

Cys Lys Ile Asn Lys Cys Thr Ser Val Arg Tyr Glu Tyr Val Glu Glu
        355                 360                 365

Ala Ile Leu Glu Tyr Leu Glu Gln Leu Ile Ala Leu Glu Asn Asn Lys
    370                 375                 380

Leu Lys Ala Ile Ile Glu Lys Ser Met Glu Ala Ala Glu Thr Asn Asn
385                 390                 395                 400

Ser Glu Lys Thr Ser Glu Gln Met Leu Val Gln Ala Asn Gln Lys Gln
                405                 410                 415

Lys Glu Leu Glu Asn Lys Leu Thr Phe Ile Phe Glu Lys Phe Glu Ser
            420                 425                 430

Gly Ile Tyr Thr Asp Glu Met Phe Leu Gln Arg Lys Ala Ala Ile Glu
        435                 440                 445

Lys Glu Val Ala Asp Ile Lys Lys Leu Lys Gln Glu Leu Ser Met Thr
    450                 455                 460

Phe Glu Val Lys Glu Lys Asp Val Asn Glu Phe Arg Val Asn Ile Ser
465                 470                 475                 480

Asp Val Val Lys Phe Tyr Lys Glu Ser Lys Ser Arg Gly Leu Lys Asn
                485                 490                 495

Glu Lys Leu Arg Ser Ile Phe Asp Phe Ile Val Leu Glu Met Thr Glu
            500                 505                 510

Lys Arg Arg Gly Pro Ile Pro Ala Lys Phe Asn Ile Tyr Pro Val Leu
        515                 520                 525

Arg Ile Pro Ser Val Val Asn
    530                 535
```

<210> SEQ ID NO 3
<211> LENGTH: 1608
<212> TYPE: DNA
<213> ORGANISM: Artificial sequence
<220> FEATURE:
<223> OTHER INFORMATION: SR21 Recombinase DNA Sequence

<400> SEQUENCE: 3

```
ttggaattaa aacacattgt caattcctat aatgtgacta aaattattgg ctatttgaga     60

cgttctagac aagatgttga aagagagaag cgtactggtg aagatacttt gacagaacaa    120

aaagaactta tgaataaaat attgactggg attgaaatac cgtacgaaac aagaactgag    180

atcggttctg gtgaaagcat tgaaggaaga ccagtgttta aaagttgctt agctgatctg    240
```

-continued

```
aggtctggaa aatttcaagc aattgctgta aaagaaataa ctcgtcttag tcgtggtagt    300

tacagtgatg ctggtgaaat cgtcaatctt ctaaatgaaa aaaggattat cataattaca    360

ccatataaaa tatatgatcc aagaaatcct gttgatgctc gtcaaattag atttgagcta    420

tttatggcta gagaagaatt tgaaatgaca agagaaagaa tgaatggtgc caagtttact    480

tatgctgcac aaggaaaatg gatttctggt ttagcaccat ttggctataa attaaataag    540

cgtacatctc gcctcgaacc atcggatgaa gacaaagttg tggtaaagtt gatatttgac    600

attttcttaa atggccttga tggtaaagat ttaagttata cagctattgc aactcatctt    660

tctaaacttc aattcactac cccaagggga ggaaaaagat ggagtaagga cactgttaga    720

aaaattcttc aaaatgaagc ctatatggga agggttaggt ataaagcaag agaaaccaca    780

aaagatggaa aaaaagtctt ccgacctgaa agtgaacata ttgttgtaga tgatgcccac    840

gaaccaataa taaataaaga ggactttgaa gctgttcaag aaaagattaa aaataaagtg    900

cctctgcttc cagtcgtaac atcttatgaa cctaatgaat tagcgggaat atgtgtatgc    960

tctgtctgtg gaaaatcact tcaaaaattt gaatccgaat acaataggaa aaacaaagat   1020

gggacttcca gctattttca cgtgaagtta ttgatttgca aaatcaacaa gtgcacatca   1080

gtgagatatg agtatgttga agaagcaatt ttggagtatc ttgagcagtt gattgcttta   1140

gaaaataata aactaaaggc tataattgaa aaatctatgg aagcagcaga aactaacaat   1200

tcagaaaaga caagtgagca aatgctagta caagcaaacc aaaaacagaa agagctcgaa   1260

aacaaattga catttatttt tgaaaaattt gaatctggaa tttatacaga tgaaatgttt   1320

ttgcaaagga aagcagctat tgaaaaagaa gtagctgaca ttaaaaaatt gaaacaagaa   1380

cttagcatga catttgaagt taaagagaaa gatgttaatg aatttagggt taacatatca   1440

gatgtagtta aattttataa agaatctaaa agtagaggat taaaaaatga aaagttgaga   1500

tccatttttg actttatagt attagaaatg acagagaaaa gacgaggccc catccctgct   1560

aagttcaata tttatccggt tttgcgaatt ccgagtgtag ttaattaa                1608
```

<210> SEQ ID NO 4
<211> LENGTH: 188
<212> TYPE: DNA
<213> ORGANISM: Artificial sequence
<220> FEATURE:
<223> OTHER INFORMATION: Bacillus safensis Fairview strain Pre-insertion locus (gi|640668059:c464939-464752)

<400> SEQUENCE: 4

```
agataatccg ttcgaagctg ttcaaacgaa tatcatcggc gggcagcacg tcattgaagc     60

cgcaattgaa catgaagtga gtcatgtcgt caacatctcc actgacaaag cggtttctcc    120

aacgaatgcc atgggtgcaa caaaattgat ttcagaaaaa ctatttttcc aagcaaacga    180

aagtattc                                                             188
```

<210> SEQ ID NO 5
<211> LENGTH: 120
<212> TYPE: DNA
<213> ORGANISM: Artificial sequence
<220> FEATURE:
<223> OTHER INFORMATION: Right Prophage-Host DNA Junction, Bacillus safensis strain CCMA-560

<400> SEQUENCE: 5

```
tttgcgaatt ccgagtgtag ttaattaagt atcatgataa actgacaaag cggtttctcc     60

aacgaatgcc atgggtgcaa caaaattgat ttcagaaaaa ctatttttcc aagcaaacga    120
```

-continued

<210> SEQ ID NO 6
<211> LENGTH: 158
<212> TYPE: DNA
<213> ORGANISM: Artificial sequence
<220> FEATURE:
<223> OTHER INFORMATION: Left Prophage-Host DNA Junction, Bacillus safensis strain CCMA-560

<400> SEQUENCE: 6
tatcatcggc gggcagcacg tcattgaagc cgctctcgaa catgaagtga gtcatgtcgt 60
caacatttca actgacaaag cggtatatca agatacttaa tacatgataa caaaaaaaga 120
agcctacata ttggcttctt ttataattat atttgcta 158

<210> SEQ ID NO 7
<211> LENGTH: 50
<212> TYPE: DNA
<213> ORGANISM: Artificial sequence
<220> FEATURE:
<223> OTHER INFORMATION: SR21 Recombinase AttP reconstructed from Bacillus safensis strain CCMA-560 (artificial sequence)

<400> SEQUENCE: 7
aattaagtat catgataaac tgacaaagcg gtatatcaag atacttaata 50

<210> SEQ ID NO 8
<211> LENGTH: 40
<212> TYPE: DNA
<213> ORGANISM: Artificial sequence
<220> FEATURE:
<223> OTHER INFORMATION: SR21 Recombinase AttB reconstructed from Bacillus safensis strain CCMA-560

<400> SEQUENCE: 8
cgtcaacatt tcaactgaca aagcggtttc tccaacgaat 40

<210> SEQ ID NO 9
<211> LENGTH: 40
<212> TYPE: DNA
<213> ORGANISM: Artificial sequence
<220> FEATURE:
<223> OTHER INFORMATION: SR21 Recombinase AttB reconstructed from Bacillus safensis strain Fairview

<400> SEQUENCE: 9
cgtcaacatc tccactgaca aagcggtttc tccaacgaat 40

<210> SEQ ID NO 10
<211> LENGTH: 4532
<212> TYPE: DNA
<213> ORGANISM: Artificial sequence
<220> FEATURE:
<223> OTHER INFORMATION: P175- SR21 Mammalian expression vector

<400> SEQUENCE: 10
taactataac ggtcctaagg tagcgaagct cttcagatgg acagtcagac tgaagagcct 60
ctcttaaggt agctcgagga gcttggccca ttgcatacgt tgtatccata tcataatatg 120
tacatttata ttggctcatg tccaacatta ccgccatgtt gacattgatt attgactagt 180
tattaatagt aatcaattac ggggtcatta gttcatagcc catatatgga gttccgcgtt 240
acataactta cggtaaatgg cccgcctggc tgaccgccca acgacccccg cccattgacg 300
tcaataatga cgtatgttcc catagtaacg ccaataggga ctttccattg acgtcaatgg 360

-continued

```
gtggagtatt tacggtaaac tgcccacttg gcagtacatc aagtgtatca tatgccaagt    420
acgcccccta ttgacgtcaa tgacggtaaa tggcccgcct ggcattatgc ccagtacatg    480
accttatggg actttcctac ttggcagtac atctacgtat tagtcatcgc tattaccatg    540
gtgatgcggt tttggcagta catcaatggg cgtggatagc ggtttgactc acggggattt    600
ccaagtctcc accccattga cgtcaatggg agtttgtttt ggcaccaaaa tcaacgggac    660
tttccaaaat gtcgtaacaa ctccgcccca ttgacgcaaa tgggcggtag gcgtgtacgg    720
tgggaggtct atataagcag agctcgttta gtgaaccgtc ggcgcgccgc caccatggaa    780
ttaaaacaca ttgtcaattc ctataatgtg actaaaatta ttggctattt gagacgttcc    840
agacaagatg ttgaaagaga gaagcgtact ggtgaagata ctttgacaga acaaaaagaa    900
cttatgaata aaatattgac tggattgaa ataccgtacg aaacaagaac tgagatcggt    960
tctggtgaaa gcattgaagg aagaccagtg tttaaaagtt gcttagctga tctgaggtct   1020
ggaaaatttc aagcaattgc tgtaaaagaa ataactcgtc ttagtcgtgg tagttacagt   1080
gatgctggtg aaatcgtcaa tcttctaaat gaaaaaagga ttatcataat tacaccatat   1140
aaaatatatg atccaagaaa tcctgttgat gctcgtcaaa ttagatttga gctatttatg   1200
gctagagaag aatttgaaat gacaagagaa agaatgaatg gtgccaagtt tacttatgct   1260
gcacaaggaa aatggatttc tggtttagca ccatttggct ataaattaaa taagcgtaca   1320
tctcgcctcg aaccatcgga tgaagacaaa gttgtggtaa agttgatatt tgacattttc   1380
ttaaatggcc ttgatggtaa agatttaagt tatacagcta ttgcaactca tctttctaaa   1440
cttcaattca ctaccccaag ggaggaaaa agatggagta aggacactgt tagaaaaatt   1500
cttcaaaatg aagcctatat gggaagggtt aggtataaag caagagaaac cacaaaagat   1560
ggaaaaaaag tcttccgacc tgaaagtgaa catattgttg tagatgatgc ccacgaacca   1620
ataataaata aagaggactt tgaagctgtt caagaaaaga ttaaaaataa agtgcctctg   1680
cttccagtcg taacatctta tgaacctaat gaattagcgg gaatatgtgt atgctctgtc   1740
tgtggaaaat cacttcaaaa atttgaatcc gaatacaata ggaaaaacaa agatgggact   1800
tccagctatt ttcacgtgaa gttattgatt tgcaaaatca acaagtgcac atcagtgaga   1860
tatgagtatg ttgaagaagc aattttggag tatcttgagc agttgattgc tttagaaaat   1920
aataaactaa aggctataat tgaaaaatct atggaagcag cagaaactaa caattcagaa   1980
aagacaagtg agcaaatgct agtacaagca aaccaaaaac agaaagaact cgaaaacaaa   2040
ttgacattta tttttgaaaa atttgaatct ggaatttata cagatgaaat gtttttgcaa   2100
aggaaagcag ctattgaaaa agaagtagct gacattaaaa aattgaaaca agaacttagc   2160
atgacatttg aagttaaaga gaaagatgtt aatgaattta gggttaacat atcagatgta   2220
gttaaatttt ataaagaatc taaaagtaga ggattaaaaa atgaaaagtt gagatccatt   2280
tttgacttta tagtattaga aatgacagag aaaagacgag gccccatccc tgctaagttc   2340
aatatttatc cggttttgcg aatcccgagt gtagttaatt aatctagaga tacattgatg   2400
agtttggaca aaccacaact agaatgcagt gaaaaaaatg ctttatttgt gaaatttgtg   2460
atgctattgc tttatttgta accattataa gctgcaataa acaagttaac aacaacaatt   2520
gcattcattt tatgtttcag gttcaggggg aggtgtggga ggttttttaa agcaagtaaa   2580
acctctacaa atgtggtatg gctgattatg atcgcggccg caataaagat cccgggtagg   2640
gataacaggg taatgctctt cagatggaca gtcagactga agagctggca aacagctatt   2700
atgggtatta tgggtgacgt caggtggcac ttttcgggga aatgtgcgcg gaacccctat   2760
```

ttgtttattt ttctaaatac attcaaatat gtatccgctc atgagacaat aaccctgata 2820
aatgcttcaa taatattgaa aaaggaagag tatgagtatt caacatttcc gtgtcgccct 2880
tattcccttt tttgcggcat tttgccttcc tgtttttgct cacccagaaa cgctggtgaa 2940
agtaaaagat gctgaagatc agttgggtgc acgagtgggt tacatcgaac tggatctcaa 3000
cagcggtaag atccttgaga gttttcgccc cgaagaacgt tttccaatga tgagcacttt 3060
taaagttctg ctatgtggcg cggtattatc ccgtattgac gccgggcaag agcaactcgg 3120
tcgccgcata cactattctc agaatgactt ggttgagtac tcaccagtca cagaaaagca 3180
tcttacggat ggcatgacag taagagaatt atgcagtgct gccataacca tgagtgataa 3240
cactgcggcc aacttacttc tgacaacgat cggaggaccg aaggagctaa ccgctttttt 3300
gcacaacatg ggggatcatg taactcgcct tgatcgttgg gaaccggagc tgaatgaagc 3360
cataccaaac gacgagcgtg acaccacgat gcctgtagca atggcaacaa cgttgcgcaa 3420
actattaact ggcgaactac ttactctagc ttcccggcaa caattaatag actggatgga 3480
ggcggataaa gttgcaggac cacttctgcg ctcggccctt ccggctggct ggtttattgc 3540
tgataaatct ggagccggtg agcgtgggtc tcgcggtatc attgcagcac tggggccaga 3600
tggtaagccc tcccgtatcg tagttatcta cacgacgggg agtcaggcaa ctatggatga 3660
acgaaataga cagatcgctg agataggtgc ctcactgatt aagcattggt aactgtcaga 3720
ccaagtttac tcatatatac tttagattga tttaaaactt catttttaat ttaaaaggat 3780
ctaggtgaag atcctttttg ataatctcat gaccaaaatc ccttaacgtg agttttcgtt 3840
ccactgagcg tcagaccccg tagaaaagat caaaggatct tcttgagatc cttttttict 3900 gcgcgtaatc tgctgcttgc aaacaaaaaa accaccgcta ccagcggtgg tttgtttgcc 3960
ggatcaagag ctaccaactc tttttccgaa ggtaactggc ttcagcagag cgcagatacc 4020
aaatactgtt cttctagtgt agccgtagtt aggccaccac ttcaagaact ctgtagcacc 4080
gcctacatac ctcgctctgc taatcctgtt accagtggct gctgccagtg gcgataagtc 4140
gtgtcttacc gggttggact caagacgata gttaccggat aaggcgcagc ggtcgggctg 4200
aacggggggt tcgtgcacac agcccagctt ggagcgaacg acctacaccg aactgagata 4260
cctacagcgt gagctatgag aaagcgccac gcttcccgaa gggagaaagg cggacaggta 4320
tccggtaagc ggcagggtcg gaacaggaga gcgcacgagg gagcttccag ggggaaacgc 4380
ctggtatctt tatagtcctg tcgggtttcg ccacctctga cttgagcgtc gatttttgtg 4440
atgctcgtca ggggggcgga gcctatggaa aaacgccagc aacgcggcct ttttacggtt 4500
cctggccttt tgctggcctt ttgctcacat gt 4532

<210> SEQ ID NO 11
<211> LENGTH: 9555
<212> TYPE: DNA
<213> ORGANISM: Artificial sequence
<220> FEATURE:
<223> OTHER INFORMATION: P41- SR21 recombinase reporter plasmid

<400> SEQUENCE: 11
taactataac ggtcctaagg tagcgaagct cttcagatgg acagtcagac tgaagagcct 60
ctcttaaggt agctcgagga gcttggccca ttgcatacgt tgtatccata tcataatatg 120
tacatttata ttggctcatg tccaacatta ccgccatgtt gacattgatt attgactagt 180
tattaatagt aatcaattac ggggtcatta gttcatagcc catatatgga gttccgcgtt 240

-continued

```
acataactta cggtaaatgg cccgcctggc tgaccgccca acgacccccg cccattgacg    300
tcaataatga cgtatgttcc catagtaacg ccaataggga ctttccattg acgtcaatgg    360
gtggagtatt tacggtaaac tgcccacttg gcagtacatc aagtgtatca tatgccaagt    420
acgcccccta ttgacgtcaa tgacggtaaa tggcccgcct ggcattatgc ccagtacatg    480
accttatggg actttcctac ttggcagtac atctacgtat tagtcatcgc tattaccatg    540
gtgatgcggt tttggcagta catcaatggg cgtggatagc ggtttgactc acggggattt    600
ccaagtctcc accccattga cgtcaatggg agtttgtttt ggcaccaaaa tcaacgggac    660
tttccaaaat gtcgtaacaa ctccgcccca ttgacgcaaa tgggcggtag gcgtgtacgg    720
tgggaggtct atataagcag agctcgttta gtgaaccgtc ggcgcgcccg tcaacatctc    780
cactgacaaa gcggtttctc caacgaatgg atccttacac ggcgatcttg ccgcccttct    840
tggccttaat gagaatctcg cggatcttgc gggcgtccaa cttgccggtc agtcctttag    900
gcacctcgtc cacgaacaca acaccaccgc gcagcttctt ggcggttgta acctggctgg    960
ccacatagtc cacgatctcc ttctcggtca tggttttacc gtgttccagc acgacgactg   1020
cggcgggcag ctcgccggca tcgtcgtcgg gcaggccggc gaccccggcg tcgaagatgt   1080
tggggtgttg cagcaggatg ctctccagtt cggctggggc tacctggtag cccttgtatt   1140
tgatcaggct cttcagccgg tccacgatga agaagtgctc gtcctcgtcc cagtaggcga   1200
tgtcgccgct gtgcagccag ccgtccttgt cgatgagagc gtttgtagcc tcggggttgt   1260
taacgtagcc gctcatgatc atggggccac ggacgcacag ctcgccgcgc tggttcacac   1320
ccagtgtctt accggtgtcc aagtccacca ccttagcctc gaagaagggc accaccttgc   1380
ctactgcgcc aggcttgtcg tccccttcgg gggtgatcag aatggcgctg gttgtttctg   1440
tcaggccgta gccctggcgg atgcctggta ggtggaagcg tttggccacg gcctcaccta   1500
cctccttgct gagcggcgcc ccgccgctgg cgatctcgtg caagttgctt aggtcgtact   1560
tgtcgatgag agtgctctta gcgaagaagc taaatagtgt gggcaccagc agggcagatt   1620
gaatcttata gtcttgcaag ctgcgcaaga atagctcctc ctcgaagcgg tacatgagca   1680
cgacccgaaa gccgcagatc aagtagccca gcgtggtgaa catgccgaag ccgtggtgaa   1740
atggcaccac gctgaggata gcggtgtcgg ggatgatctg gttgccgaag atggggtcgc   1800
gggcatgact gaatcggaca caagcggtgc ggtgcggtag ggctacgccc ttgggcaatc   1860
cggtactgcc actactgttc atgatcaggg cgatggtttt gtcccggtcg aagctctcgg   1920
gcacgaagtc gtactcgttg aagccgggtg gcaaatggga agtcacgaag gtgtacatgc   1980
tttggaagcc ctggtagtcg gtcttgctat ccatgatgat gatcttttgt atgatcggta   2040
gcttcttttg cacgttgagg atcttttgca gccctttctt gctcacgaat acgacggtgg   2100
gctggctgat gcccatgctg ttcagcagct cgcgctcgtt gtagatgtcg ttagctgggg   2160
ccacagccac accgatgaac agggcaccca acacgggcat gaagaactgc aagctattct   2220
cgctgcacac cacgatccga tggtttgtat tcagcccata gcgcttcata gcttctgcca   2280
gccgaacgct catctcgaag tactcggcgt aggtaatgtc cacctcgata tgtgcgtcgg   2340
taaaggcgat ggtgccgggc accagggcgt agcgcttcat ggctttgtgc agctgctcgc   2400
cggcggtccc gtcttcgagt gggtagaatg gcgctggacc cttcttaatg tttttggcat   2460
cttccatagg tccagggttg gactccacgt ctcccgccaa cttgagaagg tcaaaattca   2520
aagtctgttt cactccgctt cccttgtaca gctcgtccat gccgccggtg gagtggcggc   2580
cctcggcgcg ttcgtactgt tccacgatgg tgtagtcctc gttgtgggag gtgatgtcca   2640
```

-continued

```
acttgatgtt gacgttgtag gcgccgggca gctgcacggg cttcttggcc ttgtaggtgg   2700
tcttgacctc agcgtcgtag tggccgccgt ccttcagctt cagcctctgc ttgatctcgc   2760
ccttcagggc gccgtcctcg gggtacatcc gctcggagga ggcctcccag cccatggtct   2820
tcttctgcat tacggggccg tcggagggga agttggtgcc gcgcagcttc accttgtaga   2880
tgaactcgcc gtcctgcagg gaggagtcct gggtcacggt caccacgccg ccgtcctcga   2940
agttcatcac gcgctcccac ttgaagccct cggggaagga cagcttcaag tagtcgggga   3000
tgtcggcggg gtgcttcacg taggccttgg agccgtacat gaactgaggg gacaggatgt   3060
cccaggcgaa gggcaggggg ccacccttgg tcaccttcag cttggcggtc tgggtgccct   3120
cgtaggggcg gccctcgccc tcgccctcga tctcgaactc gtggccgttc acggagccct   3180
ccatgtgcac cttgaagcgc atgaactcct tgatgatggc catgttatcc tcctcgccct   3240
tgctcaccat ggtggcgtcg actattaagt atcttgatat accgctttgt cagtttatca   3300
tgatacttaa tttctagaga tacattgatg agtttggaca aaccacaact agaatgcagt   3360
gaaaaaaatg ctttatttgt gaaatttgtg atgctattgc tttatttgta accattataa   3420
gctgcaataa acaagttaac aacaacaatt gcattcattt tatgtttcag gttcaggggg   3480
aggtgtggga ggttttttaa agcaagtaaa acctctacaa atgtggtatg gctgattatg   3540
atcgcggccg ccgtgaggct ccggtgcccg tcagtgggca gagcgcacat cgcccacagt   3600
ccccgagaag ttggggggag gggtcggcaa ttgaaccggt gcctagagaa ggtggcgcgg   3660
ggtaaactgg gaaagtgatg tcgtgtactg gctccgcctt tttcccgagg gtgggggaga   3720
accgtatata agtgcagtag tcgccgtgaa cgttcttttt cgcaacgggt ttgccgccag   3780
aacacaggta agtgccgtgt gtggttcccg cgggcctggc ctctttacgg gttatggccc   3840
ttgcgtgcct tgaattactt ccacgcccct ggctgcagta cgtgattctt gatcccgagc   3900
ttcgggttgg aagtgggtgg gagagttcga ggccttgcgc ttaaggagcc ccttcgcctc   3960
gtgcttgagt tgaggcctgg cctgggcgct ggggccgccg cgtgcgaatc tggtggcacc   4020
ttcgcgcctg tctcgctgct ttcgataagt ctctagccat ttaaaatttt tgatgacctg   4080
ctgcgacgct ttttttctgg caagatagtc ttgtaaatgc gggccaagat ctgcacactg   4140
gtatttcggt ttttggggcc gcgggcggcg acggggcccg tgcgtcccag cgctcatgtt   4200
cggcgaggcg gggcctgcga gcgcggccac cgagaatcgg acgggggtag tctcaagctg   4260
gccggcctgc tctggtgcct ggcctcgcgc cgccgtgtat cgccccgccc tgggcggcaa   4320
ggctggcccg gtcggcacca gttgcgtgag cggaaagatg gccgcttccc ggccctgctg   4380
cagggagctc aaaatggagg acgcggcgct cgggagagcg ggcgggtgag tcacccacac   4440
aaaggaaaag ggcctttccg tcctcagccg tcgcttcatg tgactccacg gagtaccggg   4500
cgccgtccag gcacctcgat tagttctcga gcttttggag tacgtcgtct ttaggttggg   4560
gggaggggtt ttatgcgatg gagtttcccc acactgagtg ggtggagact gaagttaggc   4620
cagcttggca cttgatgtaa ttctccttgg aatttgccct ttttgagttt ggatcttggt   4680
tcattctcaa gcctcagaca gtggttcaaa gtttttttct tccatttcag gtgtcgtgag   4740
ccaccatgga gagcgacgag agcggcctgc ccgccatgga gatcgagtgc cgcatcaccg   4800
gcaccctgaa cggcgtggag ttcgagctgg tgggcggcgg agagggcacc cccgagcagg   4860
gccgcatgac caacaagatg aagagcacca aaggcgccct gaccttcagc ccctacctgc   4920
tgagccacgt gatgggctac ggcttctacc acttcggcac ctaccccagc ggctacgaga   4980
```

-continued

```
acccettcct gcacgccatc aacaacggcg gctacaccaa cacccgcatc gagaagtacg   5040
aggacggcgg cgtgctgcac gtgagcttca gctaccgcta cgaggccggc cgcgtgatcg   5100
gcgacttcaa ggtgatgggc accggcttcc ccgaggacag cgtgatcttc accgacaaga   5160
tcatccgcag caacgccacc gtggagcacc tgcaccccat gggcgataac gatctggatg   5220
gcagcttcac ccgcaccttc agcctgcgcg acggcggcta ctacagctcc gtggtggaca   5280
gccacatgca cttcaagagc gccatccacc ccagcatcct gcagaacggg ggacccatgt   5340
tcgccttccg ccgcgtggag gaggatcaca gcaacaccga gctgggcatc gtggagtacc   5400
agcacgcctt caagaccccg gatgcagatg ccggtgaaga aggaagcgga gctactaact   5460
tcagcctgct gaagcaggct ggagacgtgg aggagaaccc tggacctatg gcttccaagg   5520
tgtacgaccc cgagcaacgc aaacgcatga tcactgggcc tcagtggtgg gctcgctgca   5580
agcaaatgaa cgtgctggac tccttcatca actactatga ttccgagaag cacgccgaga   5640
acgccgtgat ttttctgcat ggtaacgctg cctccagcta cctgtggagg cacgtcgtgc   5700
ctcacatcga gcccgtggct agatgcatca tccctgatct gatcggaatg ggtaagtccg   5760
gcaagagcgg gaatggctca tatcgcctcc tggatcacta caagtacctc accgcttggt   5820
tcgagctgct gaaccttcca aagaaaatca tctttgtggg ccacgactgg ggggcttgtc   5880
tggcctttca ctactcctac gagcaccaag acaagatcaa ggccatcgtc catgctgaga   5940
gtgtcgtgga cgtgatcgag tcctgggacg agtggcctga catcgaggag gacatcgccc   6000
tgatcaagag cgaagagggc gagaaaatgg tgcttgagaa taacttcttc gtcgagacca   6060
tgctcccaag caagatcatg cggaaactgg agcctgagga gttcgctgcc tacctggagc   6120
cattcaagga gaagggcgag gttagacggc ctaccctctc ctggcctcgc gagatccctc   6180
tcgttaaggg aggcaagccc gatgtcgtcc agattgtccg caactacaac gcctaccttc   6240
gggccagcga cgatctgcct aagatgttca tcgagtccga ccctgggttc ttttccaacg   6300
ctattgtcga gggagctaag aagttcccta acaccgagtt cgtgaaggtg aagggcctcc   6360
acttcagcca ggaggacgct ccagatgaaa tgggtaagta catcaagagc ttcgtggagc   6420
gcgtgctgaa gaacgagcag taagctcact gcccatgatg cagagctttc aaggataggc   6480
tttattctgc aagcaatcaa ataataaatc tattctgcta agagatcaca catggttgtc   6540
ttcagttctt tttttatgtc tttttaaata tatgagccac aaagggtttt atgttgaggg   6600
atgtgtttat gtgtatttat acatggctat gtgtgtttgt gtcatgtgca cactccacac   6660
ttttttgttt acgttagatg tgggttttga tgagcaaata aaagaactag gcaataaaga   6720
aacttgtaca tgggagttct gcaagtggga gtaaaaggtg caggagaaat ctggttggaa   6780
gaaagacctc tataggacag gactcctcag aaacagatgt tttggaagag atggggaaag   6840
gttcagtgaa gggggctgaa ccccccttccc tggattgcag cacagcagcg aggaaggggc   6900
tcaacgaaga aaaagtgttc ctagctttag gaagtcaagg tttaggcagg gatagccatt   6960
ctattttatt aggggcaata ctatttccaa cggcatctgg cttttctcag cccttgtgag   7020
gctctacagg gaggttgagg tgttagagat cagagcagga aacaggtttt tctttccacg   7080
gtaactacaa tgaagtgatc cttactttac taaggaactt ttcattttaa gtgttgacgc   7140
atgcctaaag aggtgaaatt aatcccatac ccttaagtct acagactggt cacagcattt   7200
caaggaggag acctcattgt aagctactag ggaggtgggg acttaggtga aggaaatgag   7260
ccagcagaag ctcacaagtc agcatcagcg tgtcatgtct cagcagcaga acagcacggt   7320
cagatgaaaa tatagtgtga agaatttgta taacattaat tgagaaggca gattcactgg   7380
```

-continued agttcttata taattgaaag ttaatgcacg ttaataagca agagtttagt ttaatgtgat 7440
ggtgttatga acttaacgct tgtgtctcca gaaaattcac atgctgaatc cccaactccc 7500
aattggctcc atttgtgggg gaggctttgg aaaagtaatc aggtttagag gggctcatga 7560
gagcagatcc ccatcataga attattttcc tcatcagaag cagagagatt agccatttct 7620
cttccttctg gtgaggacac agtgggaagt cagccacctt agggataaca gggtaatgct 7680
cttcagatgg acagtcagac tgaagagctg gcaaacagct attatgggta ttatgggtga 7740
cgtcaggtgg cacttttcgg ggaaatgtgc gcggaacccc tatttgttta tttttctaaa 7800
tacattcaaa tatgtatccg ctcatgagac aataaccctg ataaatgctt caataatatt 7860
gaaaaaggaa gagtatgagt attcaacatt tccgtgtcgc ccttattccc ttttttgcgg 7920
cattttgcct tcctgttttt gctcacccag aaacgctggt gaaagtaaaa gatgctgaag 7980
atcagttggg tgcacgagtg ggttacatcg aactggatct caacagcggt aagatccttg 8040
agagttttcg ccccgaagaa cgttttccaa tgatgagcac ttttaaagtt ctgctatgtg 8100
gcgcggtatt atcccgtatt gacgccgggc aagagcaact cggtcgccgc atacactatt 8160
ctcagaatga cttggttgag tactcaccag tcacagaaaa gcatcttacg gatggcatga 8220
cagtaagaga attatgcagt gctgccataa ccatgagtga taacactgcg gccaacttac 8280
ttctgacaac gatcggagga ccgaaggagc taaccgcttt tttgcacaac atgggggatc 8340
atgtaactcg ccttgatcgt tgggaaccgg agctgaatga agccatacca aacgacgagc 8400
gtgacaccac gatgcctgta gcaatggcaa caacgttgcg caaactatta actggcgaac 8460
tacttactct agcttcccgg caacaattaa tagactggat ggaggcggat aaagttgcag 8520
gaccacttct gcgctcggcc cttccggctg gctggtttat tgctgataaa tctggagccg 8580
gtgagcgtgg gtctcgcggt atcattgcag cactggggcc agatggtaag ccctcccgta 8640
tcgtagttat ctacacgacg gggagtcagg caactatgga tgaacgaaat agacagatcg 8700
ctgagatagg tgcctcactg attaagcatt ggtaactgtc agaccaagtt tactcatata 8760
tactttagat tgatttaaaa cttcattttt aatttaaaag gatctaggtg aagatccttt 8820
ttgataatct catgaccaaa atcccttaac gtgagttttc gttccactga gcgtcagacc 8880
ccgtagaaaa gatcaaagga tcttcttgag atcctttttt tctgcgcgta atctgctgct 8940
tgcaaacaaa aaaaccaccg ctaccagcgg tggtttgttt gccggatcaa gagctaccaa 9000
ctctttttcc gaaggtaact ggcttcagca gagcgcagat accaaatact gttcttctag 9060
tgtagccgta gttaggccac cacttcaaga actctgtagc accgcctaca tacctcgctc 9120
tgctaatcct gttaccagtg gctgctgcca gtggcgataa gtcgtgtctt accgggttgg 9180
actcaagacg atagttaccg gataaggcgc agcggtcggg ctgaacgggg ggttcgtgca 9240
cacagcccag cttggagcga acgacctaca ccgaactgag atacctacag cgtgagctat 9300
gagaaagcgc cacgcttccc gaagggagaa aggcggacag gtatccggta agcggcaggg 9360
tcggaacagg agagcgcacg agggagcttc caggggggaaa cgcctggtat ctttatagtc 9420
ctgtcgggtt tcgccacctc tgacttgagc gtcgattttt gtgatgctcg tcaggggggc 9480
ggagcctatg gaaaaacgcc agcaacgcgg cctttttacg gttcctggcc ttttgctggc 9540
cttttgctca catgt 9555

<210> SEQ ID NO 12
<211> LENGTH: 14985
<212> TYPE: DNA

<213> ORGANISM: Artificial sequence
<220> FEATURE:
<223> OTHER INFORMATION: P439, Episomal REP/CAP + Transgene Plasmid
<220> FEATURE:
<221> NAME/KEY: misc_feature
<222> LOCATION: (2103)..(2137)
<223> OTHER INFORMATION: SEQ ID NO:14 Upstream half of beta-Actin intron
<220> FEATURE:
<221> NAME/KEY: misc_feature
<222> LOCATION: (2144)..(2398)
<223> OTHER INFORMATION: 5' end of the stop cassette
<220> FEATURE:
<221> NAME/KEY: misc_feature
<222> LOCATION: (4069)..(4287)
<223> OTHER INFORMATION: 3' end of stop cassette
<220> FEATURE:
<221> NAME/KEY: misc_feature
<222> LOCATION: (4295)..(4370)
<223> OTHER INFORMATION: SEQ ID NO:15 Downstream half of beta-Actin
intron
<220> FEATURE:
<221> NAME/KEY: misc_feature
<222> LOCATION: (7984)..(8124)
<223> OTHER INFORMATION: Left Inverted Terminal Repeat (ITR)
<220> FEATURE:
<221> NAME/KEY: misc_feature
<222> LOCATION: (11067)..(11207)
<223> OTHER INFORMATION: Right Inverted Terminal Repeat (ITR)

<400> SEQUENCE: 12
taactataac ggtcctaagg tagcgaagat atccgatcaa gaaagcactc cgggctccag 60
aaggagcctt ccaggccagc tttgagcata agctgctgat gagcagtgag tgtcttgagt 120
agtgttcagg gcagcatgtt accattcatg cttgacttct agccagtgtg acgagaggct 180
ggagtcaggt ctctagagag ttgagcagct ccagccttag atctcccagt cttatgcggt 240
gtgcccattc gctttgtgtc tgcagtcccc tggccacacc cagtaacagt tctgggatct 300
atgggagtag cttccttagt gagctttccc ttcaaatact ttgcaaccag gtagagaagt 360
ttggagtgaa ggtttttgttc ttcgtttctt cacaatatgg atatgcatct tcttttgaaa 420
atgttaaagt aaattacctc tcttttcaga tactgtcttc atgcgaactt ggtatcctgt 480
ttccatccca gccttctata acccagtaac atcttttttg aaaccagtgg gtgagaaaga 540
cacctggtca ggaacgcgga ccacaggaca actcaggctc acccacggca tcagactaaa 600
ggcaaacaag gactctgtat aaagtaccgg tggcatgtgt attagtggag atgcagcctg 660
tgctctgcag acagggagtc acacagacac ttttctataa tttcttaagt gctttgaatg 720
ttcaagtaga aagtctaaca ttaaatttga ttgaacaatt gtatattcat ggaatatttt 780
ggaacggaat accaaaaaat ggcaatagtg gttctttctg gatggaagac aaacttttct 840
tctttaaaat aaattttatt ttatatattt gaggttgacc acatgacctt aaggatacat 900
atagacagta aactggttac tacagtgaag caaattaaca tatctaccat cgtacatagt 960
tacatttttt tgtgtgacag gaacagctaa aatctacgta tttaacaaaa ctcctaaaga 1020
caatacattt ttattaacta tagccctcat gatgtacatt agatcctctc ttaaggtagc 1080
ccgaataaaa atagaaaaac aacaaatgtt aattttctat ttttatttgg tgtcgtactc 1140
aatccataat cgtcacaagc gttatagttt aagtacaaca atgtcgtcac cttgttggtg 1200
taattaggtt tacgccaaca gggtgataac aggcgcgccg gtcctgtatt agaggtcacg 1260
tgagtgtttt gcgacatttt gcgacaccat gtggtcacgc tgggtattta agcccgagtg 1320
agcacgcagg gtctccattt tgaagcggga ggtttgaacg cgcagccgcc atgccggggt 1380
tttacgagat tgtgattaag gtccccagcg accttgacga gcatctgccc ggcatttctg 1440

-continued

```
acagctttgt gaactgggtg gccgagaagg aatgggagtt gccgccagat tctgacatgg   1500
atctgaatct gattgagcag gcacccctga ccgtggccga gaagctgcag cgcgactttc   1560
tgacggaatg gcgccgtgtg agtaaggccc cggaggccct tttctttgtg caatttgaga   1620
agggagagag ctacttccac atgcacgtgc tcgtggaaac caccggggtg aaatccatgg   1680
ttttgggacg tttcctgagt cagattcgcg aaaaactgat tcagagaatt taccgcggga   1740
tcgagccgac tttgccaaac tggttcgcgg tcacaaagac cagaaatggc gccggaggcg   1800
ggaacaaggt ggtggatgag tgctacatcc ccaattactt gctccccaaa acccagcctg   1860
agctccagtg ggcgtggact aatatggaac agtatttaag cgcctgtttg aatctcacgg   1920
agcgtaaacg gttggtggcg cagcatctga cgcacgtgtc gcagacgcag gagcagaaca   1980
aagagaatca gaatcccaat tctgatgcgc cggtgatcag atcaaaaact tcagccaggt   2040
acatggagct ggtcgggtgg ctcgtggaca aggggattac ctcggagaag cagtggatcc   2100
aggtgggtgt ctttcctgcc tgagctgacc tgggcagacg cgtaattaag tatcatgata   2160
aactgacaaa gcggtatatc aagatactta atacatatgg tcctgtaaaa gtttaatgtg   2220
taagaagtat ttgttataaa agataaatat tcagaatctt ctttttaatt cctgatttta   2280
tttctatagg actgaaagac ttgctcgaga tgtcatgaag gagatgggag gccatcacat   2340
tctcacttca ctgcagctca acgtccccaa ttctaccggg taggggaggc gcttttccca   2400
aggcagtctg gagcatgcgc tttagcagcc ccgctgggca cttggcgcta cacaagtggc   2460
ctctggcctc gcacacattc cacatccacc ggtaggcgcc aaccggctcc gttctttggt   2520
ggccccttcg cgccaccttc tactcctccc ctagtcagga agttcccccc cgccccgcag   2580
ctcgcgtcgt gcaggacgtg acaaatggaa gtagcacgtc tcactagtct cgtgcagatg   2640
gacagcaccg ctgagcaatg gaagcgggta ggcctttggg gcagcggcca atagcagctt   2700
tgctccttcg ctttctgggc tcagaggctg ggaaggggtg ggtccggggg cgggctcagg   2760
ggcgggctca ggggcggggc gggcgcccga aggtcctccg gaggcccggc attctgcacg   2820
cttcaaaagc gcacgtctgc cgcgctgttc tcctcttcct catctccggg cctttcgacc   2880
tagcgggcag tgagcgcaac gcaattaatg tgagttagct cactcattag gcaccccagg   2940
ctttacactt tatgcttccg gctcgtatgt tgtgtggaat tgtgagcgga taacaatttc   3000
acacaggaaa cagctgccac catgattgaa caagatggat tgcacgcagg ttctccggcc   3060
gcttgggtgg agaggctatt cggctatgac tgggcacaac agacaatcgg ctgctctgat   3120
gccgccgtgt tccggctgtc agcgcagggg cgcccggttc tttttgtcaa gaccgacctg   3180
tccggtgccc tgaatgaact gcaagacgag gcagcgcggc tatcgtggct ggccacgacg   3240
ggcgttcctt gcgcagctgt gctcgacgtt gtcactgaag cgggaaggga ctggctgcta   3300
ttgggcgaag tgccggggca ggatctcctg tcatctcacc ttgctcctgc cgagaaagta   3360
tccatcatgg ctgatgcaat gcggcggctg catacgcttg atccggctac ctgcccattc   3420
gaccaccaag cgaaacatcg catcgagcga gcacgtactc ggatggaagc cggtcttgtc   3480
gatcaggatg atctggacga agagcatcag gggctcgcgc cagccgaact gttcgccagg   3540
ctcaaggcga gcatgcccga cggcgaggat ctcgtcgtga cccatggcga tgcctgcttg   3600
ccgaatatca tggtggaaaa tggccgcttt tctggattca tcgactgtgg ccggctgggt   3660
gtggcggacc gctatcagga catagcgttg gctacccgtg atattgctga agagcttggc   3720
ggcgaatggg ctgaccgctt cctcgtgctt tacggtatcg ccgctcccga ttcgcagcgc   3780
atcgccttct atcgccttct tgacgagttc ttctgagata cattgatgag tttggacaaa   3840
```

-continued

```
ccacaactag aatgcagtga aaaaaatgct ttatttgtga aatttgtgat gctattgctt   3900
tatttgtaac cattataagc tgcaataaac aagttaacaa caacaattgc attcatttta   3960
tgtttcgggt tcagggggag gtgtgggagg ttttttaaag caagtaaaac ctctacaaat   4020
gtggtatggc tgattatgat cgcatagtgt taccatcaac caccttaact tcatttttct   4080
tattcaatac ctaggtaggt agatgctaga ttctggaaat aaaatatgag tctcaagtgg   4140
tccttgtcct ctctcccagt caaattctga atctagttgg caagattctg aaatcaaggc   4200
atataatcag taataagtga tgatagaagg gtatatagaa ggctagccgt caacatctcc   4260
actgacaaag cggtttctcc aacgaattat cgattcggct gtggggtcct gtggtgtgtg   4320
gggagctgtc acatccaggg tcctcactgc ctgtcccctt ccctcctcag gaggaccagg   4380
cctcatacat ctccttcaat gcggcctcca actcgcggtc ccaaattaag gctgccttgg   4440
acaatgcggg aaagattatg agcctgacta aaaccgcccc cgactacctg gtgggccagc   4500
agcccgtgga ggacatttcc agcaatcgga tttataaaat tttggaacta aacgggtacg   4560
atccccaata tgcggcttcc gtctttctgg gatgggccac gaaaaagttc ggcaagagga   4620
acaccatctg gctgtttggg cctgcaacta ccgggaagac caacatcgcg gaggccatag   4680
cccacactgt gcccttctac gggtgcgtaa actggaccaa tgagaacttt cccttcaacg   4740
actgtgtcga caagatggtg atctggtggg aggaggggaa gatgaccgcc aaggtcgtgg   4800
agtcggccaa agccattctc ggaggaagca aggtgcgcgt ggaccagaaa tgcaagtcct   4860
cggcccagat agacccgact cccgtgatcg tcacctccaa caccaacatg tgcgccgtga   4920
ttgacgggaa ctcaacgacc ttcgaacacc agcagccgtt gcaagaccgg atgttcaaat   4980
ttgaactcac ccgccgtctg gatcatgact ttgggaaggt caccaagcag gaagtcaaag   5040
actttttccg gtgggcaaag gatcacgtgg ttgaggtgga gcatgagttc tacgtcaaaa   5100
agggtggagc caagaaaaga cccgccccca gtgacgcaga tataagtgag cccaaacggg   5160
tgcgcgagtc agttgcgcag ccatcgacgt cagacgcgga agcttcgatc aactacgcag   5220
acaggtacca aaacaaatgt tctcgtcacg tgggcatgaa tctgatgctg tttccctgca   5280
gacaatgcga gagaatgaat cagaattcaa atatctgctt cactcacgga cagaaagact   5340
gtttagagtg ctttcccgtg tcagaatctc aacccgtttc tgtcgtcaaa aaggcgtatc   5400
agaaactgtg ctacattcat catatcatgg gaaaggtgcc agacgcttgc actgcctgcg   5460
atctggtcaa tgtggatttg gatgactgca tctttgaaca ataaatgatt taaatcaggt   5520
atggctgccg atggttatct tccagattgg ctcgaggaca accttagtga agggattcgc   5580
gagtggtggg ctttgaaacc tggagcccct caacccaagg caaatcaaca acatcaagac   5640
aacgctcgag gtcttgtgct tccgggttac aaatacottg gacccggcaa cggactcgac   5700
aagggggagc cggtcaacgc agcagacgcg gcggccctcg agcacgacaa ggcctacgac   5760
cagcagctca aggccggaga caacccgtac ctcaagtaca accacgccga cgccgagttc   5820
caggagcggc tcaaagaaga tacgtctttt gggggcaacc tcgggcgagc agtcttccag   5880
gccaaaaaga ggcttcttga acctcttggt ctggttgagg aagcggctaa gacggctcct   5940
ggaaagaaga ggcctgtaga gcagtctcct caggaaccgg actcctccgc gggtattggc   6000
aaatcgggtg cacagcccgc taaaaagaga ctcaatttcg gtcagactgg cgacacagag   6060
tcagtcccag accctcaacc aatcggagaa cctcccgcag ccccctcagg tgtgggatct   6120
cttacaatgg cttcaggtgg tggcgcacca gtggcagaca ataacgaagg tgccgatgga   6180
```

-continued gtgggtagtt cctcgggaaa ttggcattgc gattcccaat ggctggggga cagagtcatc 6240
accaccagca cccgaacctg ggccctgccc acctacaaca atcacctcta caagcaaatc 6300
tccaacagca catctggagg atcttcaaat gacaacgcct acttcggcta cagcaccccc 6360
tgggggtatt ttgacttcaa cagattccac tgccacttct caccacgtga ctggcagcga 6420
ctcatcaaca acaactgggg attccggcct aagcgactca acttcaagct cttcaacatt 6480
caggtcaaag aggttacgga caacaatgga gtcaagacca tcgccaataa ccttaccagc 6540
acggtccagg tcttcacgga ctcagactat cagctcccgt acgtgctcgg gtcggctcac 6600
gagggctgcc tcccgccgtt cccagcggac gttttcatga ttcctcagta cgggtatctg 6660
acgcttaatg atggaagcca ggccgtgggt cgttcgtcct tttactgcct ggaatatttc 6720
ccgtcgcaaa tgctaagaac gggtaacaac ttccagttca gctacgagtt tgagaacgta 6780
cctttccata gcagctacgc tcacagccaa agcctggacc gactaatgaa tccactcatc 6840
gaccaatact tgtactatct ctcaaagact attaacggtt ctggacagaa tcaacaaacg 6900
ctaaaattca gtgtggccgg acccagcaac atggctgtcc agggaagaaa ctacatacct 6960
ggacccagct accgacaaca acgtgtctca accactgtga ctcaaaacaa caacagcgaa 7020
tttgcttggc ctggagcttc ttcttgggct ctcaatggac gtaatagctt gatgaatcct 7080
ggacctgcta tggccagcca caaagaagga gaggaccgtt tctttccttt gtctggatct 7140
ttaatttttg gcaaacaagg aactggaaga gacaacgtgg atgcggacaa agtcatgata 7200
accaacgaag aagaaattaa aactactaac ccggtagcaa cggagtccta tggacaagtg 7260
gccacaaacc accagagtgc ccaagcacag gcgcagaccg gctgggttca aaaccaagga 7320
atacttccgg gtatggtttg gcaggacaga gatgtgtacc tgcaaggacc catttgggcc 7380
aaaattcctc acacggacgg caactttcac ccttctccgc tgatgggagg gtttggaatg 7440
aagcacccgc ctcctcagat cctcatcaaa aacacacctg tacctgcgga tcctccaacg 7500
gccttcaaca aggacaagct gaactctttc atcacccagt attctactgg ccaagtcagc 7560
gtggagatcg agtgggagct gcagaaggaa aacagcaagc gctggaaccc ggagatccag 7620
tacacttcca actattacaa gtctaataat gttgaatttg ctgttaatac tgaaggtgta 7680
tatagtgaac cccgccccat tggcaccaga tacctgactc gtaatctgta attgcttgtt 7740
aatcaataaa ccgtttaatt cgtttcagtt gaactttggt ctctgcggtt taaacggtcc 7800
tgtattagag gtcacgtgag tgttttgcga cattttgcga caccatgtgg tcacgctggg 7860
tatttaagcc cgagtgagca cgcagggtct ccattttgaa gcgggaggtt tgaacgcgcg 7920
cggccgcccg aataaaaata gaaaaacaac aaatgttaat ttctatttt tatttggtct 7980
agacctgcag gcagctgcgc gctcgctcgc tcactgaggc cgcccgggca aagcccgggc 8040
gtcgggcgac ctttggtcgc ccggcctcag tgagcgagcg agcgcgcaga gagggagtgg 8100
ccaactccat cactaggggt tccttctaga cgtgaggctc cggtgcccgt cagtgggcag 8160
agcgcacatc gcccacagtc cccgagaagt tggggggagg ggtcggcaat tgaaccggtg 8220
cctagagaag gtggcgcggg gtaaactggg aaagtgatgt cgtgtactgg ctccgccttt 8280
ttcccgaggg tgggggagaa ccgtatataa gtgcagtagt cgccgtgaac gttctttttc 8340
gcaacgggtt tgccgccaga acacaggtaa gtgccgtgtg tggttcccgc gggcctggcc 8400
tctttacggg ttatggccct tgcgtgcctt gaattacttc cacgcccctg gctgcagtac 8460
gtgattcttg atcccgagct tcgggttgga agtgggtggg agagttcgag gccttgcgct 8520
taaggagccc cttcgcctcg tgcttgagtt gaggcctggc ctgggcgctg gggccgccgc 8580

-continued

```
gtgcgaatct ggtggcacct tcgcgcctgt ctcgctgctt tcgataagtc tctagccatt   8640
taaaattttt gatgacctgc tgcgacgctt tttttctggc aagatagtct tgtaaatgcg   8700
ggccaagatc tgcacactgg tatttcggtt tttggggccg cgggcggcga cggggcccgt   8760
gcgtcccagc gctcatgttc ggcgaggcgg ggcctgcgag cgcggccacc gagaatcgga   8820
cgggggtagt ctcaagctgg ccggcctgct ctggtgcctg gcctcgcgcc gccgtgtatc   8880
gccccgccct gggcggcaag gctggcccgg tcggcaccag ttgcgtgagc ggaaagatgg   8940
ccgcttcccg gccctgctgc agggagctca aaatggagga cgcggcgctc gggagagcgg   9000
gcgggtgagt cacccacaca aaggaaaagg gcctttccgt cctcagccgt cgcttcatgt   9060
gactccacgg agtaccgggc gccgtccagg cacctcgatt agttctcgag cttttggagt   9120
acgtcgtctt taggttgggg ggaggggttt tatgcgatgg agtttcccca cactgagtgg   9180
gtggagactg aagttaggcc agcttggcac ttgatgtaat tctccttgga atttgccctt   9240
tttgagtttg gatcttggtt cattctcaag cctcagacag tggttcaaag tttttttctt   9300
ccatttcagg tgtcgtgagc caccatggtg agcaagggcg aggaggataa catggccatc   9360
atcaaggagt tcatgcgctt caaggtgcac atggagggct ccgtgaacgg ccacgagttc   9420
gagatcgagg gcgagggcga gggccgcccc tacgagggca cccagaccgc caagctgaag   9480
gtgaccaagg gtggccccct gcccttcgcc tgggacatcc tgtcccctca gttcatgtac   9540
ggctccaagg cctacgtgaa gcaccccgcc gacatccccg actacttgaa gctgtccttc   9600
cccgagggct tcaagtggga gcgcgtgatg aacttcgagg acggcggcgt ggtgaccgtg   9660
acccaggact cctccctgca ggacggcgag ttcatctaca aggtgaagct gcgcggcacc   9720
aacttcccct ccgacggccc cgtaatgcag aagaagacca tgggctggga ggcctcctcc   9780
gagcggatgt accccgagga cggcgccctg aagggcgaga tcaagcagag gctgaagctg   9840
aaggacggcg gccactacga cgctgaggtc aagaccacct acaaggccaa gaagcccgtg   9900
cagctgcccg gcgcctacaa cgtcaacatc aagttggaca tcacctccca caacgaggac   9960
tacaccatcg tggaacagta cgaacgcgcc gagggccgcc actccaccgg cggcatggac  10020
gagctgtaca agggaagcgg acagtgtact aattatgctc tcttgaaatt ggctggagat  10080
gttgagagca accctggacc tatggcgacc cgcagccctg gcgtcgtgat tagtgatgat  10140
gaacccggtt atgaccttga tttattttgc atacctaatc attatgctga ggatttggaa  10200
agggtgttta ttcctcatgg actaattatg gacaggactg aacgtcttgc tcgagatgtg  10260
atgaaggaga tgggaggcca tcacattgta gccctctgtg tgctcaaggg gggctataaa  10320
ttctttgctg acctgctgga ttacatcaaa gcactgaata gaaatagtga tagatccatt  10380
cctatgactg tagattttat cagactgaag agctattgta atgaccagtc aacaggggac  10440
ataaaagtaa ttggtggaga tgatctctca actttaactg gaaagaatgt cttgattgtg  10500
gaagatataa ttgacactgg caaaacaatg cagactttgc tttccttggt caggcagtat  10560
aatccaaaga tggtcaaggt cgctagcttg ctggtgaaaa ggaccccacg aagtgttgga  10620
tataagccag actttgttgg atttgaaatt ccagacaagt ttgttgtagg atatgccctt  10680
gactataatg aatacttcag ggatttgaat catgtttgtg tcattagtga aactggaaaa  10740
gcaaaataca aagcctaaac gcgtggggga ggctaactga aacacggaag gagacaatac  10800
cggaaggaac ccgcgctatg acggcaataa aaagacagaa taaaacgcac ggtgttgggt  10860
cgtttgttca taaacgcggg gttcggtccc agggctggca ctctgtcgat accccaccga  10920
```

-continued

```
gaccccattg gggccaatac gcccgcgttt cttccttttc cccaccccac cccccaagtt  10980
cgggtgaagg cccagggctc gcagccaacg tcggggcggc aggccctgcc atagccatct  11040
atgtcgggtg cggagaaaga ggtaatagga acccctagtg atggagttgg ccactccctc  11100
tctgcgcgct cgctcgctca ctgaggccgg gcgaccaaag gtcgcccgac gcccgggctt  11160
tgcccgggcg gcctcagtga gcgagcgagc gcgcagctgc ctgcaggtag ggataacagg  11220
gtaatacttg aattttcaag tataaagtct agtgctaaat ttaatttgaa caactgtata  11280
gtttttgctg gttgggggaa ggaaaaaaaa tggtggcagt gtttttttca gaattagaag  11340
tgaaatgaaa acttgttgtg tgtgaggatt tctaatgcca tgtggtggtt gcatactgag  11400
tgaagccggt gagcattctg ccatgtcacc ccctcgtgct cagtaatgta ctttacagaa  11460
atcctaaact caaaagattg atataaacca tgcttcttgt gtatatccgg tctcttctct  11520
gggtagtctc actcagcctg catttctgcc atcccttgtc ctctggcccc cgtcgcccag  11580
atatctggca aacagctatt atgggtatta tgggtttcag ggagtggcgc agctgcttca  11640
tccccgtggc ccgttgctcg cgtttgctgg cggtgtcccc ggaagaaata tatttgcatg  11700
tctttagttc tatgatgaca caaaccccgc ccagcgtctt gtcattggcg aaaacacgca  11760
gatgcagtcg gggcggcgcg gtcccaggtc cacttcgcat attaaggtga cgcgtgtggc  11820
ctcgaacaca gagcgacggc caccatgacc gagtacaagc ccacggtgcg cctcgccacc  11880
cgcgacgacg tcccccgggc cgtacgcacc ctcgccgccg cgttcgccga ctaccccgcc  11940
acgcgccaca ccgttgaccc ggaccgccac atcgagcggg tcaccgagct gcaagaactc  12000
ttcctcacgc gcgtcgggct cgacatcggc aaggtgtggg tcgcggacga cggcgccgcg  12060
gtggcggtct ggaccacgcc ggagagcgtc gaagcggggg cggtgttcgc cgagatcggc  12120
ccgcgcatgg ccgagttgag cggttcccgg ctggccgcgc agcaacagat ggaaggcctc  12180
ctggcgccgc accggcccaa ggagcccgcg tggttcctgg ccaccgtcgg cgtctcgccc  12240
gaccaccagg gcaagggtct gggcagcgcc gtcgtgctcc ccggagtgga ggcggccgag  12300
cgcgccgggg tgcccgcctt cctggagacc tccgcgcccc gcaacctccc cttctacgag  12360
cggctcggct tcaccgtcac cgccgacgtc gaggtgcccg aaggaccgcg cacctggtgc  12420
atgacccgca agcccggtgc ctgatgtgcc ttctagttgc cagccatctg ttgtttgccc  12480
ctcccccgtg ccttccttga ccctggaagg tgccactccc actgtccttt cctaataaaa  12540
tgaggaaatt gcatcgcatt gtctgagtag gtgtcattct attctggggg gtggggtggg  12600
gcaggacagc aagggggagg attgggaaga caatagcagg catgctgggg atgcggtggg  12660
ctctatggtc cccccttatta accctaaacg ggtagcatat gcttcccggg tagtagtata  12720
tactatccag actaacccta attcaatagc atatgttacc caacgggaag catatgctat  12780
cgaattaggg ttagtaaaag ggtcctaagg aacagcgatc tggatagcat atgctatcct  12840
aatctatatc tgggtagcat atgctatcct aatctatatc tgggtagcat aggctatcct  12900
aatctatatc tgggtagcat atgctatcct aatctatatc tgggtagtat atgctatcct  12960
aatttatatc tgggtagcat aggctatcct aatctatatc tgggtagcat atgctatcct  13020
aatctatatc tgggtagtat atgctatcct aatctgtatc cgggtagcat atgctatcct  13080
catgcatata cagtcagcat atgataccca gtagtagagt gggagtgcta tcctttgcat  13140
atgccgccac ctcccaagga ttatgggtga cgtcaggtgg cacttttcgg ggaaatgtgc  13200
gcggaacccc tatttgttta tttttctaaa tacattcaaa tatgtatccg ctcatgagac  13260
aataaccctg ataaatgctt caataatatt gaaaaaggaa gagtatgagt attcaacatt  13320
```

```
tccgtgtcgc ccttattccc ttttttgcgg cattttgcct tcctgttttt gctcacccag  13380

aaacgctggt gaaagtaaaa gatgctgaag atcagttggg tgcacgagtg ggttacatcg  13440

aactggatct caacagcggt aagatccttg agagttttcg ccccgaagaa cgttttccaa  13500

tgatgagcac ttttaaagtt ctgctatgtg gcgcggtatt atcccgtatt gacgccgggc  13560

aagagcaact cggtcgccgc atacactatt ctcagaatga cttggttgag tactcaccag  13620

tcacagaaaa gcatcttacg gatggcatga cagtaagaga attatgcagt gctgccataa  13680

ccatgagtga taacactgcg gccaacttac ttctgacaac gatcggagga ccgaaggagc  13740

taaccgcttt tttgcacaac atgggggatc atgtaactcg ccttgatcgt tgggaaccgg  13800

agctgaatga agccatacca aacgacgagc gtgacaccac gatgcctgta gcaatggcaa  13860

caacgttgcg caaactatta actggcgaac tacttactct agcttcccgg caacaattaa  13920

tagactggat ggaggcggat aaagttgcag gaccacttct gcgctcggcc cttccggctg  13980

gctggtttat tgctgataaa tctggagccg gtgagcgtgg gtctcgcggt atcattgcag  14040

cactggggcc agatggtaag ccctcccgta tcgtagttat ctacacgacg gggagtcagg  14100

caactatgga tgaacgaaat agacagatcg ctgagatagg tgcctcactg attaagcatt  14160

ggtaactgtc agaccaagtt tactcatata tactttagat tgatttaaaa cttcattttt  14220

aatttaaaag gatctaggtg aagatccttt ttgataatct catgaccaaa atcccttaac  14280

gtgagttttc gttccactga gcgtcagacc ccgtagaaaa gatcaaagga tcttcttgag  14340

atcctttttt tctgcgcgta atctgctgct tgcaaacaaa aaaaccaccg ctaccagcgg  14400

tggtttgttt gccggatcaa gagctaccaa ctctttttcc gaaggtaact ggcttcagca  14460

gagcgcagat accaaatact gttcttctag tgtagccgta gttaggccac cacttcaaga  14520

actctgtagc accgcctaca tacctcgctc tgctaatcct gttaccagtg gctgctgcca  14580

gtggcgataa gtcgtgtctt accgggttgg actcaagacg atagttaccg gataaggcgc  14640

agcggtcggg ctgaacgggg ggttcgtgca cacagcccag cttggagcga acgacctaca  14700

ccgaactgag atacctacag cgtgagctat gagaaagcgc cacgcttccc gaagggagaa  14760

aggcggacag gtatccggta agcggcaggg tcggaacagg agagcgcacg agggagcttc  14820

caggggggaaa cgcctggtat ctttatagtc ctgtcgggtt tcgccacctc tgacttgagc  14880

gtcgattttt gtgatgctcg tcaggggggc ggagcctatg gaaaaacgcc agcaacgcgg  14940

cctttttacg gttcctggcc ttttgctggc cttttgctca catgt                  14985
```

<210> SEQ ID NO 13
<211> LENGTH: 4409
<212> TYPE: DNA
<213> ORGANISM: Artificial sequence
<220> FEATURE:
<223> OTHER INFORMATION: REP2/CAP9 Sequence Prior to Inserting STOP Cassette

<400> SEQUENCE: 13

```
ggtcctgtat tagaggtcac gtgagtgttt tgcgacattt tgcgacacca tgtggtcacg     60

ctgggtattt aagcccgagt gagcacgcag ggtctccatt ttgaagcggg aggtttgaac    120

gcgcagccgc catgccgggg ttttacgaga ttgtgattaa ggtccccagc gaccttgacg    180

agcatctgcc cggcatttct gacagctttg tgaactgggt ggccgagaag gaatgggagt    240

tgccgccaga ttctgacatg gatctgaatc tgattgagca ggcacccctg accgtggccg    300

agaagctgca gcgcgacttt ctgacggaat ggcgccgtgt gagtaaggcc ccggaggccc    360
```

-continued

```
ttttctttgt gcaatttgag aagggagaga gctacttcca catgcacgtg ctcgtggaaa    420
ccaccggggt gaaatccatg gttttgggac gtttcctgag tcagattcgc gaaaaactga    480
ttcagagaat ttaccgcggg atcgagccga ctttgccaaa ctggttcgcg gtcacaaaga    540
ccagaaatgg cgccggaggc gggaacaagg tggtggatga gtgctacatc cccaattact    600
tgctccccaa aacccagcct gagctccagt gggcgtggac taatatggaa cagtatttaa    660
gcgcctgttt gaatctcacg gagcgtaaac ggttggtggc gcagcatctg acgcacgtgt    720
cgcagacgca ggagcagaac aaagagaatc agaatcccaa ttctgatgcg ccggtgatca    780
gatcaaaaac ttcagccagg tacatggagc tggtcgggtg gctcgtggac aaggggatta    840
cctcggagaa gcagtggatc caggaggacc aggcctcata catctccttc aatgcggcct    900
ccaactcgcg gtcccaaatt aaggctgcct tggacaatgc gggaaagatt atgagcctga    960
ctaaaaccgc cccgactac ctggtgggcc agcagcccgt ggaggacatt tccagcaatc    1020
ggatttataa aattttggaa ctaaacgggt acgatcccca atatgcggct tccgtctttc   1080
tgggatgggc cacgaaaaag ttcggcaaga ggaacaccat ctggctgttt gggcctgcaa   1140
ctaccgggaa gaccaacatc gcggaggcca tagcccacac tgtgcccttc tacgggtgcg   1200
taaactggac caatgagaac tttcccttca acgactgtgt cgacaagatg gtgatctggt   1260
gggaggaggg gaagatgacc gccaaggtcg tggagtcggc caaagccatt ctcggaggaa   1320
gcaaggtgcg cgtggaccag aaatgcaagt cctcggccca gatagacccg actcccgtga   1380
tcgtcacctc caacaccaac atgtgcgccg tgattgacgg gaactcaacg accttcgaac   1440
accagcagcc gttgcaagac cggatgttca aatttgaact cacccgccgt ctggatcatg   1500
actttgggaa ggtcaccaag caggaagtca aagacttttt ccggtgggca aaggatcacg   1560
tggttgaggt ggagcatgag ttctacgtca aaaagggtgg agccaagaaa agacccgccc   1620
ccagtgacgc agatataagt gagcccaaac gggtgcgcga gtcagttgcg cagccatcga   1680
cgtcagacgc ggaagcttcg atcaactacg cagacaggta ccaaaacaaa tgttctcgtc   1740
acgtgggcat gaatctgatg ctgtttccct gcagacaatg cgagagaatg aatcagaatt   1800
caaatatctg cttcactcac ggacagaaag actgtttaga gtgctttccc gtgtcagaat   1860
ctcaacccgt ttctgtcgtc aaaaaggcgt atcagaaact gtgctacatt catcatatca   1920
tgggaaaggt gccagacgct tgcactgcct gcgatctggt caatgtggat ttggatgact   1980
gcatctttga acaataaatg atttaaatca ggtatggctg ccgatggtta tcttccagat   2040
tggctcgagg acaaccttag tgaagggatt cgcgagtggt gggctttgaa acctggagcc   2100
cctcaaccca aggcaaatca acaacatcaa gacaacgctc gaggtcttgt gcttccgggt   2160
tacaaatacc ttggacccgg caacggactc gacaaggggg agccggtcaa cgcagcagac   2220
gcggcggccc tcgagcacga caaggcctac gaccagcagc tcaaggccgg agacaacccg   2280
tacctcaagt acaaccacgc cgacgccgag ttccaggagc ggctcaaaga agatacgtct   2340
tttgggggca acctcgggcg agcagtcttc caggccaaaa agaggcttct tgaacctctt   2400
ggtctggttg aggaagcggc taagacggct cctggaaaga agaggcctgt agagcagtct   2460
cctcaggaac cggactcctc cgcgggtatt ggcaaatcgg gtgcacagcc cgctaaaaag   2520
agactcaatt tcggtcagac tggcgacaca gagtcagtcc cagaccctca accaatcgga   2580
gaacctcccg cagccccctc aggtgtggga tctcttacaa tggcttcagg tggtggcgca   2640
ccagtggcag acaataacga aggtgccgat ggagtgggta gttcctcggg aaattggcat   2700
```

-continued tgcgattccc aatggctggg ggacagagtc atcaccacca gcacccgaac ctgggccctg 2760
cccacctaca acaatcacct ctacaagcaa atctccaaca gcacatctgg aggatcttca 2820
aatgacaacg cctacttcgg ctacagcacc ccctgggggt attttgactt caacagattc 2880
cactgccact tctcaccacg tgactggcag cgactcatca acaacaactg gggattccgg 2940
cctaagcgac tcaacttcaa gctcttcaac attcaggtca aagaggttac ggacaacaat 3000
ggagtcaaga ccatcgccaa taaccttacc agcacggtcc aggtcttcac ggactcagac 3060
tatcagctcc cgtacgtgct cgggtcggct cacgagggct gcctcccgcc gttcccagcg 3120
gacgttttca tgattcctca gtacgggtat ctgacgctta atgatggaag ccaggccgtg 3180
ggtcgttcgt ccttttactg cctggaatat ttcccgtcgc aaatgctaag aacgggtaac 3240
aacttccagt tcagctacga gtttgagaac gtacctttcc atagcagcta cgctcacagc 3300
caaagcctgg accgactaat gaatccactc atcgaccaat acttgtacta tctctcaaag 3360
actattaacg gttctggaca gaatcaacaa acgctaaaat tcagtgtggc cggacccagc 3420
aacatggctg tccagggaag aaactacata cctggaccca gctaccgaca acaacgtgtc 3480
tcaaccactg tgactcaaaa caacaacagc gaatttgctt ggcctggagc ttcttcttgg 3540
gctctcaatg gacgtaatag cttgatgaat cctggacctg ctatggccag ccacaaagaa 3600
ggagaggacc gtttctttcc tttgtctgga tctttaattt ttggcaaaca aggaactgga 3660
agagacaacg tggatgcgga caaagtcatg ataaccaacg aagaagaaat taaaactact 3720
aacccggtag caacggagtc ctatggacaa gtggccacaa accaccagag tgcccaagca 3780
caggcgcaga ccggctgggt tcaaaaccaa ggaatacttc cgggtatggt ttggcaggac 3840
agagatgtgt acctgcaagg acccatttgg gccaaaattc ctcacacgga cggcaacttt 3900 caccettctc cgctgatggg agggtttgga atgaagcacc cgcctcctca gatcctcatc 3960
aaaaacacac ctgtacctgc ggatcctcca acggccttca acaaggacaa gctgaactct 4020
ttcatcaccc agtattctac tggccaagtc agcgtggaga tcgagtggga gctgcagaag 4080
gaaaacagca agcgctggaa cccggagatc cagtacactt ccaactatta caagtctaat 4140
aatgttgaat ttgctgttaa tactgaaggt gtatatagtg aaccccgccc cattggcacc 4200
agatacctga ctcgtaatct gtaattgctt gttaatcaat aaaccgttta attcgtttca 4260
gttgaacttt ggtctctgcg gtttaaacgg tcctgtatta gaggtcacgt gagtgttttg 4320
cgacattttg cgacaccatg tggtcacgct gggtatttaa gcccgagtga gcacgcaggg 4380
tctccatttt gaagcgggag gtttgaacg 4409

<210> SEQ ID NO 14
<211> LENGTH: 35
<212> TYPE: DNA
<213> ORGANISM: Artificial sequence
<220> FEATURE:
<223> OTHER INFORMATION: Upstream half of beta-Actin Intron

<400> SEQUENCE: 14
gtgggtgtct ttcctgcctg agctgacctg ggcag 35

<210> SEQ ID NO 15
<211> LENGTH: 76
<212> TYPE: DNA
<213> ORGANISM: Artificial sequence
<220> FEATURE:
<223> OTHER INFORMATION: Downstream half of beta-Actin intron

<400> SEQUENCE: 15

```
tcggctgtgg ggtcctgtgg tgtgtgggga gctgtcacat ccagggtcct cactgcctgt     60

ccccttccct cctcag                                                     76


<210> SEQ ID NO 16
<211> LENGTH: 2144
<212> TYPE: DNA
<213> ORGANISM: Artificial sequence
<220> FEATURE:
<223> OTHER INFORMATION: Transcriptional STOP cassette

<400> SEQUENCE: 16

aattaagtat catgataaac tgacaaagcg gtatatcaag atacttaata catatggtcc     60

tgtaaaagtt taatgtgtaa gaagtatttg ttataaaaga taaatattca gaatcttctt    120

tttaattcct gattttattt ctataggact gaaagacttg ctcgagatgt catgaaggag    180

atgggaggcc atcacattct cacttcactg cagctcaacg tccccaattc taccgggtag    240

gggaggcgct tttcccaagg cagtctggag catgcgcttt agcagccccg ctgggcactt    300

ggcgctacac aagtggcctc tggcctcgca cacattccac atccaccggt aggcgccaac    360

cggctccgtt ctttggtggc cccttcgcgc caccttctac tcctccccta gtcaggaagt    420

tcccccccgc cccgcagctc gcgtcgtgca ggacgtgaca aatggaagta gcacgtctca    480

ctagtctcgt gcagatggac agcaccgctg agcaatggaa gcgggtaggc ctttggggca    540

gcggccaata gcagctttgc tccttcgctt tctgggctca gaggctggga aggggtgggt    600

ccgggggcgg gctcaggggc gggctcaggg gcggggcggg cgcccgaagg tcctccggag    660

gcccggcatt ctgcacgctt caaaagcgca cgtctgccgc gctgttctcc tcttcctcat    720

ctccgggcct ttcgacctag cgggcagtga gcgcaacgca attaatgtga gttagctcac    780

tcattaggca ccccaggctt tacactttat gcttccggct cgtatgttgt gtggaattgt    840

gagcggataa caatttcaca caggaaacag ctgccaccat gattgaacaa gatggattgc    900

acgcaggttc tccggccgct tgggtggaga ggctattcgg ctatgactgg gcacaacaga    960

caatcggctg ctctgatgcc gccgtgttcc ggctgtcagc gcaggggcgc ccggttcttt   1020

ttgtcaagac cgacctgtcc ggtgccctga atgaactgca agacgaggca gcgcggctat   1080

cgtggctggc cacgacgggc gttccttgcg cagctgtgct cgacgttgtc actgaagcgg   1140

gaagggactg gctgctattg ggcgaagtgc cggggcagga tctcctgtca tctcaccttg   1200

ctcctgccga gaaagtatcc atcatggctg atgcaatgcg gcggctgcat acgcttgatc   1260

cggctacctg cccattcgac caccaagcga aacatcgcat cgagcgagca cgtactcgga   1320

tggaagccgg tcttgtcgat caggatgatc tggacgaaga gcatcagggg ctcgcgccag   1380

ccgaactgtt cgccaggctc aaggcgagca tgcccgacgg cgaggatctc gtcgtgaccc   1440

atggcgatgc ctgcttgccg aatatcatgg tggaaaatgg ccgcttttct ggattcatcg   1500

actgtggccg gctgggtgtg gcggaccgct atcaggacat agcgttggct acccgtgata   1560

ttgctgaaga gcttggcggc gaatgggctg accgcttcct cgtgctttac ggtatcgccg   1620

ctcccgattc gcagcgcatc gccttctatc gccttcttga cgagttcttc tgagatacat   1680

tgatgagttt ggacaaacca caactagaat gcagtgaaaa aaatgcttta tttgtgaaat   1740

ttgtgatgct attgctttat ttgtaaccat tataagctgc aataaacaag ttaacaacaa   1800

caattgcatt cattttatgt ttcgggttca gggggaggtg tgggaggttt tttaaagcaa   1860

gtaaaacctc tacaaatgtg gtatggctga ttatgatcgc atagtgttac catcaaccac   1920
```

```
cttaacttca tttttcttat tcaataccta ggtaggtaga tgctagattc tggaaataaa   1980

atatgagtct caagtggtcc ttgtcctctc tcccagtcaa attctgaatc tagttggcaa   2040

gattctgaaa tcaaggcata taatcagtaa taagtgatga tagaagggta tatagaaggc   2100

tagccgtcaa catctccact gacaaagcgg tttctccaac gaat                     2144
```

<210> SEQ ID NO 17
<211> LENGTH: 170
<212> TYPE: DNA
<213> ORGANISM: Artificial sequence
<220> FEATURE:
<223> OTHER INFORMATION: Strong Splice Acceptor

<400> SEQUENCE: 17

```
gtcctgtaaa agtttaatgt gtaagaagta tttgttataa aagataaata ttcagaatct     60

tctttttaat tcctgatttt atttctatag gactgaaaga cttgctcgag atgtcatgaa    120

ggagatggga ggccatcaca ttctcacttc actgcagctc aacgtcccca               170
```

<210> SEQ ID NO 18
<211> LENGTH: 1672
<212> TYPE: DNA
<213> ORGANISM: Artificial sequence
<220> FEATURE:
<223> OTHER INFORMATION: Neomycin/ Kanamycin Resistance Gene

<400> SEQUENCE: 18

```
attctaccgg gtaggggagg cgcttttccc aaggcagtct ggagcatgcg ctttagcagc     60

cccgctgggc acttggcgct acacaagtgg cctctggcct cgcacacatt ccacatccac    120

cggtaggcgc caaccggctc cgttctttgg tggccccttc gcgccacctt ctactcctcc    180

cctagtcagg aagttccccc ccgccccgca gctcgcgtcg tgcaggacgt gacaaatgga    240

agtagcacgt ctcactagtc tcgtgcagat ggacagcacc gctgagcaat ggaagcgggt    300

aggcctttgg ggcagcggcc aatagcagct ttgctccttc gctttctggg ctcagaggct    360

gggaaggggt gggtccgggg gcgggctcag gggcgggctc aggggcgggg cgggcgcccg    420

aaggtcctcc ggaggcccgg cattctgcac gcttcaaaag cgcacgtctg ccgcgctgtt    480

ctcctcttcc tcatctccgg gcctttcgac ctagcgggca gtgagcgcaa cgcaattaat    540

gtgagttagc tcactcatta ggcaccccag gctttacact ttatgcttcc ggctcgtatg    600

ttgtgtggaa ttgtgagcgg ataacaattt cacacaggaa acagctgcca ccatgattga    660

acaagatgga ttgcacgcag gttctccggc cgcttgggtg gagaggctat tcggctatga    720

ctgggcacaa cagacaatcg gctgctctga tgccgccgtg ttccggctgt cagcgcaggg    780

gcgcccggtt ctttttgtca agaccgacct gtccggtgcc ctgaatgaac tgcaagacga    840

ggcagcgcgg ctatcgtggc tggccacgac gggcgttcct tgcgcagctg tgctcgacgt    900

tgtcactgaa gcgggaaggg actggctgct attgggcgaa gtgccggggc aggatctcct    960

gtcatctcac cttgctcctg ccgagaaagt atccatcatg gctgatgcaa tgcggcggct   1020

gcatacgctt gatccggcta cctgcccatt cgaccaccaa gcgaaacatc gcatcgagcg   1080

agcacgtact cggatggaag ccggtcttgt cgatcaggat gatctggacg aagagcatca   1140

ggggctcgcg ccagccgaac tgttcgccag gctcaaggcg agcatgcccg acggcgagga   1200

tctcgtcgtg acccatggcg atgcctgctt gccgaatatc atggtggaaa atggccgctt   1260

ttctggattc atcgactgtg gccggctggg tgtggcggac cgctatcagg acatagcgtt   1320

ggctacccgt gatattgctg aagagcttgg cggcgaatgg gctgaccgct tcctcgtgct   1380
```

-continued ttacggtatc gccgctcccg attcgcagcg catcgccttc tatcgccttc ttgacgagtt 1440
cttctgagat acattgatga gtttggacaa accacaacta gaatgcagtg aaaaaaatgc 1500
tttatttgtg aaatttgtga tgctattgct ttatttgtaa ccattataag ctgcaataaa 1560
caagttaaca acaacaattg cattcatttt atgtttcggg ttcaggggga ggtgtgggag 1620 gtttttttaaa gcaagtaaaa cctctacaaa tgtggtatgg ctgattatga tc 1672

<210> SEQ ID NO 19
<211> LENGTH: 200
<212> TYPE: DNA
<213> ORGANISM: Artificial sequence
<220> FEATURE:
<223> OTHER INFORMATION: transcription termination sequence from Human beta-Globin

<400> SEQUENCE: 19
gcatagtgtt accatcaacc accttaactt catttttctt attcaatacc taggtaggta 60
gatgctagat tctggaaata aaatatgagt ctcaagtggt ccttgtcctc tctcccagtc 120
aaattctgaa tctagttggc aagattctga aatcaaggca tataatcagt aataagtgat 180
gatagaaggg tatatagaag 200

<210> SEQ ID NO 20
<211> LENGTH: 130
<212> TYPE: DNA
<213> ORGANISM: Artificial sequence
<220> FEATURE:
<223> OTHER INFORMATION: ITR, forward

<400> SEQUENCE: 20
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct 130

<210> SEQ ID NO 21
<211> LENGTH: 1188
<212> TYPE: DNA
<213> ORGANISM: Artificial sequence
<220> FEATURE:
<223> OTHER INFORMATION: Human EF1-alpha Promoter, Exon1, Intron 1, and Exon2 (partial)

<400> SEQUENCE: 21
cgtgaggctc cggtgcccgt cagtgggcag agcgcacatc gcccacagtc cccgagaagt 60
tggggggagg ggtcggcaat tgaaccggtg cctagagaag gtggcgcggg gtaaactggg 120
aaagtgatgt cgtgtactgg ctccgccttt ttcccgaggg tgggggagaa ccgtatataa 180
gtgcagtagt cgccgtgaac gttctttttc gcaacgggtt tgccgccaga acacaggtaa 240
gtgccgtgtg tggttcccgc gggcctggcc tctttacggg ttatggccct tgcgtgcctt 300
gaattacttc cacgcccctg gctgcagtac gtgattcttg atcccgagct tcgggttgga 360
agtgggtggg agagttcgag gccttgcgct taaggagccc cttcgcctcg tgcttgagtt 420
gaggcctggc ctgggcgctg gggccgccgc gtgcgaatct ggtggcacct tcgcgcctgt 480
ctcgctgctt tcgataagtc tctagccatt taaaattttt gatgacctgc tgcgacgctt 540
tttttctggc aagatagtct tgtaaatgcg ggccaagatc tgcacactgg tatttcggtt 600
tttggggccg cgggcggcga cggggcccgt gcgtcccagc gctcatgttc ggcgaggcgg 660

-continued

```
ggcctgcgag cgcggccacc gagaatcgga cgggggtagt ctcaagctgg ccggcctgct    720

ctggtgcctg gcctcgcgcc gccgtgtatc gccccgccct gggcggcaag gctggcccgg    780

tcggcaccag ttgcgtgagc ggaaagatgg ccgcttcccg gccctgctgc agggagctca    840

aaatggagga cgcggcgctc gggagagcgg gcgggtgagt cacccacaca aaggaaaagg    900

gcctttccgt cctcagccgt cgcttcatgt gactccacgg agtaccgggc gccgtccagg    960

cacctcgatt agttctcgag cttttggagt acgtcgtctt taggttgggg ggaggggttt   1020

tatgcgatgg agtttcccca cactgagtgg gtggagactg aagttaggcc agcttggcac   1080

ttgatgtaat tctccttgga atttgccctt tttgagtttg gatcttggtt cattctcaag   1140

cctcagacag tggttcaaag tttttttctt ccatttcagg tgtcgtga                1188
```

```
<210> SEQ ID NO 22
<211> LENGTH: 1434
<212> TYPE: DNA
<213> ORGANISM: Artificial sequence
<220> FEATURE:
<223> OTHER INFORMATION: mCHerry-E2A-Human HPRT fusion gene

<400> SEQUENCE: 22

atggtgagca agggcgagga ggataacatg gccatcatca aggagttcat gcgcttcaag     60

gtgcacatgg agggctccgt gaacggccac gagttcgaga tcgagggcga gggcgagggc    120

cgcccctacg agggcaccca gaccgccaag ctgaaggtga ccaagggtgg cccccctgccc   180

ttcgcctggg acatcctgtc ccctcagttc atgtacggct ccaaggccta cgtgaagcac    240

cccgccgaca tccccgacta cttgaagctg tccttccccg agggcttcaa gtgggagcgc    300

gtgatgaact tcgaggacgg cggcgtggtg accgtgaccc aggactcctc cctgcaggac    360

ggcgagttca tctacaaggt gaagctgcgc ggcaccaact tcccctccga cggccccgta    420

atgcagaaga agaccatggg ctgggaggcc tcctccgagc ggatgtaccc cgaggacggc    480

gccctgaagg gcgagatcaa gcagaggctg aagctgaagg acggcggcca ctacgacgct    540

gaggtcaaga ccacctacaa ggccaagaag cccgtgcagc tgcccggcgc ctacaacgtc    600

aacatcaagt tggacatcac ctcccacaac gaggactaca ccatcgtgga acagtacgaa    660

cgcgccgagg gccgccactc caccggcggc atggacgagc tgtacaaggg aagcggacag    720

tgtactaatt atgctctctt gaaattggct ggagatgttg agagcaaccc tggacctatg    780

gcgacccgca gccctggcgt cgtgattagt gatgatgaac ccggttatga ccttgattta    840

ttttgcatac ctaatcatta tgctgaggat ttggaaaggg tgtttattcc tcatggacta    900

attatggaca ggactgaacg tcttgctcga gatgtgatga aggagatggg aggccatcac    960

attgtagccc tctgtgtgct caagggggc tataaattct ttgctgacct gctggattac   1020

atcaaagcac tgaatagaaa tagtgataga tccattccta tgactgtaga ttttatcaga   1080

ctgaagagct attgtaatga ccagtcaaca ggggacataa aagtaattgg tggagatgat   1140

ctctcaactt taactggaaa gaatgtcttg attgtggaag atataattga cactggcaaa   1200

acaatgcaga ctttgctttc cttggtcagg cagtataatc caaagatggt caaggtcgct   1260

agcttgctgg tgaaaaggac cccacgaagt gttggatata agccagactt tgttggattt   1320

gaaattccag acaagtttgt tgtaggatat gcccttgact ataatgaata cttcagggat   1380

ttgaatcatg tttgtgtcat tagtgaaact ggaaaagcaa aatacaaagc ctaa         1434

<210> SEQ ID NO 23
<211> LENGTH: 272
```

-continued

<212> TYPE: DNA
<213> ORGANISM: Artificial sequence
<220> FEATURE:
<223> OTHER INFORMATION: Poly-adenylation signal from Herpes Simplex
Virus Thymidine Kinase Gene

<400> SEQUENCE: 23
gggggaggct aactgaaaca cggaaggaga caataccgga aggaacccgc gctatgacgg 60
caataaaaag acagaataaa acgcacggtg ttgggtcgtt tgttcataaa cgcggggttc 120
ggtcccaggg ctggcactct gtcgataccc caccgagacc ccattggggc caatacgccc 180
gcgtttcttc cttttcccca ccccaccccc caagttcggg tgaaggccca gggctcgcag 240
ccaacgtcgg ggcggcaggc cctgccatag cc 272

<210> SEQ ID NO 24
<211> LENGTH: 1031
<212> TYPE: DNA
<213> ORGANISM: Artificial sequence
<220> FEATURE:
<223> OTHER INFORMATION: Human anti-repressor element 40 (AY190756.1)

<400> SEQUENCE: 24
gatcaagaaa gcactccggg ctccagaagg agccttccag gccagctttg agcataagct 60
gctgatgagc agtgagtgtc ttgagtagtg ttcagggcag catgttacca ttcatgcttg 120
acttctagcc agtgtgacga gaggctggag tcaggtctct agagagttga gcagctccag 180
ccttagatct cccagtctta tgcggtgtgc ccattcgctt tgtgtctgca gtcccctggc 240
cacacccagt aacagttctg ggatctatgg gagtagcttc cttagtgagc tttcccttca 300
aatactttgc aaccaggtag agaagtttgg agtgaaggtt ttgttcttcg tttcttcaca 360
atatggatat gcatcttctt ttgaaaatgt taaagtaaat tacctctctt ttcagatact 420
gtcttcatgc gaacttggta tcctgtttcc atcccagcct tctataaccc agtaacatct 480
tttttgaaac cagtgggtga gaaagacacc tggtcaggaa cgcggaccac aggacaactc 540
aggctcaccc acggcatcag actaaaggca aacaaggact ctgtataaag taccggtggc 600
atgtgtatta gtggagatgc agcctgtgct ctgcagacag ggagtcacac agacactttt 660
ctataatttc ttaagtgctt tgaatgttca agtagaaagt ctaacattaa atttgattga 720
acaattgtat attcatggaa tattttggaa cggaatacca aaaaatggca atagtggttc 780
tttctggatg gaagacaaac ttttcttctt taaaataaat tttattttat atatttgagg 840
ttgaccacat gaccttaagg atacatatag acagtaaact ggttactaca gtgaagcaaa 900
ttaacatatc taccatcgta catagttaca tttttttgtg tgacaggaac agctaaaatc 960
tacgtattta acaaaactcc taaagacaat acatttttat taactatagc cctcatgatg 1020
tacattagat c 1031

<210> SEQ ID NO 25
<211> LENGTH: 354
<212> TYPE: DNA
<213> ORGANISM: Artificial sequence
<220> FEATURE:
<223> OTHER INFORMATION: Mouse anti-repressor element 40

<400> SEQUENCE: 25
acttgaattt tcaagtataa agtctagtgc taaatttaat ttgaacaact gtatagtttt 60
tgctggttgg gggaaggaaa aaaaatggtg gcagtgtttt tttcagaatt agaagtgaaa 120
tgaaaacttg ttgtgtgtga ggatttctaa tgccatgtgg tggttgcata ctgagtgaag 180
ccggtgagca ttctgccatg tcacccctc gtgctcagta atgtacttta cagaaatcct 240
aaactcaaaa gattgatata aaccatgctt cttgtgtata tccggtctct tctctgggta 300
gtctcactca gcctgcattt ctgccatccc ttgtcctctg gcccccgtcg ccca 354

<210> SEQ ID NO 26
<211> LENGTH: 222
<212> TYPE: DNA
<213> ORGANISM: Artificial sequence
<220> FEATURE:
<223> OTHER INFORMATION: Herpes Virus Thymidine Kinase Gene Promoter

<400> SEQUENCE: 26
ttcagggagt ggcgcagctg cttcatcccc gtggcccgtt gctcgcgttt gctggcggtg 60
tccccggaag aaatatattt gcatgtcttt agttctatga tgacacaaac cccgcccagc 120
gtcttgtcat tggcgaaaac acgcagatgc agtcggggcg gcgcggtccc aggtccactt 180
cgcatattaa ggtgacgcgt gtggcctcga acacagagcg ac 222

<210> SEQ ID NO 27
<211> LENGTH: 600
<212> TYPE: DNA
<213> ORGANISM: Artificial sequence
<220> FEATURE:
<223> OTHER INFORMATION: Puromycin N-acetyl transferase coding region

<400> SEQUENCE: 27
atgaccgagt acaagcccac ggtgcgcctc gccacccgcg acgacgtccc ccgggccgta 60
cgcaccctcg ccgccgcgtt cgccgactac cccgccacgc gccacaccgt tgacccggac 120
cgccacatcg agcgggtcac cgagctgcaa gaactcttcc tcacgcgcgt cgggctcgac 180
atcggcaagg tgtgggtcgc ggacgacggc gccgcggtgg cggtctggac cacgccggag 240
agcgtcgaag cgggggcggt gttcgccgag atcggcccgc gcatggccga gttgagcggt 300
tcccggctgg ccgcgcagca acagatggaa ggcctcctgg cgccgcaccg gcccaaggag 360
cccgcgtggt tcctggccac cgtcggcgtc tcgcccgacc accagggcaa gggtctgggc 420
agcgccgtcg tgctccccgg agtggaggcg gccgagcgcg ccggggtgcc cgccttcctg 480
gagacctccg cgccccgcaa cctccccttc tacgagcggc tcggcttcac cgtcaccgcc 540
gacgtcgagg tgcccgaagg accgcgcacc tggtgcatga cccgcaagcc cggtgcctga 600

<210> SEQ ID NO 28
<211> LENGTH: 224
<212> TYPE: DNA
<213> ORGANISM: Artificial sequence
<220> FEATURE:
<223> OTHER INFORMATION: Polyadenylation Signal from Bovine Growth
      Hormone Gene

<400> SEQUENCE: 28
tgtgccttct agttgccagc catctgttgt ttgcccctcc cccgtgcctt ccttgaccct 60
ggaaggtgcc actcccactg tcctttccta ataaaatgag gaaattgcat cgcattgtct 120
gagtaggtgt cattctattc tggggggtgg ggtggggcag gacagcaagg gggaggattg 180
ggaagacaat agcaggcatg ctggggatgc ggtgggctct atgg 224

<210> SEQ ID NO 29
<211> LENGTH: 490
<212> TYPE: DNA
<213> ORGANISM: Artificial sequence
<220> FEATURE:
<223> OTHER INFORMATION: Epstein Barr Virus OriP Replication Element

<400> SEQUENCE: 29

```
ccccttatt aaccctaaac gggtagcata tgcttcccgg gtagtagtat atactatcca     60

gactaaccct aattcaatag catatgttac ccaacgggaa gcatatgcta tcgaattagg    120

gttagtaaaa gggtcctaag gaacagcgat ctggatagca tatgctatcc taatctatat    180

ctgggtagca tatgctatcc taatctatat ctgggtagca taggctatcc taatctatat    240

ctgggtagca tatgctatcc taatctatat ctgggtagta tatgctatcc taatttatat    300

ctgggtagca taggctatcc taatctatat ctgggtagca tatgctatcc taatctatat    360

ctgggtagta tatgctatcc taatctgtat ccgggtagca tatgctatcc tcatgcatat    420

acagtcagca tatgataccc agtagtagag tgggagtgct atcctttgca tatgccgcca    480

cctcccaagg                                                           490
```

<210> SEQ ID NO 30
<211> LENGTH: 1815
<212> TYPE: DNA
<213> ORGANISM: Artificial sequence
<220> FEATURE:
<223> OTHER INFORMATION: pUC57 vector sequences encoding plasmid
      replication origin and ampicillin resistance gene

<400> SEQUENCE: 30

```
cgtcaggtgg cacttttcgg ggaaatgtgc gcggaacccc tatttgttta tttttctaaa     60

tacattcaaa tatgtatccg ctcatgagac aataaccctg ataaatgctt caataatatt    120

gaaaaaggaa gagtatgagt attcaacatt tccgtgtcgc ccttattccc ttttttgcgg    180

cattttgcct tcctgttttt gctcacccag aaacgctggt gaaagtaaaa gatgctgaag    240

atcagttggg tgcacgagtg ggttacatcg aactggatct caacagcggt aagatccttg    300

agagttttcg ccccgaagaa cgttttccaa tgatgagcac ttttaaagtt ctgctatgtg    360

gcgcggtatt atcccgtatt gacgccgggc aagagcaact cggtcgccgc atacactatt    420

ctcagaatga cttggttgag tactcaccag tcacagaaaa gcatcttacg gatggcatga    480

cagtaagaga attatgcagt gctgccataa ccatgagtga taacactgcg gccaacttac    540

ttctgacaac gatcggagga ccgaaggagc taaccgcttt tttgcacaac atgggggatc    600

atgtaactcg ccttgatcgt tgggaaccgg agctgaatga agccatacca aacgacgagc    660

gtgacaccac gatgcctgta gcaatggcaa caacgttgcg caaactatta actggcgaac    720

tacttactct agcttcccgg caacaattaa tagactggat ggaggcggat aaagttgcag    780

gaccacttct gcgctcggcc cttccggctg gctggtttat tgctgataaa tctggagccg    840

gtgagcgtgg gtctcgcggt atcattgcag cactggggcc agatggtaag ccctcccgta    900

tcgtagttat ctacacgacg gggagtcagg caactatgga tgaacgaaat agacagatcg    960

ctgagatagg tgcctcactg attaagcatt ggtaactgtc agaccaagtt tactcatata   1020

tactttagat tgatttaaaa cttcattttt aatttaaaag gatctaggtg aagatccttt   1080

ttgataatct catgaccaaa atcccttaac gtgagttttc gttccactga gcgtcagacc   1140

ccgtagaaaa gatcaaagga tcttcttgag atcctttttt tctgcgcgta atctgctgct   1200

tgcaaacaaa aaaaccaccg ctaccagcgg tggtttgttt gccggatcaa gagctaccaa   1260

ctctttttcc gaaggtaact ggcttcagca gagcgcagat accaaatact gttcttctag   1320

tgtagccgta gttaggccac cacttcaaga actctgtagc accgcctaca tacctcgctc   1380
```

tgctaatcct gttaccagtg gctgctgcca gtggcgataa gtcgtgtctt accgggttgg 1440
actcaagacg atagttaccg gataaggcgc agcggtcggg ctgaacgggg ggttcgtgca 1500
cacagcccag cttggagcga acgacctaca ccgaactgag atacctacag cgtgagctat 1560
gagaaagcgc cacgcttccc gaagggagaa aggcggacag gtatccggta agcggcaggg 1620
tcggaacagg agagcgcacg agggagcttc caggggggaaa cgcctggtat ctttatagtc 1680
ctgtcgggtt tcgccacctc tgacttgagc gtcgattttt gtgatgctcg tcaggggggc 1740
ggagcctatg gaaaaacgcc agcaacgcgg cctttttacg gttcctggcc ttttgctggc 1800
cttttgctca catgt 1815

<210> SEQ ID NO 31
<211> LENGTH: 7671
<212> TYPE: DNA
<213> ORGANISM: Artificial sequence
<220> FEATURE:
<223> OTHER INFORMATION: P321 Plasmid for Generating Recombinant Adenovirus expressing SR21 Recombinase

<400> SEQUENCE: 31
ttaattaacc gcaattctca tgtttgacag cttatcatca tcaataatat accttatttt 60
ggattgaagc caatatgata atgagggggt ggagtttgtg acgtggcgcg gggcgtggga 120
acggggcggg tgacgtagta gtgtggcgga agtgtgatgt tgcaagtgtg gcggaacaca 180
tgtaagcgac ggatgtggca aaagtgacgt ttttggtgtg cgccggtgta cacaggaagt 240
gacaattttc gcgcggtttt aggcggatgt tgtagtaaat ttgggcgtaa ccgagtaaga 300
tttggccatt ttcgcgggaa aactgaataa gaggaagtga aatctgaata attttgtgtt 360
actcatagcg cgtaatattt gtctagggcc gcggggactt tgaccgttta cgtggagact 420
cgcccaggtg tttttctcag gtgttttccg cgttccgggt caaagttggc gttttattat 480
tatagtcagt acgtaccagt gcactggcct aggctctctt aaggtagctc gaggagcttg 540
gcccattgca tacgttgtat ccatatcata atatgtacat ttatattggc tcatgtccaa 600
cattaccgcc atgttgacat tgattattga ctagttatta atagtaatca attacggggt 660
cattagttca tagcccatat atggagttcc gcgttacata acttacggta aatggcccgc 720
ctggctgacc gcccaacgac ccccgcccat tgacgtcaat aatgacgtat gttcccatag 780
taacgccaat agggactttc cattgacgtc aatgggtgga gtatttacgg taaactgccc 840
acttggcagt acatcaagtg tatcatatgc caagtacgcc ccctattgac gtcaatgacg 900
gtaaatggcc cgcctggcat tatgcccagt acatgacctt atgggacttt cctacttggc 960
agtacatcta cgtattagtc atcgctatta ccatggtgat gcggttttgg cagtacatca 1020
atgggcgtgg atagcggttt gactcacggg gatttccaag tctccacccc attgacgtca 1080
atgggagttt gttttggcac caaaatcaac gggactttcc aaaatgtcgt aacaactccg 1140
ccccattgac gcaaatgggc ggtaggcgtg tacggtggga ggtctatata agcagagctc 1200
gtttagtgaa ccgtcggcgc gccgccacca tggaattaaa acacattgtc aattcctata 1260
atgtgactaa aattattggc tatttgagac gttccagaca agatgttgaa agagagaagc 1320
gtactggtga agatactttg acagaacaaa aagaacttat gaataaaata ttgactggga 1380
ttgaaatacc gtacgaaaca agaactgaga tcggttctgg tgaaagcatt gaaggaagac 1440
cagtgtttaa aagttgctta gctgatctga ggtctggaaa atttcaagca attgctgtaa 1500
aagaaataac tcgtcttagt cgtggtagtt acagtgatgc tggtgaaatc gtcaatcttc 1560

-continued taaatgaaaa aaggattatc ataattacac catataaaat atatgatcca agaaatcctg 1620
ttgatgctcg tcaaattaga tttgagctat ttatggctag agaagaattt gaaatgacaa 1680
gagaaagaat gaatggtgcc aagtttactt atgctgcaca aggaaaatgg atttctggtt 1740
tagcaccatt tggctataaa ttaaataagc gtacatctcg cctcgaacca tcggatgaag 1800
acaaagttgt ggtaaagttg atatttgaca ttttcttaaa tggccttgat ggtaaagatt 1860
taagttatac agctattgca actcatcttt ctaaacttca attcactacc ccaaggggag 1920
gaaaaagatg gagtaaggac actgttagaa aaattcttca aaatgaagcc tatatgggaa 1980
gggttaggta taaagcaaga gaaaccacaa aagatggaaa aaaagtcttc cgacctgaaa 2040
gtgaacatat tgttgtagat gatgcccacg aaccaataat aaataaagag gactttgaag 2100
ctgttcaaga aaagattaaa aataaagtgc ctctgcttcc agtcgtaaca tcttatgaac 2160
ctaatgaatt agcgggaata tgtgtatgct ctgtctgtgg aaaatcactt caaaaatttg 2220
aatccgaata caataggaaa aacaaagatg ggacttccag ctattttcac gtgaagttat 2280
tgatttgcaa aatcaacaag tgcacatcag tgagatatga gtatgttgaa gaagcaattt 2340
tggagtatct tgagcagttg attgctttag aaaataataa actaaaggct ataattgaaa 2400
aatctatgga agcagcagaa actaacaatt cagaaaagac aagtgagcaa atgctagtac 2460
aagcaaacca aaaacagaaa gaactcgaaa acaaattgac atttattttt gaaaaatttg 2520
aatctggaat ttatacagat gaaatgtttt tgcaaaggaa agcagctatt gaaaaagaag 2580
tagctgacat taaaaaattg aaacaagaac ttagcatgac atttgaagtt aaagagaaag 2640
atgttaatga atttagggtt aacatatcag atgtagttaa attttataaa gaatctaaaa 2700
gtagaggatt aaaaaatgaa aagttgagat ccatttttga ctttatagta ttagaaatga 2760
cagagaaaag acgaggcccc atccctgcta agttcaatat ttatccggtt ttgcgaatcc 2820
cgagtgtagt taattagtct agagatacat tgatgagttt ggacaaacca caactagaat 2880
gcagtgaaaa aaatgcttta tttgtgaaat ttgtgatgct attgctttat ttgtaaccat 2940
tataagctgc aataaacaag ttaacaacaa caattgcatt cattttatgt ttcaggttca 3000
gggggaggtg tgggaggttt tttaaagcaa gtaaaacctc tacaaatgtg gtatggctga 3060
ttatgatcgc ggccgcctag atctgtactg aaatgtgtgg gcgtggctta agggtgggaa 3120
agaatatata aggtgggggt cttatgtagt tttgtatctg ttttgcagca gccgccgccg 3180
ccatgagcac caactcgttt gatggaagca ttgtgagctc atatttgaca acgcgcatgc 3240
ccccatgggc cggggtgcgt cagaatgtga tgggctccag cattgatggt cgccccgtcc 3300
tgcccgcaaa ctctactacc ttgacctacg agaccgtgtc tggaacgccg ttggagactg 3360
cagcctccgc cgccgcttca gccgctgcag ccaccgcccg cgggattgtg actgactttg 3420
ctttcctgag cccgcttgca agcagtgcag cttcccgttc atccgcccgc gatgacaagt 3480
tgacggctct tttggcacaa ttggattctt tgacccggga acttaatgtc gtttctcagc 3540
agctgttgga tctgcgccag caggtttctg ccctgaaggc ttcctcccct cccaatgcgg 3600
tttaaaacat aaataaaaaa ccagactctg tttggatttg gatcaagcaa gtgtcttgct 3660
gtctttattt aggggttttg cgcgcgcggt aggcccggga ccagcggtct cggtcgttga 3720
gggtcctgtg tatttttttcc aggacgtggt aaaggtgact ctggatgttc agatacatgg 3780
gcataagccc gtctctgggg tggaggtagc accactgcag agcttcatgc tgcggggtgg 3840
tgttgtagat gatccagtcg tagcaggagc gctgggcgtg gtgcctaaaa atgtctttca 3900

-continued gtagcaagct gattgccagg ggcaggccct tggtgtaagt gtttacaaag cggttaagct 3960
gggatgggtg catacgtggg gatatgagat gcatcttgga ctgtattttt aggttggcta 4020
tgttcccagc catatccctc cggggattca tgttgtgcag aaccaccagc acagtgtatc 4080
cggtgcactt gggaaatttg tcatgtagct tagaaggaaa tgcgtggaag aacttggaga 4140
cgcccttgtg acctccaaga ttttccatgc attcgtccat aatgatggca atgggcccac 4200
gggcggcggc ctgggcgaag atatttctgg gatcactaac gtcatagttg tgttccagga 4260
tgagatcgtc ataggccatt tttacaaagc gcgggcggag ggtgccagac tgcggtataa 4320
tggttccatc cggcccaggg gcgtagttac cctcacagat ttgcatttcc cacgctttga 4380
gttcagatgg ggggatcatg tctacctgcg gggcgatgaa gaaaacggtt tccggggtag 4440
gggagatcag ctgggaagaa agcaggttcc tgagcagctg cgacttaccg cagccggtgg 4500
gcccgtaaat cacacctatt accggctgca actggtagtt aagagagctg cagctgccgt 4560
catccctgag caggggggcc acttcgttaa gcatgtccct gactcgcatg ttttccctga 4620
ccaaatccgc cagaaggcgc tcgccgccca gcgatagcag ttcttgcaag gaagcaaagt 4680
ttttcaacgg tttgagaccg tccgccgtag gcatgctttt gagcgtttga ccaagcagtt 4740
ccaggcggtc ccacagctcg gtcacctgct ctacggcatc tcgatccagc atatctcctc 4800
gtttcgcggg ttggggcggc tttcgctgta cggcagtagt cggtgctcgt ccagacgggc 4860
cagggtcatg tctttccacg ggcgcagggt cctcgtcagc gtagtctggg tcacggtgaa 4920
ggggtgcgct ccgggctgcg cgctggccag ggtgcgcttg aggctggtcc tgctggtgct 4980
gaagcgctgc cggtcttcgc cctgcgcgtc ggccaggtag catttgacca tggtgtcata 5040
gtccagcccc tccgcggcgt ggcccttggc gcgcagcttg cccttggagg aggcgccgca 5100
cgaggggcag tgcagacttt tgagggcgta gagcttgggc gcgagaaata ccgattccgg 5160
ggagtaggca tccgcgccgc aggccccgca gacggtctcg cattccacga gccaggtgag 5220
ctctggccgt tcggggtcaa aaaccaggtt tcccccatgc tttttgatgc gtttcttacc 5280
tctggtttcc atgagccggt gtccacgctc ggtgacgaaa aggctgtccg tgtccccgta 5340
tacagacttg agaggcctgt cctcgagcgg tgttccgcgg tcctcctcgt atagaaactc 5400
ggaccactct gagacaaagg ctcgcgtcca ggccagcacg aaggaggcta agtgggaggg 5460
gtagcggtcg ttgtccacta gggggtccac tcgctccagg gtgtgaagac acatgtcgcc 5520
ctcttcggca tcaaggaagg tgattggttt gtaggtgtag gccacgtgac cgggtgttcc 5580
tgaagggggg ctataaaagg gggtgggggc gcgttcgtcc tcactctctt ccgcatcgct 5640
gtctgcgagg gccagctgtt ggggtgagtc gacgcgaggc tggatggcct tccccattat 5700
gattcttctc gcttccggcg gcatcgggat gcccgcgttg caggccatgc tgtccaggca 5760
ggtagatgac gaccatcagg gacagcttca aggccagcaa aaggccagga accgtaaaaa 5820
ggccgcgttg ctggcgtttt tccataggct ccgcccccct gacgagcatc acaaaaatcg 5880
acgctcaagt cagaggtggc gaaacccgac aggactataa agataccagg cgtttccccc 5940
tggaagctcc ctcgtgcgct ctcctgttcc gaccctgccg cttaccggat acctgtccgc 6000
ctttctccct tcgggaagcg tggcgctttc tcatagctca cgctgtaggt atctcagttc 6060
ggtgtaggtc gttcgctcca agctgggctg tgtgcacgaa ccccccgttc agcccgaccg 6120
ctgcgcctta tccggtaact atcgtcttga gtccaacccg gtaagacacg acttatcgcc 6180
actggcagca gccactggta acaggattag cagagcgagg tatgtaggcg gtgctacaga 6240
gttcttgaag tggtggccta actacggcta cactagaagg acagtatttg gtatctgcgc 6300
tctgctgaag ccagttacct tcggaaaaag agttggtagc tcttgatccg gcaaacaaac 6360
caccgctggt agcggtggtt tttttgtttg caagcagcag attacgcgca gaaaaaaagg 6420
atctcaagaa gatcctttga tcttttctac ggggtctgac gctcagtgga acgaaaactc 6480
acgttaaggg attttggtca tgagattatc aaaaaggatc ttcacctaga tccttttaaa 6540
ttaaaaatga agttttaaat caatctaaag tatatatgag taaacttggt ctgacagtta 6600
ccaatgctta atcagtgagg cacctatctc agcgatctgt ctatttcgtt catccatagt 6660
tgcctgactc cccgtcgtgt agataactac gatacgggag ggcttaccat ctggccccag 6720
tgctgcaatg ataccgcgag acccacgctc accggctcca gatttatcag caataaacca 6780
gccagccgga agggccgagc gcagaagtgg tcctgcaact ttatccgcct ccatccagtc 6840
tattaattgt tgccgggaag ctagagtaag tagttcgcca gttaatagtt tgcgcaacgt 6900
tgttgccatt gctgcaggca tcgtggtgtc acgctcgtcg tttggtatgg cttcattcag 6960
ctccggttcc caacgatcaa ggcgagttac atgatccccc atgttgtgca aaaaagcggt 7020
tagctccttc ggtcctccga tcgttgtcag aagtaagttg gccgcagtgt tatcactcat 7080
ggttatggca gcactgcata attctcttac tgtcatgcca tccgtaagat gcttttctgt 7140
gactggtgag tactcaacca agtcattctg agaatagtgt atgcggcgac cgagttgctc 7200
ttgcccggcg tcaacacggg ataataccgc gccacatagc agaactttaa aagtgctcat 7260
cattggaaaa cgttcttcgg ggcgaaaact ctcaaggatc ttaccgctgt tgagatccag 7320
ttcgatgtaa cccactcgtg cacccaactg atcttcagca tcttttactt tcaccagcgt 7380
ttctgggtga gcaaaaacag gaaggcaaaa tgccgcaaaa aagggaataa gggcgacacg 7440
gaaatgttga atactcatac tcttcctttt tcaatattat tgaagcattt atcagggtta 7500
ttgtctcatg agcggataca tatttgaatg tatttagaaa aataaacaaa taggggttcc 7560
gcgcacattt ccccgaaaag tgccacctga cgtctaagaa accattatta tcatgacatt 7620
aacctataaa aataggcgta tcacgaggcc ctttcgtctt caagaattgt t 7671

<210> SEQ ID NO 32
<211> LENGTH: 20
<212> TYPE: DNA
<213> ORGANISM: Artificial sequence
<220> FEATURE:
<223> OTHER INFORMATION: Primer P349F3

<400> SEQUENCE: 32
cgtaaacggt tggtggcgca 20

<210> SEQ ID NO 33
<211> LENGTH: 24
<212> TYPE: DNA
<213> ORGANISM: Artificial sequence
<220> FEATURE:
<223> OTHER INFORMATION: Primer P349R9

<400> SEQUENCE: 33
gtagaagggc acagtgtggg ctat 24

<210> SEQ ID NO 34
<211> LENGTH: 606
<212> TYPE: DNA
<213> ORGANISM: Artificial sequence
<220> FEATURE:
<223> OTHER INFORMATION: Sequence containing SEQ ID NO:14 Upstream half
of beta-Actin Intron and SEQ ID NO:15 Downstream half of

```
      beta-Actin intron
<220> FEATURE:
<221> NAME/KEY: misc_feature
<222> LOCATION: (144)..(178)
<223> OTHER INFORMATION: SEQ ID NO:14 Upstream half of beta-Actin Intron
<220> FEATURE:
<221> NAME/KEY: misc_feature
<222> LOCATION: (237)..(312)
<223> OTHER INFORMATION: SEQ ID NO:15 Downstream half of beta-Actin
      Intron

<400> SEQUENCE: 34

cgcagacgca ggagcagaac aaagagaatc agaatcccaa ttctgatgcg ccggtgatca     60

gatcaaaaac ttcagccagg tacatggagc tggtcgggtg gctcgtggac aaggggatta    120

cctcggagaa gcagtggatc caggtgggtg tctttcctgc ctgagctgac ctgggcagac    180

gcgtaattaa gtatcatgat aaactgacaa agcggtttct ccaacgaatt atcgattcgg    240

ctgtggggtc ctgtggtgtg tggggagctg tcacatccag ggtcctcact gcctgtcccc    300

ttccctcctc aggaggacca ggcctcatac atctccttca atgcggcctc caactcgcgg    360

tcccaaatta aggctgcctt ggacaatgcg ggaaagatta tgagcctgac taaaaccgcc    420

cccgactacc tggtgggcca gcagcccgtg gaggacattt ccagcaatcg gatttataaa    480

attttggaac taaacgggta cgatccccaa tatgcggctt ccgtctttct gggatgggcc    540

acgaaaaagt tcggcaagag gaacaccatc tggctgtttg ggcctgcaac taccgggaag    600

accaac                                                               606


<210> SEQ ID NO 35
<211> LENGTH: 45
<212> TYPE: DNA
<213> ORGANISM: Artificial sequence
<220> FEATURE:
<223> OTHER INFORMATION: AttL Recombined sequence

<400> SEQUENCE: 35

aattaagtat catgataaac tgacaaagcg gtttctccaa cgaat                     45


<210> SEQ ID NO 36
<211> LENGTH: 21
<212> TYPE: DNA
<213> ORGANISM: Artificial sequence
<220> FEATURE:
<223> OTHER INFORMATION: mCherry Primer 1

<400> SEQUENCE: 36

ctgttccacg atggtgtagt c                                               21


<210> SEQ ID NO 37
<211> LENGTH: 20
<212> TYPE: DNA
<213> ORGANISM: Artificial sequence
<220> FEATURE:
<223> OTHER INFORMATION: mCherry Primer 2

<400> SEQUENCE: 37

tgaggtcaag accacctaca                                                 20


<210> SEQ ID NO 38
<211> LENGTH: 24
<212> TYPE: DNA
<213> ORGANISM: Artificial sequence
<220> FEATURE:
<223> OTHER INFORMATION: mCherry Probe, FAM at 5' end, ZEN between bases
      9 and 10, 3IABkFQ at 3' end
```

<400> SEQUENCE: 38
ttggacatca cctcccacaa cgag 24

<210> SEQ ID NO 39
<211> LENGTH: 22
<212> TYPE: DNA
<213> ORGANISM: Artificial sequence
<220> FEATURE:
<223> OTHER INFORMATION: Adenovirus Exon 2 (Ad5E2) Primer 1

<400> SEQUENCE: 39
gggtgatgca gtagaaggta ag 22

<210> SEQ ID NO 40
<211> LENGTH: 19
<212> TYPE: DNA
<213> ORGANISM: Artificial sequence
<220> FEATURE:
<223> OTHER INFORMATION: Adenovirus Exon 2 (Ad5E2) Primer 2

<400> SEQUENCE: 40
atgaagttcg gcggagatg 19

<210> SEQ ID NO 41
<211> LENGTH: 22
<212> TYPE: DNA
<213> ORGANISM: Artificial sequence
<220> FEATURE:
<223> OTHER INFORMATION: Adenovirus Exon 2 (Ad5E2) Probe, HEX at 5' end, Zen between bases 9 and 10, 3IABkFQ at 3' end

<400> SEQUENCE: 41
tcttgttccc agcggtccca tc 22

<210> SEQ ID NO 42
<211> LENGTH: 20
<212> TYPE: DNA
<213> ORGANISM: Artificial sequence
<220> FEATURE:
<223> OTHER INFORMATION: P5 (P5 Promoter region of AAV) Primer 1

<400> SEQUENCE: 42
gtggtcacgc tgggtattta 20

<210> SEQ ID NO 43
<211> LENGTH: 22
<212> TYPE: DNA
<213> ORGANISM: Artificial sequence
<220> FEATURE:
<223> OTHER INFORMATION: P5 (P5 Promoter region of AAV) Primer 2

<400> SEQUENCE: 43
gggaccttaa tcacaatctc gt 22

<210> SEQ ID NO 44
<211> LENGTH: 23
<212> TYPE: DNA
<213> ORGANISM: Artificial sequence
<220> FEATURE:
<223> OTHER INFORMATION: P5 (P5 Promoter region of AAV) Probe, FAM at 5' end, ZEN between bases 9 and 10, 31ABkFQ at 3' end

<400> SEQUENCE: 44
tttgaagcgg gaggtttgaa cgc 23

<210> SEQ ID NO 45
<211> LENGTH: 22
<212> TYPE: DNA
<213> ORGANISM: Artificial sequence
<220> FEATURE:
<223> OTHER INFORMATION: AAV REP Gene Primer 1

<400> SEQUENCE: 45
gtccgtgagt gaagcagata tt 22

<210> SEQ ID NO 46
<211> LENGTH: 21
<212> TYPE: DNA
<213> ORGANISM: Artificial sequence
<220> FEATURE:
<223> OTHER INFORMATION: AAV REP Gene Primer 2

<400> SEQUENCE: 46
ttcgatcaac tacgcagaca g 21

<210> SEQ ID NO 47
<211> LENGTH: 24
<212> TYPE: DNA
<213> ORGANISM: Artificial sequence
<220> FEATURE:
<223> OTHER INFORMATION: AAV REP Gene Probe, FAM at 5' end, ZEN between bases 9 and 10, 3IABkFQ at 3' end

<400> SEQUENCE: 47
tctgatgctg tttccctgca gaca 24

<210> SEQ ID NO 48
<211> LENGTH: 21
<212> TYPE: DNA
<213> ORGANISM: Artificial sequence
<220> FEATURE:
<223> OTHER INFORMATION: AAV9 CAP Gene Primer 1

<400> SEQUENCE: 48
ccgggtccaa ggtatttgta a 21

<210> SEQ ID NO 49
<211> LENGTH: 21
<212> TYPE: DNA
<213> ORGANISM: Artificial sequence
<220> FEATURE:
<223> OTHER INFORMATION: AAV9 CAP Gene Primer 2

<400> SEQUENCE: 49
ctcaacccaa ggcaaatcaa c 21

<210> SEQ ID NO 50
<211> LENGTH: 24
<212> TYPE: DNA
<213> ORGANISM: Artificial sequence
<220> FEATURE:
<223> OTHER INFORMATION: AAV9 CAP Gene Probe, FAM at 5' end, ZEN between bases 9 and 10, 3IABkFQ at 3' end

<400> SEQUENCE: 50
acatcaagac aacgctcgag gtct 24

<210> SEQ ID NO 51
<211> LENGTH: 21
<212> TYPE: DNA
<213> ORGANISM: Artificial sequence
<220> FEATURE:
<223> OTHER INFORMATION: Beta lactamase (Ampicillin resistance) gene
Primer 1

<400> SEQUENCE: 51
ccagaaacgc tggtgaaagt a 21

<210> SEQ ID NO 52
<211> LENGTH: 22
<212> TYPE: DNA
<213> ORGANISM: Artificial sequence
<220> FEATURE:
<223> OTHER INFORMATION: Beta lactamase (Ampicillin resistance) gene
Primer 2

<400> SEQUENCE: 52
ctcaaggatc ttaccgctgt tg 22

<210> SEQ ID NO 53
<211> LENGTH: 24
<212> TYPE: DNA
<213> ORGANISM: Artificial sequence
<220> FEATURE:
<223> OTHER INFORMATION: Beta lactamase (Ampicillin resistance) gene
Probe, FAM at 5' end, ZEN between bases 9 and 10, 3IABkFQ at 3'
end

<400> SEQUENCE: 53
tgcacgagtg ggttacatcg aact 24

<210> SEQ ID NO 54
<211> LENGTH: 14
<212> TYPE: DNA
<213> ORGANISM: Artificial sequence
<220> FEATURE:
<223> OTHER INFORMATION: Bacillus safensis strain CCMA-560

<400> SEQUENCE: 54
actgacaaag cggt 14

<210> SEQ ID NO 55
<211> LENGTH: 863
<212> TYPE: DNA
<213> ORGANISM: Artificial sequence
<220> FEATURE:
<223> OTHER INFORMATION: 5' portion of the AAV2 rep gene upstream of the
stop cassette in the exemplified construct

<400> SEQUENCE: 55
ggtcctgtat tagaggtcac gtgagtgttt tgcgacattt tgcgacacca tgtggtcacg 60
ctgggtattt aagcccgagt gagcacgcag ggtctccatt ttgaagcggg aggtttgaac 120
gcgcagccgc catgccgggg ttttacgaga ttgtgattaa ggtccccagc gaccttgacg 180
agcatctgcc cggcatttct gacagctttg tgaactgggt ggccgagaag gaatgggagt 240
tgccgccaga ttctgacatg gatctgaatc tgattgagca ggcacccctg accgtggccg 300
agaagctgca gcgcgacttt ctgacggaat ggcgccgtgt gagtaaggcc ccggaggccc 360
ttttctttgt gcaatttgag aagggagaga gctacttcca catgcacgtg ctcgtggaaa 420
ccaccggggt gaaatccatg gttttgggac gtttcctgag tcagattcgc gaaaaactga 480
ttcagagaat ttaccgcggg atcgagccga ctttgccaaa ctggttcgcg gtcacaaaga 540
ccagaaatgg cgccggaggc gggaacaagg tggtggatga gtgctacatc cccaattact 600
tgctccccaa aacccagcct gagctccagt gggcgtggac taatatggaa cagtatttaa 660
gcgcctgttt gaatctcacg gagcgtaaac ggttggtggc gcagcatctg acgcacgtgt 720
cgcagacgca ggagcagaac aaagagaatc agaatcccaa ttctgatgcg ccggtgatca 780
gatcaaaaac ttcagccagg tacatggagc tggtcgggtg gctcgtggac aaggggatta 840
cctcggagaa gcagtggatc cag 863

<210> SEQ ID NO 56
<211> LENGTH: 1150
<212> TYPE: DNA
<213> ORGANISM: Artificial sequence
<220> FEATURE:
<223> OTHER INFORMATION: 3' portion of the AAV2 rep gene downstream of the stop cassette in the exemplified construct

<400> SEQUENCE: 56
gaggaccagg cctcatacat ctccttcaat gcggcctcca actcgcggtc ccaaattaag 60
gctgccttgg acaatgcggg aaagattatg agcctgacta aaaccgcccc cgactacctg 120
gtgggccagc agcccgtgga ggacatttcc agcaatcgga tttataaaat tttggaacta 180
aacgggtacg atccccaata tgcggcttcc gtctttctgg gatgggccac gaaaaagttc 240
ggcaagagga acaccatctg gctgtttggg cctgcaacta ccgggaagac caacatcgcg 300
gaggccatag cccacactgt gcccttctac gggtgcgtaa actggaccaa tgagaacttt 360
cccttcaacg actgtgtcga caagatggtg atctggtggg aggaggggaa gatgaccgcc 420
aaggtcgtgg agtcggccaa agccattctc ggaggaagca aggtgcgcgt ggaccagaaa 480
tgcaagtcct cggcccagat agacccgact cccgtgatcg tcacctccaa caccaacatg 540
tgcgccgtga ttgacgggaa ctcaacgacc ttcgaacacc agcagccgtt gcaagaccgg 600
atgttcaaat ttgaactcac ccgccgtctg gatcatgact ttgggaaggt caccaagcag 660
gaagtcaaag actttttccg gtgggcaaag gatcacgtgg ttgaggtgga gcatgagttc 720
tacgtcaaaa agggtggagc caagaaaaga cccgccccca gtgacgcaga tataagtgag 780
cccaaacggg tgcgcgagtc agttgcgcag ccatcgacgt cagacgcgga agcttcgatc 840
aactacgcag acaggtacca aaacaaatgt tctcgtcacg tgggcatgaa tctgatgctg 900
tttccctgca gacaatgcga gagaatgaat cagaattcaa atatctgctt cactcacgga 960
cagaaagact gtttagagtg ctttcccgtg tcagaatctc aacccgtttc tgtcgtcaaa 1020
aaggcgtatc agaaactgtg ctacattcat catatcatgg gaaaggtgcc agacgcttgc 1080
actgcctgcg atctggtcaa tgtggatttg gatgactgca tctttgaaca ataaatgatt 1140
taaatcaggt 1150

<210> SEQ ID NO 57
<211> LENGTH: 2399
<212> TYPE: DNA
<213> ORGANISM: Artificial sequence
<220> FEATURE:
<223> OTHER INFORMATION: the AAV9 cap gene included in the exemplified construct, including the polyadenylation signal of AAV2 having nucleotide numbers 4411 to 4466 of the seq of GenBank NC_001401.2, and an AAV2 rep P5 promoter having nucleotide 190 to to 313 of the seq of

<400> SEQUENCE: 57
atggctgccg atggttatct tccagattgg ctcgaggaca accttagtga agggattcgc 60
gagtggtggg ctttgaaacc tggagcccct caacccaagg caaatcaaca acatcaagac 120
aacgctcgag gtcttgtgct tccgggttac aaataccttg gacccggcaa cggactcgac 180

-continued

```
aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag ccccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaatttttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgcagaccg gctgggttca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta attgcttgtt   2220
aatcaataaa ccgtttaatt cgtttcagtt gaactttggt ctctgcggtt taaacggtcc   2280
tgtattagag gtcacgtgag tgttttgcga cattttgcga caccatgtgg tcacgctggg   2340
tatttaagcc cgagtgagca cgcagggtct ccattttgaa gcgggaggtt tgaacgcgc    2399
```

<210> SEQ ID NO 58
<211> LENGTH: 600
<212> TYPE: DNA

<213> ORGANISM: Artificial sequence
<220> FEATURE:
<223> OTHER INFORMATION: CCMA-560 DNA sequence (query) from Fig. 2

<400> SEQUENCE: 58
tgactttata gtattagaaa tgacagagaa aagacgaggc cccatccctg ctaagttcaa 60
tatttatccg gttttgcgaa ttccgagtgt agttaattaa gtatcatgat aaactgacaa 120
agcggtttct ccaacgaatg ccatgggtgc aacaaaattg atttcagaaa aactattttt 180
ccaagcaaac gaaagtattc cgaatcaaaa aacgaggttt tgctctgtac gctttggcaa 240
tgtgcttgga tctagaggtt ccgttattcc gatcatgctc cagcagctat taaatgaaaa 300
acctttgacc gtgactgatc ctcatatgac acgttttttt atgtccattg aagaggctgt 360
ttccctcaca cttcaagcag caatcatgat gaaaggcggc gaaaccttca ttctcaagat 420
ggagtcctta cagcttgccg atctcctaaa agcgtttcat gaatatgccg ctcaaatcaa 480
tgctaaatct ccggatattc ttgtagtcgg aaaaagacct ggcgaaaagc ttcacgagga 540
gctcacattt ccgcacgaag cagatgcact gtttgaacat gaacaatttt atgccatttt 600

<210> SEQ ID NO 59
<211> LENGTH: 488
<212> TYPE: DNA
<213> ORGANISM: Artificial sequence
<220> FEATURE:
<223> OTHER INFORMATION: nucleotide 464352 to 464839 of whole genome shotgun sequence of Bacillus safensis strain Fairview contig56_1 (Sbjct) from Fig. 2

<400> SEQUENCE: 59
actgacaaag cggtttctcc aacgaatgcc atgggtgcaa caaaattgat ttcagaaaaa 60
ctatttttcc aagcaaacga aagtattcca aataaaaaaa ccaagttttg ctctgtacgc 120
tttggcaatg tgcttggatc tagaggttcc gtgattccga tcatgctcca gcagctatta 180
aatgaaaaac ctttgaccgt gactgatcct catatgacac gttttttat gtccattgaa 240 gaggctgttt ccctcacact tcaagcagca atcatgatga aaggcggcga aaccttcatt 300
ctcaagatgg agtccttaca gcttgccgat ctcctaaaag cgtttcatga atatgccgct 360
caaatcaatg ctaaatctcc ggatattctt gtagtcggaa aaagacctgg cgaaaagctt 420
cacgaggagc tcacatttcc gcacgaagca gatgcactgt ttgaacatga acaattttat 480
gccatttt 488

<210> SEQ ID NO 60
<211> LENGTH: 225
<212> TYPE: DNA
<213> ORGANISM: Artificial sequence
<220> FEATURE:
<223> OTHER INFORMATION: SV40 polyadenylation signal

<400> SEQUENCE: 60
gatacattga tgagtttgga caaaccacaa ctagaatgca gtgaaaaaaa tgctttattt 60
gtgaaatttg tgatgctatt gctttatttg taaccattat aagctgcaat aaacaagtta 120
acaacaacaa ttgcattcat tttatgtttc gggttcaggg ggaggtgtgg gaggtttttt 180
aaagcaagta aaacctctac aaatgtggta tggctgatta tgatc 225

<210> SEQ ID NO 61
<211> LENGTH: 4281
<212> TYPE: DNA
<213> ORGANISM: Artificial sequence
<220> FEATURE:
<223> OTHER INFORMATION: the modified rep gene, including 5'rep, intron 5', stop cassette,intron 3' and 3' rep

<400> SEQUENCE: 61

```
ggtcctgtat tagaggtcac gtgagtgttt tgcgacattt tgcgacacca tgtggtcacg     60
ctgggtattt aagcccgagt gagcacgcag ggtctccatt ttgaagcggg aggtttgaac    120
gcgcagccgc catgccgggg ttttacgaga ttgtgattaa ggtccccagc gaccttgacg    180
agcatctgcc cggcatttct gacagctttg tgaactgggt ggccgagaag gaatgggagt    240
tgccgccaga ttctgacatg gatctgaatc tgattgagca ggcacccctg accgtggccg    300
agaagctgca gcgcgacttt ctgacggaat ggcgccgtgt gagtaaggcc ccggaggccc    360
ttttctttgt gcaatttgag aagggagaga gctacttcca catgcacgtg ctcgtggaaa    420
ccaccggggt gaaatccatg gttttgggac gtttcctgag tcagattcgc gaaaaactga    480
ttcagagaat ttaccgcggg atcgagccga ctttgccaaa ctggttcgcg gtcacaaaga    540
ccagaaatgg cgccggaggc gggaacaagg tggtggatga gtgctacatc cccaattact    600
tgctccccaa aacccagcct gagctccagt gggcgtggac taatatggaa cagtatttaa    660
gcgcctgttt gaatctcacg gagcgtaaac ggttggtggc gcagcatctg acgcacgtgt    720
cgcagacgca ggagcagaac aaagagaatc agaatcccaa ttctgatgcg ccggtgatca    780
gatcaaaaac ttcagccagg tacatggagc tggtcgggtg gctcgtggac aaggggatta    840
cctcggagaa gcagtggatc caggtgggtg tctttcctgc ctgagctgac ctgggcagac    900
gcgtaattaa gtatcatgat aaactgacaa agcggtatat caagatactt aatacatatg    960
gtcctgtaaa agtttaatgt gtaagaagta tttgttataa aagataaata ttcagaatct   1020
tctttttaat tcctgatttt atttctatag gactgaaaga cttgctcgag atgtcatgaa   1080
ggagatggga ggccatcaca ttctcacttc actgcagctc aacgtcccca attctaccgg   1140
gtaggggagg cgcttttccc aaggcagtct ggagcatgcg ctttagcagc cccgctgggc   1200
acttggcgct acacaagtgg cctctggcct cgcacacatt ccacatccac cggtaggcgc   1260
caaccggctc cgttctttgg tggccccttc gcgccacctt ctactcctcc cctagtcagg   1320
aagttccccc ccgccccgca gctcgcgtcg tgcaggacgt gacaaatgga agtagcacgt   1380
ctcactagtc tcgtgcagat ggacagcacc gctgagcaat ggaagcgggt aggcctttgg   1440
ggcagcggcc aatagcagct ttgctccttc gctttctggg ctcagaggct gggaaggggt   1500
gggtccgggg gcgggctcag gggcgggctc aggggcgggg cgggcgcccg aaggtcctcc   1560
ggaggcccgg cattctgcac gcttcaaaag cgcacgtctg ccgcgctgtt ctcctcttcc   1620
tcatctccgg gcctttcgac ctagcgggca gtgagcgcaa cgcaattaat gtgagttagc   1680
tcactcatta ggcaccccag gctttacact ttatgcttcc ggctcgtatg ttgtgtggaa   1740
ttgtgagcgg ataacaattt cacacaggaa acagctgcca ccatgattga acaagatgga   1800
ttgcacgcag gttctccggc cgcttgggtg gagaggctat tcggctatga ctgggcacaa   1860
cagacaatcg gctgctctga tgccgccgtg ttccggctgt cagcgcaggg gcgcccggtt   1920
ctttttgtca agaccgacct gtccggtgcc ctgaatgaac tgcaagacga ggcagcgcgg   1980
ctatcgtggc tggccacgac gggcgttcct tgcgcagctg tgctcgacgt tgtcactgaa   2040
gcgggaaggg actggctgct attgggcgaa gtgccggggc aggatctcct gtcatctcac   2100
cttgctcctg ccgagaaagt atccatcatg gctgatgcaa tgcggcggct gcatacgctt   2160
gatccggcta cctgcccatt cgaccaccaa gcgaaacatc gcatcgagcg agcacgtact   2220
```

```
cggatggaag ccggtcttgt cgatcaggat gatctggacg aagagcatca ggggctcgcg   2280
ccagccgaac tgttcgccag gctcaaggcg agcatgcccg acggcgagga tctcgtcgtg   2340
acccatggcg atgcctgctt gccgaatatc atggtggaaa atggccgctt ttctggattc   2400
atcgactgtg gccggctggg tgtggcggac cgctatcagg acatagcgtt ggctacccgt   2460
gatattgctg aagagcttgg cggcgaatgg gctgaccgct tcctcgtgct ttacggtatc   2520
gccgctcccg attcgcagcg catcgccttc tatcgccttc ttgacgagtt cttctgagat   2580
acattgatga gtttggacaa accacaacta gaatgcagtg aaaaaaatgc tttatttgtg   2640
aaatttgtga tgctattgct ttatttgtaa ccattataag ctgcaataaa caagttaaca   2700
acaacaattg cattcatttt atgtttcggg ttcaggggga ggtgtgggag gtttttaaa    2760
gcaagtaaaa cctctacaaa tgtggtatgg ctgattatga tcgcatagtg ttaccatcaa   2820
ccaccttaac ttcatttttc ttattcaata cctaggtagg tagatgctag attctggaaa   2880
taaaatatga gtctcaagtg gtccttgtcc tctctcccag tcaaattctg aatctagttg   2940
gcaagattct gaaatcaagg catataatca gtaataagtg atgatagaag ggtatataga   3000
aggctagccg tcaacatctc cactgacaaa gcggtttctc caacgaatta tcgattcggc   3060
tgtggggtcc tgtggtgtgt ggggagctgt cacatccagg gtcctcactg cctgtcccct   3120
tccctcctca ggaggaccag gcctcataca tctccttcaa tgcggcctcc aactcgcggt   3180
cccaaattaa ggctgccttg gacaatgcgg gaaagattat gagcctgact aaaaccgccc   3240
ccgactacct ggtgggccag cagcccgtgg aggacatttc cagcaatcgg atttataaaa   3300
ttttggaact aaacgggtac gatccccaat atgcggcttc cgtctttctg ggatgggcca   3360
cgaaaaagtt cggcaagagg aacaccatct ggctgtttgg gcctgcaact accgggaaga   3420
ccaacatcgc ggaggccata gcccacactg tgcccttcta cgggtgcgta aactggacca   3480
atgagaactt tcccttcaac gactgtgtcg acaagatggt gatctggtgg gaggagggga   3540
agatgaccgc caaggtcgtg gagtcggcca aagccattct cggaggaagc aaggtgcgcg   3600
tggaccagaa atgcaagtcc tcggcccaga tagacccgac tcccgtgatc gtcacctcca   3660
acaccaacat gtgcgccgtg attgacggga actcaacgac cttcgaacac cagcagccgt   3720
tgcaagaccg gatgttcaaa tttgaactca cccgccgtct ggatcatgac tttgggaagg   3780
tcaccaagca ggaagtcaaa gactttttcc ggtgggcaaa ggatcacgtg gttgaggtgg   3840
agcatgagtt ctacgtcaaa aagggtggag ccaagaaaag acccgccccc agtgacgcag   3900
atataagtga gcccaaacgg gtgcgcgagt cagttgcgca gccatcgacg tcagacgcgg   3960
aagcttcgat caactacgca gacaggtacc aaaacaaatg ttctcgtcac gtgggcatga   4020
atctgatgct gtttccctgc agacaatgcg agagaatgaa tcagaattca aatatctgct   4080
tcactcacgg acagaaagac tgtttagagt gctttcccgt gtcagaatct caacccgttt   4140
ctgtcgtcaa aaaggcgtat cagaaactgt gctacattca tcatatcatg ggaaaggtgc   4200
cagacgcttg cactgcctgc gatctggtca atgtggattt ggatgactgc atctttgaac   4260
aataaatgat ttaaatcagg t                                             4281
```

<210> SEQ ID NO 62
<211> LENGTH: 20
<212> TYPE: DNA
<213> ORGANISM: Artificial Sequence
<220> FEATURE:
<223> OTHER INFORMATION: AAVRT-F1

<400> SEQUENCE: 62
tgatgcgccg gtgatcagat 20

<210> SEQ ID NO 63
<211> LENGTH: 24
<212> TYPE: DNA
<213> ORGANISM: Artificial Sequence
<220> FEATURE:
<223> OTHER INFORMATION: P349R9

<400> SEQUENCE: 63
gtagaagggc acagtgtggg ctat 24

<210> SEQ ID NO 64
<211> LENGTH: 20
<212> TYPE: DNA
<213> ORGANISM: Artificial Sequence
<220> FEATURE:
<223> OTHER INFORMATION: Splice Donor Site in 5'REP

<400> SEQUENCE: 64
cttcagccag gtacatggag 20

<210> SEQ ID NO 65
<211> LENGTH: 20
<212> TYPE: DNA
<213> ORGANISM: Artificial Sequence
<220> FEATURE:
<223> OTHER INFORMATION: Mutated Splice Donor Site in 5'REP

<400> SEQUENCE: 65
cttcagccag atacatggag 20

<210> SEQ ID NO 66
<211> LENGTH: 2000
<212> TYPE: DNA
<213> ORGANISM: Artificial Sequence
<220> FEATURE:
<223> OTHER INFORMATION: Intron Spacer

<400> SEQUENCE: 66
ttacgtataa tacctccacg ttgagaccgt acgagcgcat aacggaagcg ttgttgagac 60
ccagtcgcct gtgataccgc cttggttaag gcccgtagcc tagcttaagg caacgaaaca 120
agacgactca ggagaatcat tatgaacagg gcgcgcggga ggtcgtggat atggccggta 180
ttttacttat gggaggatct tttggccgcg agacttccga gaaaccatca acagttcgat 240
ttcctccttt tatccttaac atagcacaga gttgccacat tgataggggg gcaggagatc 300
gtcacatgaa ccgacggtcg ggacatattc gatgccgtcc cctctcgaca accggattcc 360
tcgtttccaa tcgaatacca cgccccgggg atcgtgcgca cgataagcac aataagcgtc 420
actgcggggt caagctgtgg cttgcaggat gctaactcgt aacgacatta agacagcaga 480
gcaatgggcg acccaaaaag tttaagcctt tacctcgggg tggcaacata agtgtgccga 540
ctacgacagg aacccatgac tcctttgggg cgttctaatg ggcggggtct gctgttaacc 600
agctgatggg gcaagtggaa tagagcatgc cctacgcgct attaaggaat gcgtggctac 660
ttggctgtgc gtacttgctc aatgtatggc aacaaacaac ctaatctttg tcggcaacgc 720
gataatctcg ccacgttaat cggctacttg catggtagga ttcgatttta cgtatgtacc 780
acggattcta ttgcacgcta cagcatcaat gtgcccgatg actactagct gcccagaggg 840
gataaatcat gtgtaatttg gcgtgcattc gagttattgg cattaatttc tctatcaagt 900

```
gcagtcccta gcttcgagta agctatgcgt tcccccccgt acattttaat cccataggga    960
acggcacccg cacctattaa gagagcgcca tagctctaaa cgacccacgg tccaatgctt   1020
ataatttcta aaatttaagg tcgcattgcc ttgaccgtta gtccccctca cgtttgaggg   1080
cataatgttc ctgcgccctt tacaattagt ctaattctac ttaaaatcga cgcaggattt   1140
tttctgttgg ctccgctgcc atgggaagct gtctatggag ggctcggtta tccctggctt   1200
cttactatgt aatctacctt tacctttgct aattacgtgt acgtgaccag aaactacacg   1260
gaacgagtgg gacccataag ctgagcgatg gctagtgaga ccgcctgata tgactcacgg   1320
ggtaaccgtg caacgtgcat atatctaatg agtacggcac ctttccactt tgcttatatg   1380
agagtacagg ctacttagcc cgacgtgtac gccagatctg ggcacccgcc agcaggtccc   1440
actaggccgg cctgccaggc aaatgacctg agtgccgcga ctagcctcgg ccagacagct   1500
gactagcgat tcacaagtgc cgacttagta gttctttagc aatagaaata tagacatagt   1560
tccctcgaac tacagggaaa tacggcctgt ggttgcaaga taagaggctt ttaacactga   1620
cgtagtttac acactctggc cggaccatga atttcgtctg ctcccacgaa ccacattatc   1680
agtacttctt cttaagtgtt ttattaaatc gaataatcta caaatagttc taaaggagcg   1740
agttagagag aagttccacg ctccataact tcgagaccgt tagcgaagtt ttccagcaca   1800
cggctacggg accctgcact cagcttcatg gttttaggca cgagaaccgc atatagtgga   1860
gatttcgccg tggaagcaag tctgtcttag agagcctagg tgcttaggtt ttcggaactc   1920
tcctgattat attcaatttc catcccattc tggatcatca agtgcccgcg gatgacctac   1980
gggcaaattg ccccagataa                                               2000
```

```
<210> SEQ ID NO 67
<211> LENGTH: 2072
<212> TYPE: DNA
<213> ORGANISM: Artificial Sequence
<220> FEATURE:
<223> OTHER INFORMATION: Spacer 2

<400> SEQUENCE: 67
```

```
gtagtcccgc agtacgcggc taggcagatc ggccccttcc aaatccgtgt catcggaaga     60
ccatgttggt agtttcataa tggattttat tgattgctat gtaacctgaa cgacggtatt    120
aatgggcttc ttaacatgaa cgtgagtaac ggaaacatta cgcttttcgg tcgcgaatga    180
cggcgaactc tgggccttgt gggattatag atacgtcagt gttcctcggg aacggacaaa    240
gtaggaaata tcgacgacat ggatcatgcc aatatatcaa cgcgggaaga tgaccattga    300
tgcagtggga actggtgtcc cacaaatatc tagggcttgt gcagcggtca agggctgtgt    360
tccacctggg acgccagccc aattatacgc cagaaacgct tgattttact caggtagaaa    420
gggggaaaat acactacgcg accaactaat aattcctttc gcaaacttaa tggctgctaa    480
ttttcctcaa gaccggctta atgcctacta cacttaaggc gcggatggcg agatacgacg    540
cgggcacata ctaggcacgt catcggccag gcgttctaat ttaagttcac gcataaataa    600
gcgtctctcg agactgcaga tccccgtctt aaatttagta cacaacgctg tttaccaccg    660
gggcgttatg acttgcagac ccgtgcgtga atatcctgta tcattcatca ctgctgggac    720
taccccactt tacatatcta agggattcaa caaacttcgg gtggttaatg tcaagtgcgt    780
tattggcgta taacagggtg aatgcacatt gatggaatgc cttcaaccaa gctgtggcgt    840
cacgccagcc gaacacgttt tacccaaact tagccctttt gctgcgaccc tgctatctat    900
```

tggctatact ctatatgcaa tgggtgcaga tcggagaccg cgccattgtc accaccccaa 960
ggaggggaga ttcacgctcg ctcggattag cttcccggat catttatcaa aactggaaat 1020
actctaagct aagttcacct tcagatcctt gtcaagagtt gtcggcccga ttagtcgttg 1080
cgcacacgtg gcgtaattac agcacgcgag gtacattcga gtttatcctc tgggctccat 1140
tcaggcaata tgctgtcagc acgaagagtg tgacctggcg ctattgttgg cgacttgacg 1200
ccacggaata ccagtgtata tacatcctag gagaactgca agacttcggg cgtgtatcgt 1260
aggttatggt agtcactggg atttgcacct gcgcacaatc tgtttggtaa agtaaaagcg 1320
atacttcgcg actcccaata agtaacgata ctgcgcggca tcccttagcg ctctcatacc 1380
gagcgagata cagtctatat actcaacaga gcacgtttgg aacctgtgag gttcagcacc 1440
aatcattcat ctataaactc atcgagaaaa gtatggaggc cacgtgggct tcttcggttc 1500
agctaagcag actcatgagg gtgtggtctc ggctttggag gcagatattg tccggaattg 1560
taattgcgac tgcgcggcag tatagagtgt ctctatcatt gtaggactca cgcacccatc 1620
ggacaaccac gtgatggccc cttagttata tcgagggata ggggctatgc tcaagttagt 1680
cttaatttcg cgtgcttgca aggcttatcg ccggtccctc ctaccgtacc cggcctttca 1740
gggccatgat ctttgcctgc ttccctgttt atctacacca atattgggag acttgtatga 1800
cgagcgagcc actaaagagg acgattgtca acagggtgct ttatcacata atagcctgtt 1860
tctccaacag tgcttcaatt acctagcatc acagaatgcg ataagcccac cacgtgtttc 1920
ccaatggcgg ctattcatta atcgggacga cacccctatt cgtggagaga gcatcctatt 1980
gagtccgagc tgttagcgca tgattacggt gggccagaca gattcgacgg aatgccgcta 2040
ctacgctggc gcgtaatcag tcggaaccag aa 2072

<210> SEQ ID NO 68
<211> LENGTH: 2091
<212> TYPE: DNA
<213> ORGANISM: Artificial Sequence
<220> FEATURE:
<223> OTHER INFORMATION: Spacer 3

<400> SEQUENCE: 68
tgtacacaat gatacgatcc cgtttctgcg acgtactcgg gtgtagctgg gaccctgtcg 60
catttaatcg ccggtcaata ggtacaccgt gctgatcttg gatactcctg atcgcgatgt 120
aacccgagcg gcgctactaa tgggcgtcct aacacgagcg cgaataacca cttgcgctag 180
gcaggattta cgatggtcat ctggaacgga cgggtacacc atgccaaaat ttgctcctag 240
ttcacaaggt caaacggtga cccggaggcc agtccactcc ttgtcctcgt ccttacgtta 300
ccgtaacctc tgacctggag cctaaggctg ctccggcatt ttaaaaacca cacaaataag 360
gcttcacact attcctatta tcttgtgtcc tacctaagag gtagtggagc gagtaggtag 420
acacaggcac tcaccaccga tgttccgccc atgggccatg gttaaggtcc gaatgaaacc 480
cgtatgcaag ttaccggcct tatattaata aggttggtat acatcctaaa agctctctcg 540
gacgtgacca aatacaggca tccacggagc actactgaat gggcacgtgg accggcgagt 600
gagaaatcga gcagcattaa gtcattctta gtaagccgag atgggtctgc gttatgtacg 660
tctagtgggg aaacaagttg gtggacaaac gttacgccta aggagctaat atttcggtca 720
ggttgcgctg ggtcaaatca accggtcctg gtaacggagc gatggttagg tgtattacac 780
tagcgatggg ccgtgccgga tggtacgcca cgttctccga gccagtgaaa ttggatgaga 840
actcgtaaat ctctcgttgc aaacagcttc ctcaatatat gacctggcca ctgatgagag 900

```
ggtaacactt aattcctaga atgtctgacg acatcaccct taagcagaca cactgcgatg    960

tgtggacgct agggtgtctc tttccacgtt tgacttagcc catgatgtct tgactaagat   1020

ggcagggtat ttccccttat tcgtgtatgt accactatta ccgtcgattg accgtcgccg   1080

cttatacgtc gtgccctgtg ccttggcaat tttgtccctg gataacccgc cttgcttcta   1140

tcgaggtcct tgaataagtt aatgcaactt gtggaggaac atagggaatg tggcgtgctg   1200

cttagatatg gagtgcaaga agtcctctgg gttgtagttt cactgttacg tcctagccag   1260

tgaagcactg gcatgcagct ttatctgagg attccactca ctgcttacaa gaatttgcca   1320

agctggtgcc gatatgaccc caacgctatc cagagtttaa gttgtcatct ctctccatca   1380

taattgccac agtgtgttgt gtctacgaat agctattaaa ataccagccc ctgagaacga   1440

tgcccgacac atagggcagt gcaggcagca taacgtgcag atcaacataa tttccactaa   1500

gtgttgatat agtttactgg ctgagagccg ccatattgga acgacgacga gagcgcgtat   1560

cctgcccaac cagaaatacg tgtccaatcc atataactga ccaaagctgc ggacagtttc   1620

ctctccacct acaacgggat tagcgcactt gcttgtagtg aggcaggtat aacccacggc   1680

acgtaacacc tttagacgtt cggttccgca atcgcacaat gtactactat tagagaacta   1740

tagcaaggaa cttatagcgt atcgaaagtt catccctgcg gcccatagcc gtaaccaccg   1800

tggggttatt ttaaacttta agttgtaccc tcaggcaagc gaagaccggt actttaccta   1860

catggggccg ctttccgagc cacgccgcac cccaacatat tcctacgcgc tgtaataatg   1920

aacataagag aaaatggagt tgggtgacag cacatatcga ctacctagcg actaccgcaa   1980

cacaaagtag atcccgccgg tatcctcctt tcatgcagga cgggttaccc aggaatgcgt   2040

ttgtttgact ggtgcccgct gaggcgctga atatctcgcg atagcgtgta c            2091
```

<210> SEQ ID NO 69
<211> LENGTH: 2794
<212> TYPE: DNA
<213> ORGANISM: Artificial Sequence
<220> FEATURE:
<223> OTHER INFORMATION: mCherry-IRES-SEAP coding sequences

<400> SEQUENCE: 69

```
atggtgagca agggcgagga ggataacatg gccatcatca aggagttcat gcgcttcaag     60

gtgcacatgg agggctccgt gaacggccac gagttcgaga tcgagggcga gggcgagggc    120

cgcccctacg agggcaccca gaccgccaag ctgaaggtga ccaagggtgg cccccctgccc    180

ttcgcctggg acatcctgtc ccctcagttc atgtacggct ccaaggccta cgtgaagcac    240

cccgccgaca tccccgacta cttgaagctg tccttccccg agggcttcaa gtgggagcgc    300

gtgatgaact tcgaggacgg cggcgtggtg accgtgaccc aggactcctc cctgcaggac    360

ggcgagttca tctacaaggt gaagctgcgc ggcaccaact tcccctccga cggccccgta    420

atgcagaaga agaccatggg ctgggaggcc tcctccgagc ggatgtaccc cgaggacggc    480

gccctgaagg gcgagatcaa gcagaggctg aagctgaagg acggcggcca ctacgacgct    540

gaggtcaaga ccacctacaa ggccaagaag cccgtgcagc tgcccggcgc ctacaacgtc    600

aacatcaagt tggacatcac ctcccacaac gaggactaca ccatcgtgga acagtacgaa    660

cgcgccgagg gccgccactc caccggcggc atggacgagc tgtacaagta agtcgactac    720

tggccgaagc cgcttggaat aaggccggtg tgcgtttgtc tatatgtgat tttccaccat    780

attgccgtct tttggcaatg tgagggcccg gaaacctggc cctgtcttct tgacgagcat    840
```

-continued

```
tcctaggggt ctttcccctc tcgccaaagg aatgcaaggt ctgttgaatg tcgtgaagga    900

agcagttcct ctggaagctt cttgaagaca aacaacgtct gtagcgaccc tttgcaggca    960

gcggaacccc ccacctggcg acaggtgcct ctgcggccaa aagccacgtg tataagatac   1020

acctgcaaag gcggcacaac cccagtgcca cgttgtgagt tggatagttg tggaaagagt   1080

caaatggctc tcctcaagcg tattcaacaa ggggctgaag gatgcccaga aggtacccca   1140

ttgtatggga tctgatctgg ggcctcggtg cacatgcttt acatgtgttt agtcgaggtt   1200

aaaaaacgtc taggcccccc gaaccacggg gacgtggttt tcctttgaaa aacacgatcg   1260

tacggccacc atgtggggag cctgcttgct gctgctgggc ctcagcctac aggtgtgccc   1320

gagcgtcatc ccagtggagg aggagaatcc agccttctgg aaccgaaagg cagccgaggc   1380

cctggatgct gccaagaagc tgaagcccat tcagacatca gctaagaacc tcgttatcct   1440

catgggagat gggatggggg tgtctacagt aaccgctacc cggatcttaa aggggcagca   1500

gcaaggccat ctgggacctg agacacagtt agctatggat cgctttccac acatggctct   1560

gtccaagaca tacaacacag acaagcagat cccggacagc gcaggcacag gtacagcctt   1620

tctctgcggg gtcaaaacca acatgaaggt cattggcttg agtgcagctg cacgcttcaa   1680

ccagtgcaac acgacatggg gtaacgaggt cgtctcggtg atgcaccgtg ctaagaaagc   1740

aggaaagtct gtgggagtgg tgaccaccac gtcggtgcag catgcttctc cggccggcac   1800

ctacgcgcac actgtgaacc gtggttggta ctcggatgca caaatgcctg cctcagcgct   1860

acaggatggc tgcaaagaca tctctactca gctcatctcc aacatggaca ttgatgtgat   1920

cctcggtggt ggccgcaagt tcatgtttcc caaggggaca ccagaccagg aatatccaac   1980

tgacaccaag caggctggaa ccaggctgga tggacgcaac ctagttcaag agtggctggc   2040

aaagcaccag ggagcccggt atgtttggaa ccgctcagag ctgattcagg catccctgaa   2100

ccgatctgtg acacacctca tgggcctctt tgagcctaac gacatgaaat atgaaatcca   2160

ccgagaccct gctcaggacc cttccctggc cgagatgacg gaggtggctg tgcgcatgct   2220

cagcaggaac cccaaaggct tctatctctt tgtggaaggg ggtcgcatcg accatggcca   2280

ccatgaaact gtagcctatc gtgccctgac tgaggctgtc atgttcgact cggctgttga   2340

caaggcagac aagctcacca gtgagcagga cacgatgatc cttgtcactg ccgaccactc   2400

tcacgtcttc tcttttggtg gttacacaca gagaggggct tccatctttg gactggctcc   2460

cttcaaggct gaggatggca aatcctttac ctcgatacta tacggcaacg gtcctggtta   2520

caagctccat aatggcgccc gggctgatgt cactgaggaa gagagcagca accccacgta   2580

ccagcagcag gctgctgtac ccctgtcgtc agagacccac agcggggagg acgtggcaat   2640

attcgcgcgt ggcccacagg cgcagctggt gcacggagtt caggagcaga actacatcgc   2700

gcacgtcatg gccttcgcag cctgcctgga gccctacact gactgcggcc tggcatcccc   2760

tgctggccag agcagtgcag tgagcccggg ctga                               2794
```

<210> SEQ ID NO 70
<211> LENGTH: 22126
<212> TYPE: DNA
<213> ORGANISM: Artificial Sequence
<220> FEATURE:
<223> OTHER INFORMATION: P600

<400> SEQUENCE: 70

```
taactataac ggtcctaagg tagcgaagat atccgatcaa gaaagcactc cgggctccag     60

aaggagcctt ccaggccagc tttgagcata agctgctgat gagcagtgag tgtcttgagt    120
```

-continued

```
agtgttcagg gcagcatgtt accattcatg cttgacttct agccagtgtg acgagaggct    180
ggagtcaggt ctctagagag ttgagcagct ccagccttag atctcccagt cttatgcggt    240
gtgcccattc gctttgtgtc tgcagtcccc tggccacacc cagtaacagt tctgggatct    300
atgggagtag cttccttagt gagctttccc ttcaaatact ttgcaaccag gtagagaagt    360
ttggagtgaa ggttttgttc ttcgtttctt cacaatatgg atatgcatct tcttttgaaa    420
atgttaaagt aaattacctc tcttttcaga tactgtcttc atgcgaactt ggtatcctgt    480
ttccatccca gccttctata acccagtaac atctttttg aaaccagtgg gtgagaaaga     540
cacctggtca ggaacgcgga ccacaggaca actcaggctc acccacggca tcagactaaa    600
ggcaaacaag gactctgtat aaagtaccgg tggcatgtgt attagtggag atgcagcctg    660
tgctctgcag acagggagtc acacagacac ttttctataa tttcttaagt gctttgaatg    720
ttcaagtaga aagtctaaca ttaaatttga ttgaacaatt gtatattcat ggaatatttt    780
ggaacggaat accaaaaaat ggcaatagtg gttctttctg gatggaagac aaacttttct    840
tctttaaaat aaattttatt ttatatattt gaggttgacc acatgacctt aaggatacat    900
atagacagta aactggttac tacagtgaag caaattaaca tatctaccat cgtacatagt    960
tacattttt tgtgtgacag gaacagctaa aatctacgta tttaacaaaa ctcctaaaga    1020
caatacattt ttattaacta tagccctcat gatgtacatt agatcctctc ttaaggtagc   1080
ccgaataaaa atagaaaaac aacaaatgtt aattttctat ttttatttgg tgtcgtactc   1140
aatccataat cgtcacaagc gttatagttt aagtacaaca atgtcgtcac cttgttggtg   1200
taattaggtt tacgccaaca gggtgataac aggcgcgccg gtcctgtatt agaggtcacg   1260
tgagtgtttt gcgacatttt gcgacaccat gtggtcacgc tgggtattta agcccgagtg   1320
agcacgcagg gtctccattt tgaagcggga ggtttgaacg cgcagccgcc atgccggggt   1380
tttacgagat tgtgattaag gtccccagcg accttgacga gcatctgccc ggcatttctg   1440
acagctttgt gaactgggtg gccgagaagg aatgggagtt gccgccagat tctgacatgg   1500
atctgaatct gattgagcag gcacccctga ccgtggccga gaagctgcag cgcgactttc   1560
tgacggaatg gcgccgtgtg agtaaggccc cggaggccct tttctttgtg caatttgaga   1620
agggagagag ctacttccac atgcacgtgc tcgtggaaac caccggggtg aaatccatgg   1680
ttttgggacg tttcctgagt cagattcgcg aaaaactgat tcagagaatt taccgcggga   1740
tcgagccgac tttgccaaac tggttcgcgg tcacaaagac cagaaatggc gccggaggcg   1800
ggaacaaggt ggtggatgag tgctacatcc ccaattactt gctccccaaa acccagcctg   1860
agctccagtg ggcgtggact aatatggaac agtatttaag cgcctgtttg aatctcacgg   1920
agcgtaaacg gttggtggcg cagcatctga cgcacgtgtc gcagacgcag gagcagaaca   1980
aagagaatca gaatcccaat tctgatgcgc cggtgatcag atcaaaaact tcagccagat   2040
acatggagct ggtcgggtgg ctcgtggaca aggggattac ctcggagaag cagtggatcc   2100
aggtgggtgt ctttcctgcc tgagctgacc tgggcagacg cgtaattaag tatcatgata   2160
aactgacaaa gcggtatatc aagatactta atacatatgg tcctgtaaaa gtttaatgtg   2220
taagaagtat ttgttataaa agataaatat tcagaatctt ctttttaatt cctgatttta   2280
tttctatagg actgaaagac ttgctcgaga tgtcatgaag gagatgggag gccatcacat   2340
tctcacttca ctgcagctca acgtccccaa ttctaccggg taggggaggc gcttttccca   2400
aggcagtctg gagcatgcgc tttagcagcc ccgctgggca cttggcgcta cacaagtggc   2460
```

-continued

```
ctctggcctc gcacacattc cacatccacc ggtaggcgcc aaccggctcc gttctttggt   2520
ggccccttcg cgccaccttc tactcctccc ctagtcagga agttcccccc cgccccgcag   2580
ctcgcgtcgt gcaggacgtg acaaatggaa gtagcacgtc tcactagtct cgtgcagatg   2640
gacagcaccg ctgagcaatg gaagcgggta ggcctttggg gcagcggcca atagcagctt   2700
tgctccttcg ctttctgggc tcagaggctg ggaaggggtg ggtccggggg cgggctcagg   2760
ggcgggctca ggggcggggc gggcgcccga aggtcctccg gaggcccggc attctgcacg   2820
cttcaaaagc gcacgtctgc cgcgctgttc tcctcttcct catctccggg cctttcgacc   2880
tagcgggcag tgagcgcaac gcaattaatg tgagttagct cactcattag gcaccccagg   2940
ctttacactt tatgcttccg gctcgtatgt tgtgtggaat tgtgagcgga taacaatttc   3000
acacaggaaa cagctgccac catgattgaa caagatggat tgcacgcagg ttctccggcc   3060
gcttgggtgg agaggctatt cggctatgac tgggcacaac agacaatcgg ctgctctgat   3120
gccgccgtgt tccggctgtc agcgcagggg cgcccggttc tttttgtcaa gaccgacctg   3180
tccggtgccc tgaatgaact gcaagacgag gcagcgcggc tatcgtggct ggccacgacg   3240
ggcgttcctt gcgcagctgt gctcgacgtt gtcactgaag cgggaaggga ctggctgcta   3300
ttgggcgaag tgccggggca ggatctcctg tcatctcacc ttgctcctgc cgagaaagta   3360
tccatcatgg ctgatgcaat gcggcggctg catacgcttg atccggctac ctgcccattc   3420
gaccaccaag cgaaacatcg catcgagcga gcacgtactc ggatggaagc cggtcttgtc   3480
gatcaggatg atctggacga agagcatcag gggctcgcgc cagccgaact gttcgccagg   3540
ctcaaggcga gcatgcccga cggcgaggat ctcgtcgtga cccatggcga tgcctgcttg   3600
ccgaatatca tggtggaaaa tggccgcttt tctggattca tcgactgtgg ccggctgggt   3660
gtggcggacc gctatcagga catagcgttg gctacccgtg atattgctga agagcttggc   3720
ggcgaatggg ctgaccgctt cctcgtgctt tacggtatcg ccgctcccga ttcgcagcgc   3780
atcgccttct atcgccttct tgacgagttc ttctgagata cattgatgag tttggacaaa   3840
ccacaactag aatgcagtga aaaaaatgct ttatttgtga aatttgtgat gctattgctt   3900
tatttgtaac cattataagc tgcaataaac aagttaacaa caacaattgc attcatttta   3960
tgtttcgggt tcagggggag gtgtgggagg ttttttaaag caagtaaaac ctctacaaat   4020
gtggtatggc tgattatgat cgcatagtgt taccatcaac caccttaact tcattttttct   4080
tattcaatac ctaggtaggt agatgctaga ttctggaaat aaaatatgag tctcaagtgg   4140
tccttgtcct ctctcccagt caaattctga atctagttgg caagattctg aaatcaaggc   4200
atataatcag taataagtga tgatagaagg gtatatagaa ggctagccgt caacatctcc   4260
actgacaaag cggtttctcc aacgaattat cgatttacgt ataatacctc cacgttgaga   4320
ccgtacgagc gcataacgga agcgttgttg agacccagtc gcctgtgata ccgccttggt   4380
taaggcccgt agcctagctt aaggcaacga aacaagacga ctcaggagaa tcattatgaa   4440
cagggcgcgc gggaggtcgt ggatatggcc ggtattttac ttatgggagg atcttttggc   4500
cgcgagactt ccgagaaacc atcaacagtt cgatttcctc cttttatcct taacatagca   4560
cagagttgcc acattgatag gggggcagga gatcgtcaca tgaaccgacg gtcgggacat   4620
attcgatgcc gtcccctctc gacaaccgga ttcctcgttt ccaatcgaat accacgcccc   4680
ggggatcgtg cgcacgataa gcacaataag cgtcactgcg ggtcaagct gtggcttgca   4740
ggatgctaac tcgtaacgac attaagacag cagagcaatg ggcgacccaa aaagtttaag   4800
cctttacctc ggggtggcaa cataagtgtg ccgactacga caggaaccca tgactccttt   4860
```

```
ggggcgttct aatgggcggg gtctgctgtt aaccagctga tggggcaagt ggaatagagc   4920
atgccctacg cgctattaag gaatgcgtgg ctacttggct gtgcgtactt gctcaatgta   4980
tggcaacaaa caacctaatc tttgtcggca acgcgataat ctcgccacgt taatcggcta   5040
cttgcatggt aggattcgat tttacgtatg taccacggat tctattgcac gctacagcat   5100
caatgtgccc gatgactact agctgcccag aggggataaa tcatgtgtaa tttggcgtgc   5160
attcgagtta ttggcattaa tttctctatc aagtgcagtc cctagcttcg agtaagctat   5220
gcgttccccc ccgtacattt taatcccata gggaacggca cccgcaccta ttaagagagc   5280
gccatagctc taaacgaccc acggtccaat gcttataatt tctaaaattt aaggtcgcat   5340
tgccttgacc gttagtcccc ctcacgtttg agggcataat gttcctgcgc cctttacaat   5400
tagtctaatt ctacttaaaa tcgacgcagg atttttctg ttggctccgc tgccatggga   5460
agctgtctat ggagggctcg gttatccctg gcttcttact atgtaatcta cctttacctt   5520
tgctaattac gtgtacgtga ccagaaacta cacggaacga gtgggaccca taagctgagc   5580
gatggctagt gagaccgcct gatatgactc acggggtaac cgtgcaacgt gcatatatct   5640
aatgagtacg gcacctttcc actttgctta tatgagagta caggctactt agcccgacgt   5700
gtacgccaga tctgggcacc cgccagcagg tcccactagg ccggcctgcc aggcaaatga   5760
cctgagtgcc gcgactagcc tcggccagac agctgactag cgattcacaa gtgccgactt   5820
agtagttctt tagcaataga aatatagaca tagttccctc gaactacagg gaaatacggc   5880
ctgtggttgc aagataagag gcttttaaca ctgacgtagt ttacacactc tggccggacc   5940
atgaatttcg tctgctccca cgaaccacat tatcagtact tcttcttaag tgttttatta   6000
aatcgaataa tctacaaata gttctaaagg agcgagttag agagaagttc cacgctccat   6060
aacttcgaga ccgttagcga agttttccag cacacggcta cgggaccctg cactcagctt   6120
catggtttta ggcacgagaa ccgcatatag tggagatttc gccgtggaag caagtctgtc   6180
ttagagagcc taggtgctta ggttttcgga actctcctga ttatattcaa tttccatccc   6240
attctggatc atcaagtgcc cgcggatgac ctacgggcaa attgccccag ataaattcgg   6300
ctgtggggtc ctgtggtgtg tggggagctg tcacatccag ggtcctcact gcctgtcccc   6360
ttccctcctc aggaggacca ggcctcatac atctccttca atgcggcctc caactcgcgg   6420
tcccaaatta aggctgcctt ggacaatgcg ggaaagatta tgagcctgac taaaaccgcc   6480
cccgactacc tggtgggcca gcagcccgtg gaggacattt ccagcaatcg gatttataaa   6540
attttggaac taaacgggta cgatccccaa tatgcggctt ccgtctttct gggatgggcc   6600
acgaaaaagt tcggcaagag gaacaccatc tggctgtttg ggcctgcaac taccgggaag   6660
accaacatcg cggaggccat agcccacact gtgcccttct acgggtgcgt aaactggacc   6720
aatgagaact ttcccttcaa cgactgtgtc gacaagatgg tgatctggtg ggaggagggg   6780
aagatgaccg ccaaggtcgt ggagtcggcc aaagccattc tcggaggaag caaggtgcgc   6840
gtggaccaga aatgcaagtc ctcggcccag atagacccga ctcccgtgat cgtcacctcc   6900
aacaccaaca tgtgcgccgt gattgacggg aactcaacga ccttcgaaca ccagcagccg   6960
ttgcaagacc ggatgttcaa atttgaactc acccgccgtc tggatcatga ctttgggaag   7020
gtcaccaagc aggaagtcaa agactttttc cggtgggcaa aggatcacgt ggttgaggtg   7080
gagcatgagt tctacgtcaa aaagggtgga gccaagaaaa gacccgcccc cagtgacgca   7140
gatataagtg agcccaaacg ggtgcgcgag tcagttgcgc agccatcgac gtcagacgcg   7200
```

-continued

```
gaagcttcga tcaactacgc agacaggtac caaaacaaat gttctcgtca cgtgggcatg   7260
aatctgatgc tgtttccctg cagacaatgc gagagaatga atcagaattc aaatatctgc   7320
ttcactcacg gacagaaaga ctgtttagag tgctttcccg tgtcagaatc tcaacccgtt   7380
tctgtcgtca aaaaggcgta tcagaaactg tgctacattc atcatatcat gggaaaggtg   7440
ccagacgctt gcactgcctg cgatctggtc aatgtggatt tggatgactg catctttgaa   7500
caataaatga tttaaatcag gtatggctgc cgatggttat cttccagatt ggctcgagga   7560
caaccttagt gaagggattc gcgagtggtg ggctttgaaa cctggagccc ctcaacccaa   7620
ggcaaatcaa caacatcaag acaacgctcg aggtcttgtg cttccgggtt acaaatacct   7680
tggacccggc aacggactcg acaaggggga gccggtcaac gaagcagacg cggcggccct   7740
cgagcacgac aaggcctacg accagcagct caaggccgga gacaacccgt acctcaagta   7800
caaccacgcc gacgccgagt tccaggagcg gctcaaagaa gatacgtctt ttgggggcaa   7860
cctcgggcga gcagtcttcc aggccaaaaa gaggcttctt gaacctcttg gtctggttga   7920
ggaagcggct aagacggctc ctggaaagaa gaggcctgta gagcagtctc ctcaggaacc   7980
ggactcctcc gtgggtattg gcaaatcggg tgcacagccc gctaaaaaga gactcaattt   8040
cggtcagact ggcgacacag agtcagtccc agaccctcaa ccaatcggag aacctcccgc   8100
agccccctca ggtgtgggat ctcttacaat ggcttcaggt ggtggcgcac cagtggcaga   8160
caataacgaa ggtgccgatg gagtgggtag ttcctcggga aattggcatt gcgattccca   8220
atggctgggg gacagagtca tcaccaccag cacccgaacc tgggccctgc ccacctacaa   8280
caatcacctc tacaagcaaa tctccaacag cacatctgga ggatcttcaa atgacaacgc   8340
ctacttcggc tacagcaccc cctgggggta ttttgacttc aacagattcc actgccactt   8400
ctcaccacgt gactggcagc gactcatcaa caacaactgg ggattccggc ctaagcgact   8460
caacttcaag ctcttcaaca ttcaggtcaa agaggttacg gacaacaatg gagtcaagac   8520
catcgccaat aaccttacca gcacggtcca ggtcttcacg gactcagact atcagctccc   8580
gtacgtgctc gggtcggctc acgagggctg cctcccgccg ttcccagcgg acgttttcat   8640
gattcctcag tacgggtatc tgacgcttaa tgatggaagc caggccgtgg gtcgttcgtc   8700
cttttactgc ctggaatatt tcccgtcgca aatgctaaga acgggtaaca acttccagtt   8760
cagctacgag tttgagaacg tacctttcca tagcagctac gctcacagcc aaagcctgga   8820
ccgactaatg aatccactca tcgaccaata cttgtactat ctctcaaaga ctattaacgg   8880
ttctggacag aatcaacaaa cgctaaaatt cagtgtggcc ggacccagca acatggctgt   8940
ccagggaaga aactacatac ctggacccag ctaccgacaa caacgtgtct caaccactgt   9000
gactcaaaac aacaacagcg aatttgcttg gcctggagct tcttcttggg ctctcaatgg   9060
acgtaatagc ttgatgaatc ctggacctgc tatggccagc cacaaagaag gagaggaccg   9120
tttctttcct ttgtctggat ctttaatttt tggcaaacaa ggaactggaa gagacaacgt   9180
ggatgcggac aaagtcatga taaccaacga agaagaaatt aaaactacta acccggtagc   9240
aacggagtcc tatggacaag tggccacaaa ccaccagagt gcccaagcac aggcgcagac   9300
cggctgggtt caaaaccaag gaatacttcc gggtatggtt tggcaggaca gagatgtgta   9360
cctgcaagga cccatttggg ccaaaattcc tcacacggac ggcaactttc acccttctcc   9420
gctgatggga gggtttggaa tgaagcaccc gcctcctcag atcctcatca aaaacacacc   9480
tgtacctgcg gatcctccaa cggccttcaa caaggacaag ctgaactctt tcatcaccca   9540
gtattctact ggccaagtca gcgtggagat cgagtgggag ctgcagaagg aaaacagcaa   9600
```

```
gcgctggaac ccggagatcc agtacacttc caactattac aagtctaata atgttgaatt   9660
tgctgttaat actgaaggtg tatatagtga accccgcccc attggcacca gatacctgac   9720
tcgtaatctg taattgcttg ttaatcaata aaccgtttaa ttcgtttcag ttgaactttg   9780
gtctctgcgg tttaaacggt cctgtattag aggtcacgtg agtgttttgc gacattttgc   9840
gacaccatgt ggtcacgctg ggtatttaag cccgagtgag cacgcagggt ctccattttg   9900
aagcgggagg tttgaacgcg cgcggccgcg tagtcccgca gtacgcggct aggcagatcg   9960
gccccttcca aatccgtgtc atcggaagac catgttggta gtttcataat ggattttatt  10020
gattgctatg taacctgaac gacggtatta atgggcttct taacatgaac gtgagtaacg  10080
gaaacattac gcttttcggt cgcgaatgac ggcgaactct gggccttgtg ggattataga  10140
tacgtcagtg ttcctcggga acggacaaag taggaaatat cgacgacatg gatcatgcca  10200
atatatcaac gcgggaagat gaccattgat gcagtgggaa ctggtgtccc acaaatatct  10260
agggcttgtg cagcggtcaa gggctgtgtt ccacctggga cgccagccca attatacgcc  10320
agaaacgctt gattttactc aggtagaaag gggggaaaata cactacgcga ccaactaata  10380
attcctttcg caaacttaat ggctgctaat tttcctcaag accggcttaa tgcctactac  10440
acttaaggcg cggatggcga gatacgacgc gggcacatac taggcacgtc atcggccagg  10500
cgttctaatt taagttcacg cataaataag cgtctctcga gactgcagat ccccgtctta  10560
aatttagtac acaacgctgt ttaccaccgg ggcgttatga cttgcagacc cgtgcgtgaa  10620
tatcctgtat cattcatcac tgctgggact accccacttt acatatctaa gggattcaac  10680
aaacttcggg tggttaatgt caagtgcgtt attggcgtat aacagggtga atgcacattg  10740
atggaatgcc ttcaaccaag ctgtggcgtc acgccagccg aacacgtttt acccaaactt  10800
agccctttg ctgcgaccct gctatctatt ggctatactc tatatgcaat gggtgcagat  10860
cggagaccgc gccattgtca ccaccccaag gaggggagat tcacgctcgc tcggattagc  10920
ttcccggatc atttatcaaa actggaaata ctctaagcta agttcacctt cagatccttg  10980
tcaagagttg tcggcccgat tagtcgttgc gcacacgtgg cgtaattaca gcacgcgagg  11040
tacattcgag tttatcctct gggctccatt caggcaatat gctgtcagca cgaagagtgt  11100
gacctggcgc tattgttggc gacttgacgc cacggaatac cagtgtatat acatcctagg  11160
agaactgcaa gacttcgggc gtgtatcgta ggttatggta gtcactggga tttgcacctg  11220
cgcacaatct gtttggtaaa gtaaaagcga tacttcgcga ctcccaataa gtaacgatac  11280
tgcgcggcat cccttagcgc tctcataccg agcgagatac agtctatata ctcaacagag  11340
cacgtttgga acctgtgagg ttcagcacca atcattcatc tataaactca tcgagaaaag  11400
tatggaggcc acgtgggctt cttcggttca gctaagcaga ctcatgaggg tgtggtctcg  11460
gctttggagg cagatattgt ccggaattgt aattgcgact gcgcggcagt atagagtgtc  11520
tctatcattg taggactcac gcacccatcg gacaaccacg tgatggcccc ttagttatat  11580
cgagggatag gggctatgct caagttagtc ttaatttcgc gtgcttgcaa ggcttatcgc  11640
cggtccctcc taccgtaccc ggcctttcag ggccatgatc tttgcctgct tccctgttta  11700
tctacaccaa tattgggaga cttgtatgac gagcgagcca ctaaagagga cgattgtcaa  11760
cagggtgctt tatcacataa tagcctgttt ctccaacagt gcttcaatta cctagcatca  11820
cagaatgcga taagcccacc acgtgtttcc caatggcggc tattcattaa tcgggacgac  11880
acccctattc gtggagagag catcctattg agtccgagct gttagcgcat gattacggtg  11940
```

-continued

```
ggccagacag attcgacgga atgccgctac tacgctggcg cgtaatcagt cggaaccaga  12000
attaattaac ctgcaggcag ctgcgcgctc gctcgctcac tgaggccgcc cgggcaaagc  12060
ccgggcgtcg ggcgaccttt ggtcgcccgg cctcagtgag cgagcgagcg cgcagagagg  12120
gagtggccaa ctccatcact aggggttcct tctagacgtg aggctccggt gcccgtcagt  12180
gggcagagcg cacatcgccc acagtccccg agaagttggg gggaggggtc ggcaattgaa  12240
ccggtgccta gagaaggtgg cgcggggtaa actgggaaag tgatgtcgtg tactggctcc  12300
gcctttttcc cgagggtggg ggagaaccgt atataagtgc agtagtcgcc gtgaacgttc  12360
tttttcgcaa cgggtttgcc gccagaacac aggtaagtgc cgtgtgtggt tcccgcgggc  12420
ctggcctctt tacgggttat ggcccttgcg tgccttgaat tacttccacg cccctggctg  12480
cagtacgtga ttcttgatcc cgagcttcgg gttggaagtg ggtgggagag ttcgaggcct  12540
tgcgcttaag gagccccttc gcctcgtgct tgagttgagg cctggcctgg gcgctggggc  12600
cgccgcgtgc gaatctggtg gcaccttcgc gcctgtctcg ctgctttcga taagtctcta  12660
gccatttaaa atttttgatg acctgctgcg acgctttttt tctggcaaga tagtcttgta  12720
aatgcgggcc aagatctgca cactggtatt tcggtttttg gggccgcggg cggcgacggg  12780
gcccgtgcgt cccagcgctc atgttcggcg aggcggggcc tgcgagcgcg gccaccgaga  12840
atcggacggg ggtagtctca agctggccgg cctgctctgg tgcctggcct cgcgccgccg  12900
tgtatcgccc cgccctgggc ggcaaggctg gcccggtcgg caccagttgc gtgagcggaa  12960
agatggccgc ttcccggccc tgctgcaggg agctcaaaat ggaggacgcg gcgctcggga  13020
gagcgggcgg gtgagtcacc cacacaaagg aaaagggcct ttccgtcctc agccgtcgct  13080
tcatgtgact ccacggagta ccgggcgccg tccaggcacc tcgattagtt ctcgagcttt  13140
tggagtacgt cgtctttagg ttggggggag gggttttatg cgatggagtt tccccacact  13200
gagtgggtgg agactgaagt taggccagct tggcacttga tgtaattctc cttggaattt  13260
gccctttttg agtttggatc ttggttcatt ctcaagcctc agacagtggt tcaaagtttt  13320
tttcttccat ttcaggtgtc gtgagccacc atggtgagca agggcgagga ggataacatg  13380
gccatcatca aggagttcat gcgcttcaag gtgcacatgg agggctccgt gaacggccac  13440
gagttcgaga tcgagggcga gggcgagggc cgcccctacg agggcaccca gaccgccaag  13500
ctgaaggtga ccaagggtgg cccccctgccc ttcgcctggg acatcctgtc ccctcagttc  13560
atgtacggct ccaaggccta cgtgaagcac cccgccgaca tccccgacta cttgaagctg  13620
tccttccccg agggcttcaa gtgggagcgc gtgatgaact tcgaggacgg cggcgtggtg  13680
accgtgaccc aggactcctc cctgcaggac ggcgagttca tctacaaggt gaagctgcgc  13740
ggcaccaact tcccctccga cggccccgta atgcagaaga agaccatggg ctgggaggcc  13800
tcctccgagc ggatgtaccc cgaggacggc gccctgaagg gcgagatcaa gcagaggctg  13860
aagctgaagg acggcggcca ctacgacgct gaggtcaaga ccacctacaa ggccaagaag  13920
cccgtgcagc tgcccggcgc ctacaacgtc aacatcaagt tggacatcac ctcccacaac  13980
gaggactaca ccatcgtgga acagtacgaa cgcgccgagg gccgccactc caccggcggc  14040
atggacgagc tgtacaagta agtcgactac tggccgaagc cgcttggaat aaggccggtg  14100
tgcgtttgtc tatatgtgat tttccaccat attgccgtct tttggcaatg tgagggcccg  14160
gaaacctggc cctgtcttct tgacgagcat tcctaggggt ctttcccctc tcgccaaagg  14220
aatgcaaggt ctgttgaatg tcgtgaagga agcagttcct ctggaagctt cttgaagaca  14280
aacaacgtct gtagcgaccc tttgcaggca gcggaacccc ccacctggcg acaggtgcct  14340
```

-continued

```
ctgcggccaa aagccacgtg tataagatac acctgcaaag gcggcacaac cccagtgcca  14400
cgttgtgagt tggatagttg tggaaagagt caaatggctc tcctcaagcg tattcaacaa  14460
ggggctgaag gatgcccaga aggtacccca ttgtatggga tctgatctgg ggcctcggtg  14520
cacatgcttt acatgtgttt agtcgaggtt aaaaaacgtc taggccccc gaaccacggg  14580
gacgtggttt tcctttgaaa aacacgatcg tacggccacc atgtggggag cctgcttgct  14640
gctgctgggc ctcagcctac aggtgtgccc gagcgtcatc ccagtggagg aggagaatcc  14700
agccttctgg aaccgaaagg cagccgaggc cctggatgct gccaagaagc tgaagcccat  14760
tcagacatca gctaagaacc tcgttatcct catgggagat gggatggggg tgtctacagt  14820
aaccgctacc cggatcttaa aggggcagca gcaaggccat ctgggacctg agacacagtt  14880
agctatggat cgctttccac acatggctct gtccaagaca tacaacacag acaagcagat  14940
cccggacagc gcaggcacag gtacagcctt tctctgcggg gtcaaaacca acatgaaggt  15000
cattggcttg agtgcagctg cacgcttcaa ccagtgcaac acgacatggg gtaacgaggt  15060
cgtctcggtg atgcaccgtg ctaagaaagc aggaaagtct gtgggagtgg tgaccaccac  15120
gtcggtgcag catgcttctc cggccggcac ctacgcgcac actgtgaacc gtggttggta  15180
ctcggatgca caaatgcctg cctcagcgct acaggatggc tgcaaagaca tctctactca  15240
gctcatctcc aacatggaca ttgatgtgat cctcggtggt ggccgcaagt tcatgtttcc  15300
caaggggaca ccagaccagg aatatccaac tgacaccaag caggctggaa ccaggctgga  15360
tggacgcaac ctagttcaag agtggctggc aaagcaccag ggagcccggt atgtttggaa  15420
ccgctcagag ctgattcagg catccctgaa ccgatctgtg acacacctca tgggcctctt  15480
tgagcctaac gacatgaaat atgaaatcca ccgagaccct gctcaggacc cttccctggc  15540
cgagatgacg gaggtggctg tgcgcatgct cagcaggaac cccaaaggct tctatctctt  15600
tgtggaaggg ggtcgcatcg accatggcca ccatgaaact gtagcctatc gtgccctgac  15660
tgaggctgtc atgttcgact cggctgttga caaggcagac aagctcacca gtgagcagga  15720
cacgatgatc cttgtcactg ccgaccactc tcacgtcttc tcttttggtg gttacacaca  15780
gagaggggct tccatctttg gactggctcc cttcaaggct gaggatggca aatcctttac  15840
ctcgatacta tacggcaacg gtcctggtta caagctccat aatggcgccc gggctgatgt  15900
cactgaggaa gagagcagca accccacgta ccagcagcag gctgctgtac ccctgtcgtc  15960
agagacccac agcggggagg acgtggcaat attcgcgcgt ggcccacagg cgcagctggt  16020
gcacggagtt caggagcaga actacatcgc gcacgtcatg gccttcgcag cctgcctgga  16080
gccctacact gactgcggcc tggcatcccc tgctggccag agcagtgcag tgagcccggg  16140
ctgaacgcgt gggggaggct aactgaaaca cggaaggaga caataccgga aggaacccgc  16200
gctatgacgg caataaaaag acagaataaa acgcacggtg ttgggtcgtt tgttcataaa  16260
cgcggggttc ggtcccaggg ctggcactct gtcgataccc caccgagacc ccattggggc  16320
caatacgccc gcgtttcttc cttttcccca ccccaccccc caagttcggg tgaaggccca  16380
gggctcgcag ccaacgtcgg ggcggcaggc cctgccatag ccatctatgt cgggtgcgga  16440
gaaagaggta ataggaaccc ctagtgatgg agttggccac tccctctctg cgcgctcgct  16500
cgctcactga ggccgggcga ccaaaggtcg cccgacgccc gggctttgcc cgggcggcct  16560
cagtgagcga gcgagcgcgc agctgcctgc aggttaatta acctgcaggt gtacacaatg  16620
atacgatccc gtttctgcga cgtactcggg tgtagctggg accctgtcgc atttaatcgc  16680
```

-continued

```
cggtcaatag gtacaccgtg ctgatcttgg atactcctga tcgcgatgta acccgagcgg  16740
cgctactaat gggcgtccta acacgagcgc gaataaccac ttgcgctagg caggatttac  16800
gatggtcatc tggaacggac gggtacacca tgccaaaatt tgctcctagt tcacaaggtc  16860
aaacggtgac ccggaggcca gtccactcct tgtcctcgtc cttacgttac cgtaacctct  16920
gacctggagc ctaaggctgc tccggcattt taaaaaccac acaaataagg cttcacacta  16980
ttcctattat cttgtgtcct acctaagagg tagtggagcg agtaggtaga cacaggcact  17040
caccaccgat gttccgccca tgggccatgg ttaaggtccg aatgaaaccc gtatgcaagt  17100
taccggcctt atattaataa ggttggtata catcctaaaa gctctctcgg acgtgaccaa  17160
atacaggcat ccacggagca ctactgaatg ggcacgtgga ccggcgagtg agaaatcgag  17220
cagcattaag tcattcttag taagccgaga tgggtctgcg ttatgtacgt ctagtgggga  17280
aacaagttgg tggacaaacg ttacgcctaa ggagctaata tttcggtcag gttgcgctgg  17340
gtcaaatcaa ccggtcctgg taacggagcg atggttaggt gtattacact agcgatgggc  17400
cgtgccggat ggtacgccac gttctccgag ccagtgaaat tggatgagaa ctcgtaaatc  17460
tctcgttgca aacagcttcc tcaatatatg acctggccac tgatgagagg gtaacactta  17520
attcctagaa tgtctgacga catcaccctt aagcagacac actgcgatgt gtggacgcta  17580
gggtgtctct ttccacgttt gacttagccc atgatgtctt gactaagatg gcagggtatt  17640
tcccccttatt cgtgtatgta ccactattac cgtcgattga ccgtcgccgc ttatacgtcg  17700
tgccctgtgc cttggcaatt ttgtccctgg ataacccgcc ttgcttctat cgaggtcctt  17760
gaataagtta atgcaacttg tggaggaaca tagggaatgt ggcgtgctgc ttagatatgg  17820
agtgcaagaa gtcctctggg ttgtagtttc actgttacgt cctagccagt gaagcactgg  17880
catgcagctt tatctgagga ttccactcac tgcttacaag aatttgccaa gctggtgccg  17940
atatgacccc aacgctatcc agagtttaag ttgtcatctc tctccatcat aattgccaca  18000
gtgtgttgtg tctacgaata gctattaaaa taccagcccc tgagaacgat gcccgacaca  18060
tagggcagtg caggcagcat aacgtgcaga tcaacataat ttccactaag tgttgatata  18120
gtttactggc tgagagccgc catattggaa cgacgacgag agcgcgtatc ctgcccaacc  18180
agaaatacgt gtccaatcca tataactgac caaagctgcg gacagtttcc tctccaccta  18240
caacgggatt agcgcacttg cttgtagtga ggcaggtata acccacggca cgtaacacct  18300
ttagacgttc ggttccgcaa tcgcacaatg tactactatt agagaactat agcaaggaac  18360
ttatagcgta tcgaaagttc atccctgcgg cccatagccg taaccaccgt ggggttattt  18420
taaactttaa gttgtaccct caggcaagcg aagaccggta ctttacctac atggggccgc  18480
tttccgagcc acgccgcacc ccaacatatt cctacgcgct gtaataatga acataagaga  18540
aaatggagtt gggtgacagc acatatcgac tacctagcga ctaccgcaac acaaagtaga  18600
tcccgccggt atcctccttt catgcaggac gggttaccca ggaatgcgtt tgtttgactg  18660
gtgcccgctg aggcgctgaa tatctcgcga tagcgtgtac cgatcaagaa agcactccgg  18720
gatatctggc aaacagctat tatgggtatt atgggtttca gggagtggcg cagctgcttc  18780
atccccgtgg cccgttgctc gcgtttgctg gcggtgtccc cggaagaaat atatttgcat  18840
gtctttagtt ctatgatgac acaaaccccg cccagcgtct tgtcattggc gaaaacacgc  18900
agatgcagtc ggggcggcgc ggtcccaggt ccacttcgca tattaaggtg acgcgtgtgg  18960
cctcgaacac agagcgacgg ccaccatgac cgagtacaag cccacggtgc gcctcgccac  19020
ccgcgacgac gtcccccggg ccgtacgcac cctcgccgcc gcgttcgccg actaccccgc  19080
```

```
cacgcgccac accgttgacc cggaccgcca catcgagcgg gtcaccgagc tgcaagaact  19140
cttcctcacg cgcgtcgggc tcgacatcgg caaggtgtgg gtcgcggacg acggcgccgc  19200
ggtggcggtc tggaccacgc cggagagcgt cgaagcgggg gcggtgttcg ccgagatcgg  19260
cccgcgcatg gccgagttga gcggttcccg gctggccgcg cagcaacaga tggaaggcct  19320
cctggcgccg caccggccca aggagcccgc gtggttcctg gccaccgtcg gcgtctcgcc  19380
cgaccaccag ggcaagggtc tgggcagcgc cgtcgtgctc cccggagtgg aggcggccga  19440
gcgcgccggg gtgcccgcct tcctggagac ctccgcgccc cgcaacctcc ccttctacga  19500
gcggctcggc ttcaccgtca ccgccgacgt cgaggtgccc gaaggaccgc gcacctggtg  19560
catgacccgc aagcccggtg cctgatgtgc cttctagttg ccagccatct gttgtttgcc  19620
cctcccccgt gccttccttg accctggaag gtgccactcc cactgtcctt tcctaataaa  19680
atgaggaaat tgcatcgcat tgtctgagta ggtgtcattc tattctgggg ggtggggtgg  19740
ggcaggacag caagggggag gattgggaag acaatagcag gcatgctggg gatgcggtgg  19800
gctctatggt ccccccttatt aaccctaaac gggtagcata tgcttcccgg gtagtagtat  19860
atactatcca gactaaccct aattcaatag catatgttac ccaacgggaa gcatatgcta  19920
tcgaattagg gttagtaaaa gggtcctaag gaacagcgat ctggatagca tatgctatcc  19980
taatctatat ctgggtagca tatgctatcc taatctatat ctgggtagca taggctatcc  20040
taatctatat ctgggtagca tatgctatcc taatctatat ctgggtagta tatgctatcc  20100
taatttatat ctgggtagca taggctatcc taatctatat ctgggtagca tatgctatcc  20160
taatctatat ctgggtagta tatgctatcc taatctgtat ccgggtagca tatgctatcc  20220
tcatgcatat acagtcagca tatgataccc agtagtagag tgggagtgct atcctttgca  20280
tatgccgcca cctcccaagg attatgggtg acgtcaggtg gcacttttcg gggaaatgtg  20340
cgcggaaccc ctatttgttt atttttctaa atacattcaa atatgtatcc gctcatgaga  20400
caataaccct gataaatgct tcaataatat tgaaaaagga agagtatgag tattcaacat  20460
ttccgtgtcg cccttattcc cttttttgcg gcattttgcc ttcctgtttt tgctcaccca  20520
gaaacgctgg tgaaagtaaa agatgctgaa gatcagttgg gtgcacgagt gggttacatc  20580
gaactggatc tcaacagcgg taagatcctt gagagttttc gccccgaaga acgttttcca  20640
atgatgagca cttttaaagt tctgctatgt ggcgcggtat tatcccgtat tgacgccggg  20700
caagagcaac tcggtcgccg catacactat tctcagaatg acttggttga gtactcacca  20760
gtcacagaaa agcatcttac ggatggcatg acagtaagag aattatgcag tgctgccata  20820
accatgagtg ataacactgc ggccaactta cttctgacaa cgatcggagg accgaaggag  20880
ctaaccgctt ttttgcacaa catgggggat catgtaactc gccttgatcg ttgggaaccg  20940
gagctgaatg aagccatacc aaacgacgag cgtgacacca cgatgcctgt agcaatggca  21000
acaacgttgc gcaaactatt aactggcgaa ctacttactc tagcttcccg gcaacaatta  21060
atagactgga tggaggcgga taaagttgca ggaccacttc tgcgctcggc ccttccggct  21120
ggctggttta ttgctgataa atctggagcc ggtgagcgtg ggtctcgcgg tatcattgca  21180
gcactggggc cagatggtaa gccctcccgt atcgtagtta tctacacgac ggggagtcag  21240
gcaactatgg atgaacgaaa tagacagatc gctgagatag gtgcctcact gattaagcat  21300
tggtaactgt cagaccaagt ttactcatat atactttaga ttgatttaaa acttcatttt  21360
taatttaaaa ggatctaggt gaagatcctt tttgataatc tcatgaccaa aatcccttaa  21420
```

cgtgagtttt cgttccactg agcgtcagac cccgtagaaa agatcaaagg atcttcttga 21480
gatccttttt ttctgcgcgt aatctgctgc ttgcaaacaa aaaaaccacc gctaccagcg 21540
gtggtttgtt tgccggatca agagctacca actctttttc cgaaggtaac tggcttcagc 21600
agagcgcaga taccaaatac tgttcttcta gtgtagccgt agttaggcca ccacttcaag 21660
aactctgtag caccgcctac atacctcgct ctgctaatcc tgttaccagt ggctgctgcc 21720
agtggcgata agtcgtgtct taccgggttg gactcaagac gatagttacc ggataaggcg 21780
cagcggtcgg gctgaacggg gggttcgtgc acacagccca gcttggagcg aacgacctac 21840
accgaactga gatacctaca gcgtgagcta tgagaaagcg ccacgcttcc cgaagggaga 21900
aaggcggaca ggtatccggt aagcggcagg gtcggaacag gagagcgcac gagggagctt 21960
ccagggggaa acgcctggta tctttatagt cctgtcgggt ttcgccacct ctgacttgag 22020
cgtcgatttt tgtgatgctc gtcagggggg cggagcctat ggaaaaacgc cagcaacgcg 22080
gcctttttac ggttcctggc cttttgctgg ccttttgctc acatgt 22126

<210> SEQ ID NO 71
<211> LENGTH: 19
<212> TYPE: DNA
<213> ORGANISM: Artificial Sequence
<220> FEATURE:
<223> OTHER INFORMATION: Beta-Actin Splice Donor

<400> SEQUENCE: 71
gtggatccag gtgggtgtc 19

<210> SEQ ID NO 72
<211> LENGTH: 19
<212> TYPE: DNA
<213> ORGANISM: Artificial Sequence
<220> FEATURE:
<223> OTHER INFORMATION: Beta-Actin Splice Acceptor

<400> SEQUENCE: 72
ccctcctcag gaggaccag 19

<210> SEQ ID NO 73
<211> LENGTH: 863
<212> TYPE: DNA
<213> ORGANISM: Artificial Sequence
<220> FEATURE:
<223> OTHER INFORMATION: Mutated 5' portion of the AAV2 rep gene upstream of the stop cassette in the exemplified construct

<400> SEQUENCE: 73
ggtcctgtat tagaggtcac gtgagtgttt tgcgacattt tgcgacacca tgtggtcacg 60
ctgggtattt aagcccgagt gagcacgcag ggtctccatt ttgaagcggg aggtttgaac 120
gcgcagccgc catgccgggg ttttacgaga ttgtgattaa ggtccccagc gaccttgacg 180
agcatctgcc cggcatttct gacagctttg tgaactgggt ggccgagaag gaatgggagt 240
tgccgccaga ttctgacatg gatctgaatc tgattgagca ggcacccctg accgtggccg 300
agaagctgca gcgcgacttt ctgacggaat ggcgccgtgt gagtaaggcc ccggaggccc 360
ttttctttgt gcaatttgag aagggagaga gctacttcca catgcacgtg ctcgtggaaa 420
ccaccggggt gaaatccatg gttttgggac gtttcctgag tcagattcgc gaaaaactga 480
ttcagagaat ttaccgcggg atcgagccga ctttgccaaa ctggttcgcg gtcacaaaga 540
ccagaaatgg cgccggaggc gggaacaagg tggtggatga gtgctacatc cccaattact 600

-continued

```
tgctccccaa aacccagcct gagctccagt gggcgtggac taatatggaa cagtatttaa    660

gcgcctgttt gaatctcacg gagcgtaaac ggttggtggc gcagcatctg acgcacgtgt    720

cgcagacgca ggagcagaac aaagagaatc agaatcccaa ttctgatgcg ccggtgatca    780

gatcaaaaac ttcagccaga tacatggagc tggtcgggtg gctcgtggac aaggggatta    840

cctcggagaa gcagtggatc cag                                            863
```